(12) United States Patent
Mulder

(10) Patent No.: US 12,097,252 B2
(45) Date of Patent: *Sep. 24, 2024

(54) FORMULATION OF A PEPTIDE VACCINE

(71) Applicant: ISA Pharmaceuticals B.V., Leiden (NL)

(72) Inventor: Gwenn Eveline Mulder, Utrecht (NL)

(73) Assignee: ISA PHARMACEUTICALS B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/894,945

(22) Filed: Aug. 24, 2022

(65) Prior Publication Data

US 2023/0233658 A1 Jul. 27, 2023

Related U.S. Application Data

(63) Continuation of application No. 16/898,141, filed on Jun. 10, 2020, now Pat. No. 11,426,458, which is a continuation of application No. 16/311,629, filed as application No. PCT/EP2017/064882 on Jun. 19, 2017, now Pat. No. 10,702,598.

(30) Foreign Application Priority Data

Jun. 20, 2016 (EP) ..................................... 16175215

(51) Int. Cl.
| | |
|---|---|
| *A61K 39/12* | (2006.01) |
| *A61K 9/107* | (2006.01) |
| *A61K 38/04* | (2006.01) |
| *A61K 39/00* | (2006.01) |
| *A61K 47/10* | (2017.01) |
| *A61K 47/12* | (2006.01) |
| *A61K 47/14* | (2017.01) |
| *A61P 35/00* | (2006.01) |
| *A61K 9/00* | (2006.01) |

(52) U.S. Cl.
CPC ............. *A61K 39/12* (2013.01); *A61K 9/107* (2013.01); *A61K 39/0011* (2013.01); *A61K 47/10* (2013.01); *A61K 47/12* (2013.01); *A61K 47/14* (2013.01); *A61P 35/00* (2018.01); *A61K 9/0019* (2013.01); *A61K 9/1075* (2013.01); *A61K 2039/55566* (2013.01); *A61K 2039/585* (2013.01); *A61K 2039/70* (2013.01); *C12N 2710/20034* (2013.01)

(58) Field of Classification Search
None
See application file for complete search history.

(56) References Cited

U.S. PATENT DOCUMENTS

| | | | |
|---|---|---|---|
| 7,202,034 B2 | 4/2007 | Van Der Burg et al. | |
| 2007/0010424 A1 | 1/2007 | Pedersen et al. | |
| 2009/0118354 A1 | 5/2009 | Liu et al. | |
| 2010/0196353 A1 | 8/2010 | Van Der Burg et al. | |
| 2015/0152140 A1* | 6/2015 | Sorensen | ......... G01N 33/56977 514/21.7 |

FOREIGN PATENT DOCUMENTS

| | | |
|---|---|---|
| WO | WO-2010/132867 A1 | 11/2010 |
| WO | WO-2013/113326 A1 | 8/2013 |

OTHER PUBLICATIONS

Anonymous, "A Guide to Handling and Storing Peptides", Peptides and Immunology, Mar. 8, 2006, pp. 1-3.
Anonymous, "Peptide Solubility Guidelines", ANASPEC, Dec. 28, 2011, pp. 1-2.
Ascarateil et al. "Safety data of Montanide ISA 51 VG and Montanide ISA 720 VG, two adjuvants dedicated to human therapeutic vaccines", Journal of ImmunoTherapy of Cancer, 2015, p. 428.
Bell et al., "Peptide Stability in Solids and Solutions", Biotechnology Progess, vol. 13, No. 4, 1997, pp. 342-346.
International Search Report issued in PCT/EP2017/064882, mailed Oct. 9, 2017.
Melief et al., Therapeutic cancer vaccines, The Journal of Clinical Investigation, vol. 125, No. 9, Sep. 2015, 12 pages.
Notice of Allowance on U.S. Appl. No. 16/898,141 dated Apr. 25, 2022.
Notice of Allowance on U.S. Appl. No. 16/311,629 dated Mar. 5, 2020.
Nuijen et al., "Compatibility and stability of aplidine, a novel marine-deprived depsipeptide antitumor agent, in infusion devices, and its hemolytic and precipitation", Anti-Cancer Drugs, vol. 10, No. 10, Nov. 1, 1999, pp. 879-888.
Strickley, "Solubilizing Excipients in Oral and Injectable Formulations", Pharmaceutical Research, vol. 21, No. 2, Feb. 1, 2004, pp. 201-230.
Written Opinion of the International Searching Authority issued in PCT/EP2017/064882, mailed Oct. 9, 2017.
Zhao et al., "Stabilization of eptifibatide by cosolvents", International Journal of Pharmaceutics, vol. 218, pp. 43-56, 2001.
Zhao et al., "Stabilization of eptifibatide by cosolvents", International Journal of Pharmaceutics, vol. 218, No. 1-2, May 1, 2001, pp. 43-56.

* cited by examiner

*Primary Examiner* — Nianxiang Zou
(74) *Attorney, Agent, or Firm* — Sunit Talapatra; Foley & Lardner LLP

(57) ABSTRACT

The invention relates to a novel reconstitution composition, a pharmaceutical composition and kit of parts comprising said reconstitution composition. The invention further relates to a method of treatment using said pharmaceutical composition and/or the pharmaceutical composition for use as a medicament. Also provided is a method for reconstituting dried peptides and a method for preparing a pharmaceutical composition using the reconstitution composition of the invention.

20 Claims, 17 Drawing Sheets

Specification includes a Sequence Listing.

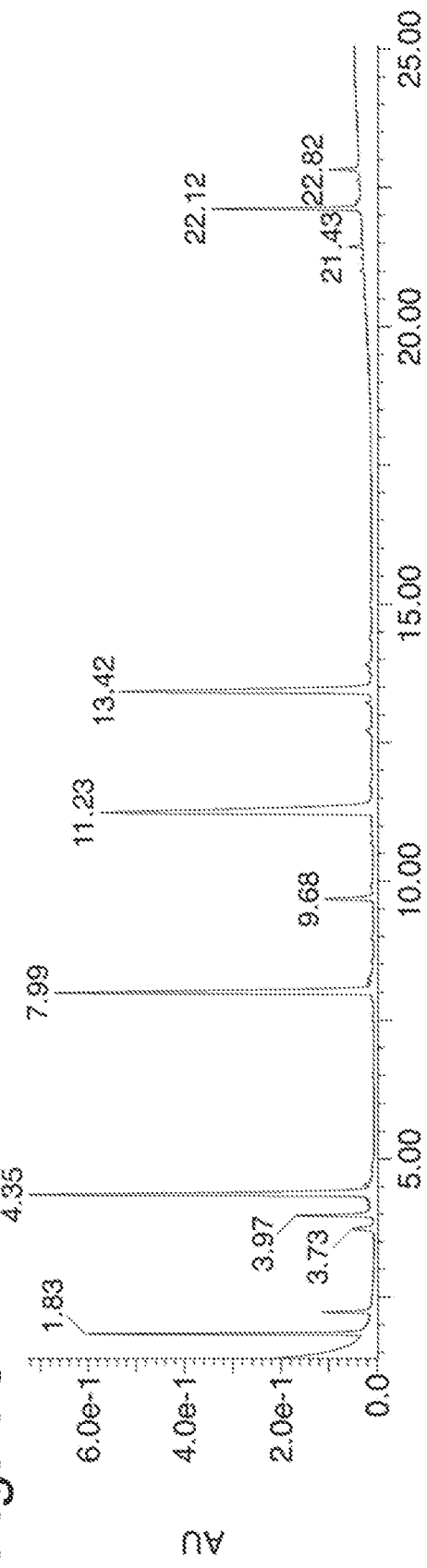
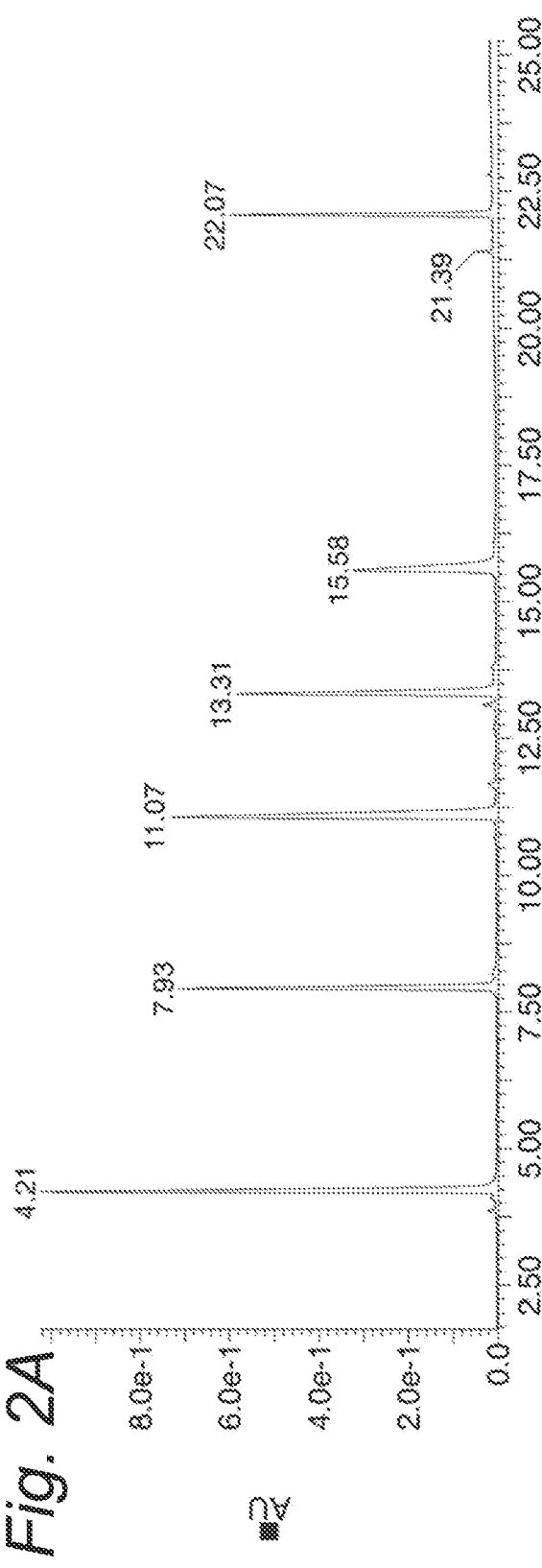

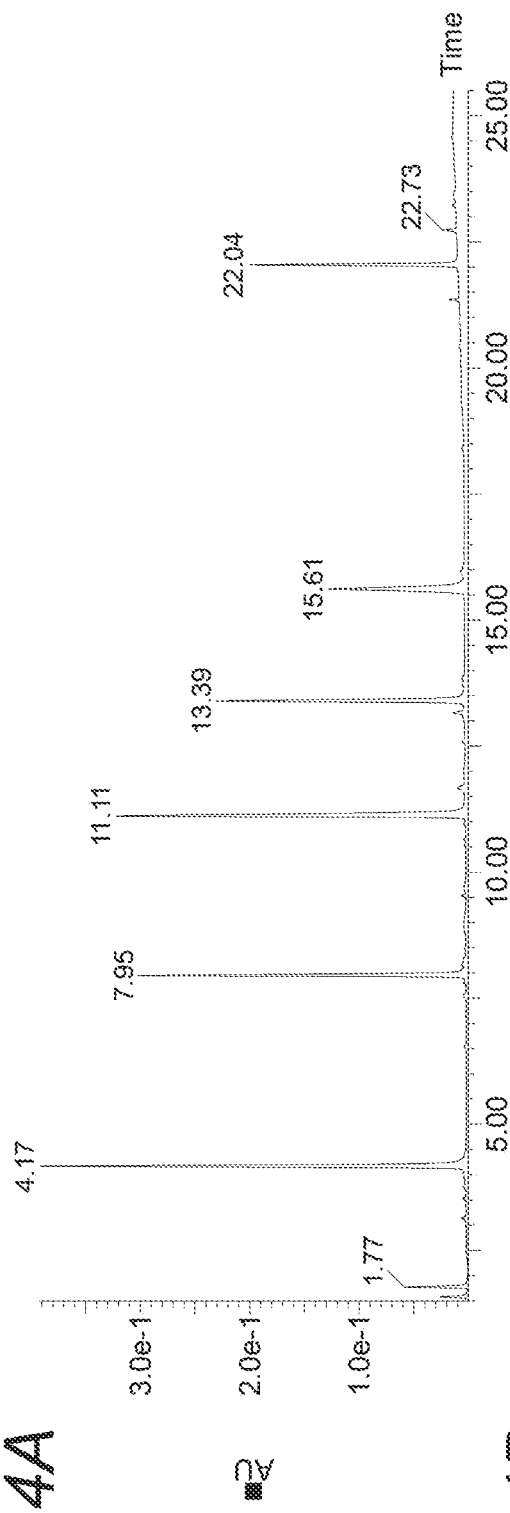
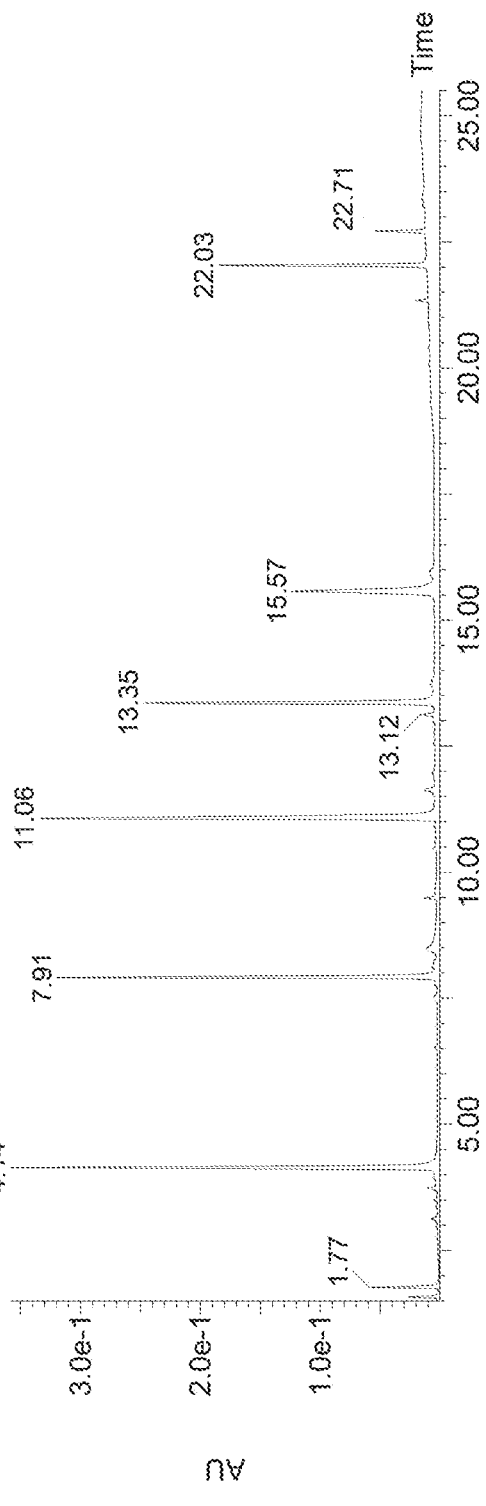
Fig. 4A
Fig. 4B

SEQUENCE LISTING

```
Sequence total quantity: 232
SEQ ID NO: 1                moltype = AA  length = 25
FEATURE                     Location/Qualifiers
REGION                      1..25
                            note = peptide
source                      1..25
                            mol_type = protein
                            organism = synthetic construct
SEQUENCE: 1
DKCLKFYSKI SEYRHYCYSL YGTTL                                              25

SEQ ID NO: 2                moltype = AA  length = 35
FEATURE                     Location/Qualifiers
REGION                      1..35
                            note = peptide
source                      1..35
                            mol_type = protein
                            organism = synthetic construct
SEQUENCE: 2
LYCYEQLNDS SEEEDEIDGP AGQAEPDRAH YNIVT                                    35

SEQ ID NO: 3                moltype = AA  length = 35
FEATURE                     Location/Qualifiers
REGION                      1..35
                            note = peptide
source                      1..35
                            mol_type = protein
                            organism = synthetic construct
SEQUENCE: 3
MHGDTPTLHE YMLDLQPETT DLYCYEQLND SSEEE                                    35

SEQ ID NO: 4                moltype = AA  length = 32
FEATURE                     Location/Qualifiers
REGION                      1..32
                            note = peptide
source                      1..32
                            mol_type = protein
                            organism = synthetic construct
SEQUENCE: 4
RCINCQKPLC PEEKQRHLDK KQRFHNIRGR WT                                       32

SEQ ID NO: 5                moltype = AA  length = 35
FEATURE                     Location/Qualifiers
REGION                      1..35
                            note = peptide
```

```
source                      1..35
                            mol_type = protein
                            organism = synthetic construct
SEQUENCE: 5
TLRLCVQSTH VDIRTLEDLL MGTLGIVCPI CSQKP                               35

SEQ ID NO: 6                moltype = AA   length = 35
FEATURE                     Location/Qualifiers
REGION                      1..35
                            note = peptide
source                      1..35
                            mol_type = protein
                            organism = synthetic construct
SEQUENCE: 6
GQAEPDRAHY NIVTFCCKCD STLRLCVQST HVDIR                               35

SEQ ID NO: 7                moltype = AA   length = 32
FEATURE                     Location/Qualifiers
REGION                      1..32
                            note = peptide
source                      1..32
                            mol_type = protein
                            organism = synthetic construct
SEQUENCE: 7
DKKQRFHNIR GRWTGRCMSC CRSSRTRRET QL                                  32

SEQ ID NO: 8                moltype = AA   length = 25
FEATURE                     Location/Qualifiers
REGION                      1..25
                            note = peptide
source                      1..25
                            mol_type = protein
                            organism = synthetic construct
SEQUENCE: 8
HYCYSLYGTT LEQQYNKPLC DLLIR                                          25

SEQ ID NO: 9                moltype = AA   length = 25
FEATURE                     Location/Qualifiers
REGION                      1..25
                            note = peptide
source                      1..25
                            mol_type = protein
                            organism = synthetic construct
SEQUENCE: 9
KQQLLRREVY DFAFRDLCIV YRDGN                                          25

SEQ ID NO: 10               moltype = AA   length = 32
FEATURE                     Location/Qualifiers
REGION                      1..32
                            note = peptide
source                      1..32
                            mol_type = protein
                            organism = synthetic construct
SEQUENCE: 10
LPQLCTELQT TIHDIILECV YCKQQLLRRE VY                                  32

SEQ ID NO: 11               moltype = AA   length = 32
FEATURE                     Location/Qualifiers
REGION                      1..32
                            note = peptide
source                      1..32
                            mol_type = protein
                            organism = synthetic construct
SEQUENCE: 11
MHQKRTAMFQ DPQERPRKLP QLCTELQTTI HD                                  32

SEQ ID NO: 12               moltype = AA   length = 26
FEATURE                     Location/Qualifiers
REGION                      1..26
                            note = peptide
source                      1..26
                            mol_type = protein
                            organism = synthetic construct
SEQUENCE: 12
RDLCIVYRDG NPYAVCDKCL KFYSKI                                         26

SEQ ID NO: 13               moltype = AA   length = 32
FEATURE                     Location/Qualifiers
REGION                      1..32
```

```
                        note = peptide
source                  1..32
                        mol_type = protein
                        organism = synthetic construct
SEQUENCE: 13
YGTTLEQQYN KPLCDLLIRC INCQKPLCPE EK                              32

SEQ ID NO: 14           moltype = AA  length = 365
FEATURE                 Location/Qualifiers
source                  1..365
                        mol_type = protein
                        organism = Human papillomavirus type 16
SEQUENCE: 14
METLCQRLNV CQDKILTHYE NDSTDLRDHI DYWKHMRLEC AIYYKAREMG FKHINHQVVP  60
TLAVSKNKAL QAIELQLTLE TIYNSQYSNE KWTLQDVSLE VYLTAPTGCI KKHGYTVEVQ 120
FDGDICNTMH YTNWTHIYIC EEASVTVVEG QVDYYGLYYV HEGIRTYFVQ FKDDAEKYSK 180
NKVWEVHAGG QVILCPTSVF SSNEVSSPEI IRQHLANHPA ATHTKAVALG TEETQTTIQR 240
PRSEPDTGNP CHTTKLLHRD SVDSAPILTA FNSSHKGRIN CNSNTTPIVH LKGDANTLKC 300
LRYRFKKHCT LYTAVSSTWH WTGHNVKHKS AIVTLTYDSE WQRDQFLSQV KIPKTITVST 360
GFMSI                                                           365

SEQ ID NO: 15           moltype = AA  length = 158
FEATURE                 Location/Qualifiers
source                  1..158
                        mol_type = protein
                        organism = Human papillomavirus type 16
SEQUENCE: 15
MHQKRTAMFQ DPQERPRKLP QLCTELQTTI HDIILECVYC KQQLLRREVY DFAFRDLCIV  60
YRDGNPYAVC DKCLKFYSKI SEYRHYCYSL YGTTLEQQYN KPLCDLLIRC INCQKPLCPE 120
EKQRHLDKKQ RFHNIRGRWT GRCMSCCRSS RTRRETQL                        158

SEQ ID NO: 16           moltype = AA  length = 98
FEATURE                 Location/Qualifiers
source                  1..98
                        mol_type = protein
                        organism = Human papillomavirus type 16
SEQUENCE: 16
MHGDTPTLHE YMLDLQPETT DLYCYEQLND SSEEEDEIDG PAGQAEPDRA HYNIVTFCCK  60
CDSTLRLCVQ STHVDIRTLE DLLMGTLGIV CPICSQKP                         98

SEQ ID NO: 17           moltype = AA  length = 365
FEATURE                 Location/Qualifiers
source                  1..365
                        mol_type = protein
                        organism = Human papillomavirus type 18
SEQUENCE: 17
MQTPKETLSE RLSCVQDKII DHYENDSKDI DSQIQYWQLI RWENAIFFAA REHGIQTLNH  60
QVVPAYNISK SKAHKAIELQ MALQGLAQSA YKTEDWTLQD TCEELWNTEP THCFKKGGQT 120
VQVYFDGNKD NCMTYVAWDS VYYMTDAGTW DKTATCVSHR GLYYVKEGYN TFYIEFKSEC 180
EKYGNTGTWE VHFGNNVIDC NDSMCSTSDD TVSATQLVKQ LQHTPSPYSS TVSVGTAKTY 240
GQTSAATRPG HCGLAEKQHC GPVNPLLGAA TPTGNNKRRK LCSGNTTPII HLKGDRNSLK 300
CLRYRLRKHS DHYRDISSTW HWTGAGNEKT GILTVTYHSE TQRTKFLNTV AIPDSVQILV 360
GYMTM                                                           365

SEQ ID NO: 18           moltype = AA  length = 158
FEATURE                 Location/Qualifiers
source                  1..158
                        mol_type = protein
                        organism = Human papillomavirus type 18
SEQUENCE: 18
MARFEDPTRR PYKLPDLCTE LNTSLQDIEI TCVYCKTVLE LTEVFEFAFK DLFVVYRDSI  60
PHAACHKCID FYSRIRELRH YSDSVYGDTL EKLTNTGLYN LLIRCLRCQK PLNPAEKLRH 120
LNEKRRFHNI AGHYRGQCHS CCNRARQERL QRRRETQV                        158

SEQ ID NO: 19           moltype = AA  length = 105
FEATURE                 Location/Qualifiers
source                  1..105
                        mol_type = protein
                        organism = Human papillomavirus type 18
SEQUENCE: 19
MHGPKATLQD IVLHLEPQNE IPVDLLCHEQ LSDSEEENDE IDGVNHQHLP ARRAEPQRHT  60
MLCMCCKCEA RIKLVVESSA DDLRAFQQLF LNTLSFVCPW CASQQ                105

SEQ ID NO: 20           moltype = AA  length = 30
FEATURE                 Location/Qualifiers
REGION                  1..30
                        note = peptide
source                  1..30
                        mol_type = protein
```

```
                        organism = synthetic construct
SEQUENCE: 20
RPRKLPQLCT ELQTTIHDII LECVYCKQQL                                    30

SEQ ID NO: 21           moltype = AA   length = 22
FEATURE                 Location/Qualifiers
REGION                  1..22
                        note = peptide
source                  1..22
                        mol_type = protein
                        organism = synthetic construct
SEQUENCE: 21
RREVYDFAFR DLCIVYRDGN PY                                            22

SEQ ID NO: 22           moltype = AA   length = 29
FEATURE                 Location/Qualifiers
REGION                  1..29
                        note = peptide
source                  1..29
                        mol_type = protein
                        organism = synthetic construct
SEQUENCE: 22
ISEYRHYCYS LYGTTLEQQY NKPLCDLLI                                     29

SEQ ID NO: 23           moltype = AA   length = 32
FEATURE                 Location/Qualifiers
REGION                  1..32
                        note = peptide
source                  1..32
                        mol_type = protein
                        organism = synthetic construct
SEQUENCE: 23
IRCINCQKPL CPEEKQRHLD KKQRFHNIRG RW                                 32

SEQ ID NO: 24           moltype = AA   length = 23
FEATURE                 Location/Qualifiers
REGION                  1..23
                        note = peptide
source                  1..23
                        mol_type = protein
                        organism = synthetic construct
SEQUENCE: 24
GDTPTLHEYM LDLQPETTDL YCY                                           23

SEQ ID NO: 25           moltype = AA   length = 17
FEATURE                 Location/Qualifiers
REGION                  1..17
                        note = peptide
source                  1..17
                        mol_type = protein
                        organism = synthetic construct
SEQUENCE: 25
QAEPDRAHYN IVTFCCK                                                  17

SEQ ID NO: 26           moltype = AA   length = 19
FEATURE                 Location/Qualifiers
REGION                  1..19
                        note = peptide
source                  1..19
                        mol_type = protein
                        organism = synthetic construct
SEQUENCE: 26
LEDLLMGTLG IVCPICSQK                                                19

SEQ ID NO: 27           moltype = AA   length = 8
FEATURE                 Location/Qualifiers
REGION                  1..8
                        note = peptide
source                  1..8
                        mol_type = protein
                        organism = synthetic construct
SEQUENCE: 27
RPRKLPQL                                                            8

SEQ ID NO: 28           moltype = AA   length = 9
FEATURE                 Location/Qualifiers
REGION                  1..9
                        note = peptide
source                  1..9
```

```
SEQUENCE: 28
KLPQLCTEL                                                                    9

SEQ ID NO: 29          moltype = AA  length = 8
FEATURE                Location/Qualifiers
REGION                 1..8
                       note = peptide
source                 1..8
                       mol_type = protein
                       organism = synthetic construct
SEQUENCE: 29
LPQLCTEL                                                                     8

SEQ ID NO: 30          moltype = AA  length = 10
FEATURE                Location/Qualifiers
REGION                 1..10
                       note = peptide
source                 1..10
                       mol_type = protein
                       organism = synthetic construct
SEQUENCE: 30
QLCTELQTTI                                                                  10

SEQ ID NO: 31          moltype = AA  length = 10
FEATURE                Location/Qualifiers
REGION                 1..10
                       note = peptide
source                 1..10
                       mol_type = protein
                       organism = synthetic construct
SEQUENCE: 31
TELQTTIHDI                                                                  10

SEQ ID NO: 32          moltype = AA  length = 10
FEATURE                Location/Qualifiers
REGION                 1..10
                       note = peptide
source                 1..10
                       mol_type = protein
                       organism = synthetic construct
SEQUENCE: 32
TIHDIILRCV                                                                  10

SEQ ID NO: 33          moltype = AA  length = 9
FEATURE                Location/Qualifiers
REGION                 1..9
                       note = peptide
source                 1..9
                       mol_type = protein
                       organism = synthetic construct
SEQUENCE: 33
IILECVYCK                                                                    9

SEQ ID NO: 34          moltype = AA  length = 10
FEATURE                Location/Qualifiers
REGION                 1..10
                       note = peptide
source                 1..10
                       mol_type = protein
                       organism = synthetic construct
SEQUENCE: 34
LECVYCKQQL                                                                  10

SEQ ID NO: 35          moltype = AA  length = 8
FEATURE                Location/Qualifiers
REGION                 1..8
                       note = peptide
source                 1..8
                       mol_type = protein
                       organism = synthetic construct
SEQUENCE: 35
CVYCKQQL                                                                     8

SEQ ID NO: 36          moltype = AA  length = 10
FEATURE                Location/Qualifiers
REGION                 1..10
                       note = peptide
```

```
source                   1..10
                         mol_type = protein
                         organism = synthetic construct
SEQUENCE: 36
RREVYDFAFR                                                                10

SEQ ID NO: 37            moltype = AA   length = 9
FEATURE                  Location/Qualifiers
REGION                   1..9
                         note = peptide
source                   1..9
                         mol_type = protein
                         organism = synthetic construct
SEQUENCE: 37
VYDFAFRDL                                                                 9

SEQ ID NO: 38            moltype = AA   length = 8
FEATURE                  Location/Qualifiers
REGION                   1..8
                         note = peptide
source                   1..8
                         mol_type = protein
                         organism = synthetic construct
SEQUENCE: 38
YDFAFRDL                                                                  8

SEQ ID NO: 39            moltype = AA   length = 9
FEATURE                  Location/Qualifiers
REGION                   1..9
                         note = peptide
source                   1..9
                         mol_type = protein
                         organism = synthetic construct
SEQUENCE: 39
FAFRDLCIV                                                                 9

SEQ ID NO: 40            moltype = AA   length = 9
FEATURE                  Location/Qualifiers
REGION                   1..9
                         note = peptide
source                   1..9
                         mol_type = protein
                         organism = synthetic construct
SEQUENCE: 40
FRDLCIVYR                                                                 9

SEQ ID NO: 41            moltype = AA   length = 9
FEATURE                  Location/Qualifiers
REGION                   1..9
                         note = peptide
source                   1..9
                         mol_type = protein
                         organism = synthetic construct
SEQUENCE: 41
IVYRDGNPY                                                                 9

SEQ ID NO: 42            moltype = AA   length = 9
FEATURE                  Location/Qualifiers
REGION                   1..9
                         note = peptide
source                   1..9
                         mol_type = protein
                         organism = synthetic construct
SEQUENCE: 42
ISEYRHYCY                                                                 9

SEQ ID NO: 43            moltype = AA   length = 8
FEATURE                  Location/Qualifiers
REGION                   1..8
                         note = peptide
source                   1..8
                         mol_type = protein
                         organism = synthetic construct
SEQUENCE: 43
SEYRHYCY                                                                  8

SEQ ID NO: 44            moltype = AA   length = 9
FEATURE                  Location/Qualifiers
REGION                   1..9
```

```
                         note         = peptide
source                   1..9
                         mol_type     = protein
                         organism     = synthetic construct
SEQUENCE: 44
CYSLYGTTL                                                                     9

SEQ ID NO: 45            moltype = AA   length = 8
FEATURE                  Location/Qualifiers
REGION                   1..8
                         note         = peptide
source                   1..8
                         mol_type     = protein
                         organism     = synthetic construct
SEQUENCE: 45
TLEQQYNK                                                                      8

SEQ ID NO: 46            moltype = AA   length = 9
FEATURE                  Location/Qualifiers
REGION                   1..9
                         note         = peptide
source                   1..9
                         mol_type     = protein
                         organism     = synthetic construct
SEQUENCE: 46
LEQQYNKPL                                                                     9

SEQ ID NO: 47            moltype = AA   length = 8
FEATURE                  Location/Qualifiers
REGION                   1..8
                         note         = peptide
source                   1..8
                         mol_type     = protein
                         organism     = synthetic construct
SEQUENCE: 47
KPLCDLLI                                                                      8

SEQ ID NO: 48            moltype = AA   length = 9
FEATURE                  Location/Qualifiers
REGION                   1..9
                         note         = peptide
source                   1..9
                         mol_type     = protein
                         organism     = synthetic construct
SEQUENCE: 48
CPEEKQRHL                                                                     9

SEQ ID NO: 49            moltype = AA   length = 8
FEATURE                  Location/Qualifiers
REGION                   1..8
                         note         = peptide
source                   1..8
                         mol_type     = protein
                         organism     = synthetic construct
SEQUENCE: 49
PEEKQRHL                                                                      8

SEQ ID NO: 50            moltype = AA   length = 7
FEATURE                  Location/Qualifiers
REGION                   1..7
                         note         = peptide
source                   1..7
                         mol_type     = protein
                         organism     = synthetic construct
SEQUENCE: 50
DKKQRHM                                                                       7

SEQ ID NO: 51            moltype = AA   length = 9
FEATURE                  Location/Qualifiers
REGION                   1..9
                         note         = peptide
source                   1..9
                         mol_type     = protein
                         organism     = synthetic construct
SEQUENCE: 51
KKQRFHNIR                                                                     9

SEQ ID NO: 52            moltype = AA   length = 10
FEATURE                  Location/Qualifiers
```

-continued

```
REGION                  1..10
                        note = peptide
source                  1..10
                        mol_type = protein
                        organism = synthetic construct
SEQUENCE: 52
QRFHNIRGRW                                                                    10

SEQ ID NO: 53           moltype = AA  length = 9
FEATURE                 Location/Qualifiers
REGION                  1..9
                        note = peptide
source                  1..9
                        mol_type = protein
                        organism = synthetic construct
SEQUENCE: 53
RFHNIRGRW                                                                      9

SEQ ID NO: 54           moltype = AA  length = 9
FEATURE                 Location/Qualifiers
REGION                  1..9
                        note = peptide
source                  1..9
                        mol_type = protein
                        organism = synthetic construct
SEQUENCE: 54
GDTPTLHEY                                                                      9

SEQ ID NO: 55           moltype = AA  length = 9
FEATURE                 Location/Qualifiers
REGION                  1..9
                        note = peptide
source                  1..9
                        mol_type = protein
                        organism = synthetic construct
SEQUENCE: 55
TPTLHEYML                                                                      9

SEQ ID NO: 56           moltype = AA  length = 10
FEATURE                 Location/Qualifiers
REGION                  1..10
                        note = peptide
source                  1..10
                        mol_type = protein
                        organism = synthetic construct
SEQUENCE: 56
YMLDLQPETT                                                                    10

SEQ ID NO: 57           moltype = AA  length = 9
FEATURE                 Location/Qualifiers
REGION                  1..9
                        note = peptide
source                  1..9
                        mol_type = protein
                        organism = synthetic construct
SEQUENCE: 57
LQPETTDLY                                                                      9

SEQ ID NO: 58           moltype = AA  length = 10
FEATURE                 Location/Qualifiers
REGION                  1..10
                        note = peptide
source                  1..10
                        mol_type = protein
                        organism = synthetic construct
SEQUENCE: 58
QPETTDLYCY                                                                    10

SEQ ID NO: 59           moltype = AA  length = 9
FEATURE                 Location/Qualifiers
REGION                  1..9
                        note = peptide
source                  1..9
                        mol_type = protein
                        organism = synthetic construct
SEQUENCE: 59
QAEPDRAHY                                                                      9

SEQ ID NO: 60           moltype = AA  length = 8
```

```
                          -continued

FEATURE           Location/Qualifiers
REGION            1..8
                  note = peptide
source            1..8
                  mol_type = protein
                  organism = synthetic construct
SEQUENCE: 60
AEPDRAHY                                                                    8

SEQ ID NO: 61     moltype = AA  length = 10
FEATURE           Location/Qualifiers
REGION            1..10
                  note = peptide
source            1..10
                  mol_type = protein
                  organism = synthetic construct
SEQUENCE: 61
EPDRAHYNIV                                                                 10

SEQ ID NO: 62     moltype = AA  length = 7
FEATURE           Location/Qualifiers
REGION            1..7
                  note = peptide
source            1..7
                  mol_type = protein
                  organism = synthetic construct
SEQUENCE: 62
MVTFCCK                                                                     7

SEQ ID NO: 63     moltype = AA  length = 9
FEATURE           Location/Qualifiers
REGION            1..9
                  note = peptide
source            1..9
                  mol_type = protein
                  organism = synthetic construct
SEQUENCE: 63
LEDLLMGTL                                                                   9

SEQ ID NO: 64     moltype = AA  length = 9
FEATURE           Location/Qualifiers
REGION            1..9
                  note = peptide
source            1..9
                  mol_type = protein
                  organism = synthetic construct
SEQUENCE: 64
LLMGTLGIV                                                                   9

SEQ ID NO: 65     moltype = AA  length = 8
FEATURE           Location/Qualifiers
REGION            1..8
                  note = peptide
source            1..8
                  mol_type = protein
                  organism = synthetic construct
SEQUENCE: 65
TLGIVCPI                                                                    8

SEQ ID NO: 66     moltype = AA  length = 9
FEATURE           Location/Qualifiers
REGION            1..9
                  note = peptide
source            1..9
                  mol_type = protein
                  organism = synthetic construct
SEQUENCE: 66
IVCPICSQK                                                                   9

SEQ ID NO: 67     moltype = AA  length = 9
FEATURE           Location/Qualifiers
REGION            1..9
                  note = peptide
source            1..9
                  mol_type = protein
                  organism = synthetic construct
SEQUENCE: 67
RAHYNIVTF                                                                   9
```

-continued

```
SEQ ID NO: 68              moltype = AA  length = 90
FEATURE                    Location/Qualifiers
REGION                     1..90
                           note = peptide
source                     1..90
                           mol_type = protein
                           organism = synthetic construct
SEQUENCE: 68
DYWKHMRLEC AIYYKAREMG FKHINHQVVP TLAVSKNKAL QAIELQLTLE TIYNSQYSNE    60
KWTLQDVSLE VYLTAPTGCI KKHGYTVEVQ                                     90

SEQ ID NO: 69              moltype = AA  length = 45
FEATURE                    Location/Qualifiers
REGION                     1..45
                           note = peptide
source                     1..45
                           mol_type = protein
                           organism = synthetic construct
SEQUENCE: 69
QVDYYGLYYV HEGIRTYFVQ FKDDAEKYSK NKVWEVHAGG QVILC                    45

SEQ ID NO: 70              moltype = AA  length = 95
FEATURE                    Location/Qualifiers
REGION                     1..95
                           note = peptide
source                     1..95
                           mol_type = protein
                           organism = synthetic construct
SEQUENCE: 70
FNSSHKGRIN CNSNTTPIVH LKGDANTLKC LRYRFKKHCT LYTAVSSTWH WTGHNVKHKS    60
AIVTLTYDSE WQRDQFLSQV KIPKTITVST GFMSI                               95

SEQ ID NO: 71              moltype = AA  length = 78
FEATURE                    Location/Qualifiers
REGION                     1..78
                           note = peptide
source                     1..78
                           mol_type = protein
                           organism = synthetic construct
SEQUENCE: 71
SEYRHYCYSL YGTTLEQQYN KPLCDLLIRC INCQKPLCPE EKQRHLDKKQ RFHNIRGRWT    60
GRCMSCCRSS RTRRETQL                                                  78

SEQ ID NO: 72              moltype = AA  length = 47
FEATURE                    Location/Qualifiers
REGION                     1..47
                           note = peptide
source                     1..47
                           mol_type = protein
                           organism = synthetic construct
SEQUENCE: 72
SSEEEDEIDG PAGQAEPDRA HYNIVTFCCK CDSTLRLCVQ STHVDIR                  47

SEQ ID NO: 73              moltype = AA  length = 15
FEATURE                    Location/Qualifiers
REGION                     1..15
                           note = peptide
source                     1..15
                           mol_type = protein
                           organism = synthetic construct
SEQUENCE: 73
KIPKTITVST GFMSI                                                     15

SEQ ID NO: 74              moltype = AA  length = 15
FEATURE                    Location/Qualifiers
REGION                     1..15
                           note = peptide
source                     1..15
                           mol_type = protein
                           organism = synthetic construct
SEQUENCE: 74
SSTWHWTGHN VKHKS                                                     15

SEQ ID NO: 75              moltype = AA  length = 10
FEATURE                    Location/Qualifiers
REGION                     1..10
                           note = peptide
source                     1..10
                           mol_type = protein
```

```
                                organism = synthetic construct
SEQUENCE: 75
FLSQVKIPKT                                                              10

SEQ ID NO: 76           moltype = AA  length = 20
FEATURE                 Location/Qualifiers
REGION                  1..20
                        note = peptide
source                  1..20
                        mol_type = protein
                        organism = synthetic construct
SEQUENCE: 76
FKHINHQVVP TLAVSKNKAL                                                   20

SEQ ID NO: 77           moltype = AA  length = 16
FEATURE                 Location/Qualifiers
REGION                  1..16
                        note = peptide
source                  1..16
                        mol_type = protein
                        organism = synthetic construct
SEQUENCE: 77
TLAVSKNKAL QAIELQ                                                       16

SEQ ID NO: 78           moltype = AA  length = 15
FEATURE                 Location/Qualifiers
REGION                  1..15
                        note = peptide
source                  1..15
                        mol_type = protein
                        organism = synthetic construct
SEQUENCE: 78
LYTAVSSTWH WTGHN                                                        15

SEQ ID NO: 79           moltype = AA  length = 13
FEATURE                 Location/Qualifiers
REGION                  1..13
                        note = peptide
source                  1..13
                        mol_type = protein
                        organism = synthetic construct
SEQUENCE: 79
AHYNIVTFCC KCD                                                          13

SEQ ID NO: 80           moltype = AA  length = 35
FEATURE                 Location/Qualifiers
REGION                  1..35
                        note = peptide
source                  1..35
                        mol_type = protein
                        organism = synthetic construct
SEQUENCE: 80
GQAEPDRAHY NIVTFCCKCD STLRLCVQST HVDIR                                  35

SEQ ID NO: 81           moltype = AA  length = 16
FEATURE                 Location/Qualifiers
REGION                  1..16
                        note = peptide
source                  1..16
                        mol_type = protein
                        organism = synthetic construct
SEQUENCE: 81
EDEIDGPAGQ AEPDRA                                                       16

SEQ ID NO: 82           moltype = AA  length = 16
FEATURE                 Location/Qualifiers
REGION                  1..16
                        note = peptide
source                  1..16
                        mol_type = protein
                        organism = synthetic construct
SEQUENCE: 82
DKKQRFHNIR GRWTGR                                                       16

SEQ ID NO: 83           moltype = AA  length = 22
FEATURE                 Location/Qualifiers
REGION                  1..22
                        note = peptide
source                  1..22
```

```
                              mol_type = protein
                              organism = synthetic construct
SEQUENCE: 83
DPQERPRKLP QLCTELQTTI HD                                            22

SEQ ID NO: 84            moltype = AA  length = 32
FEATURE                  Location/Qualifiers
REGION                   1..32
                         note = peptide
source                   1..32
                         mol_type = protein
                         organism = synthetic construct
SEQUENCE: 84
CVYCKQQLLR REVYDFAFRD LCIVYRDGNP YA                                 32

SEQ ID NO: 85            moltype = AA  length = 10
FEATURE                  Location/Qualifiers
REGION                   1..10
                         note = peptide
source                   1..10
                         mol_type = protein
                         organism = synthetic construct
SEQUENCE: 85
FAFRDLCIVY                                                          10

SEQ ID NO: 86            moltype = AA  length = 32
FEATURE                  Location/Qualifiers
REGION                   1..32
                         note = peptide
source                   1..32
                         mol_type = protein
                         organism = synthetic construct
SEQUENCE: 86
RDLCIVYRDG NPYAVCDKCL KFYSKISEYR HY                                 32

SEQ ID NO: 87            moltype = AA  length = 22
FEATURE                  Location/Qualifiers
REGION                   1..22
                         note = peptide
source                   1..22
                         mol_type = protein
                         organism = synthetic construct
SEQUENCE: 87
YRDGNPYAVC DKCLKFYSKI SE                                            22

SEQ ID NO: 88            moltype = AA  length = 33
FEATURE                  Location/Qualifiers
REGION                   1..33
                         note = peptide
source                   1..33
                         mol_type = protein
                         organism = synthetic construct
SEQUENCE: 88
CLKFYSKISE YRHYCYSLYG TTLEQQYNKP LCD                                33

SEQ ID NO: 89            moltype = AA  length = 22
FEATURE                  Location/Qualifiers
REGION                   1..22
                         note = peptide
source                   1..22
                         mol_type = protein
                         organism = synthetic construct
SEQUENCE: 89
YGTTLEQQYN KPLCDLLIRC IN                                            22

SEQ ID NO: 90            moltype = AA  length = 22
FEATURE                  Location/Qualifiers
REGION                   1..22
                         note = peptide
source                   1..22
                         mol_type = protein
                         organism = synthetic construct
SEQUENCE: 90
KPLCDLLIRC INCQKPLCPE EK                                            22

SEQ ID NO: 91            moltype = AA  length = 22
FEATURE                  Location/Qualifiers
REGION                   1..22
                         note = peptide
```

```
source                  1..22
                        mol_type = protein
                        organism = synthetic construct
SEQUENCE: 91
EKQRHLDKKQ RFHNIRGRWT GR                                              22

SEQ ID NO: 92           moltype = AA   length = 10
FEATURE                 Location/Qualifiers
REGION                  1..10
                        note = peptide
source                  1..10
                        mol_type = protein
                        organism = synthetic construct
SEQUENCE: 92
KQRFHNIRGR                                                            10

SEQ ID NO: 93           moltype = AA   length = 22
FEATURE                 Location/Qualifiers
REGION                  1..22
                        note = peptide
source                  1..22
                        mol_type = protein
                        organism = synthetic construct
SEQUENCE: 93
DLYCYEQLND SSEEEDEIDG PA                                              22

SEQ ID NO: 94           moltype = AA   length = 22
FEATURE                 Location/Qualifiers
REGION                  1..22
                        note = peptide
source                  1..22
                        mol_type = protein
                        organism = synthetic construct
SEQUENCE: 94
HYNIVTFCCK CDSTLRLCVQ ST                                              22

SEQ ID NO: 95           moltype = AA   length = 11
FEATURE                 Location/Qualifiers
REGION                  1..11
                        note = peptide
source                  1..11
                        mol_type = protein
                        organism = synthetic construct
SEQUENCE: 95
IRTLEDLLMG T                                                          11

SEQ ID NO: 96           moltype = AA   length = 22
FEATURE                 Location/Qualifiers
REGION                  1..22
                        note = peptide
source                  1..22
                        mol_type = protein
                        organism = synthetic construct
SEQUENCE: 96
REHGIQTLNH QVVPAYNISK SK                                              22

SEQ ID NO: 97           moltype = AA   length = 22
FEATURE                 Location/Qualifiers
REGION                  1..22
                        note = peptide
source                  1..22
                        mol_type = protein
                        organism = synthetic construct
SEQUENCE: 97
DKCLKFYSKI SEYRHYCYSL YG                                              22

SEQ ID NO: 98           moltype = AA   length = 32
FEATURE                 Location/Qualifiers
REGION                  1..32
                        note = peptide
source                  1..32
                        mol_type = protein
                        organism = synthetic construct
SEQUENCE: 98
MHGPKATLQD IVLHLEPQNE IPVDLLCHEQ LS                                   32

SEQ ID NO: 99           moltype = AA   length = 16
FEATURE                 Location/Qualifiers
REGION                  1..16
```

```
                        note = peptide
source                  1..16
                        mol_type = protein
                        organism = synthetic construct
SEQUENCE: 99
IPVDLLCHEQ LSDSEE                                                           16

SEQ ID NO: 100          moltype = AA   length = 10
FEATURE                 Location/Qualifiers
REGION                  1..10
                        note = peptide
source                  1..10
                        mol_type = protein
                        organism = synthetic construct
SEQUENCE: 100
QERPRKLPQL                                                                  10

SEQ ID NO: 101          moltype = AA   length = 10
FEATURE                 Location/Qualifiers
REGION                  1..10
                        note = peptide
source                  1..10
                        mol_type = protein
                        organism = synthetic construct
SEQUENCE: 101
TIHDIILECV                                                                  10

SEQ ID NO: 102          moltype = AA   length = 10
FEATURE                 Location/Qualifiers
REGION                  1..10
                        note = peptide
source                  1..10
                        mol_type = protein
                        organism = synthetic construct
SEQUENCE: 102
GRWTGRCMSC                                                                  10

SEQ ID NO: 103          moltype = AA   length = 10
FEATURE                 Location/Qualifiers
REGION                  1..10
                        note = peptide
source                  1..10
                        mol_type = protein
                        organism = synthetic construct
SEQUENCE: 103
SSRTRRETQL                                                                  10

SEQ ID NO: 104          moltype = AA   length = 9
FEATURE                 Location/Qualifiers
REGION                  1..9
                        note = peptide
source                  1..9
                        mol_type = protein
                        organism = synthetic construct
SEQUENCE: 104
IVLHLEPQN                                                                    9

SEQ ID NO: 105          moltype = AA   length = 845
FEATURE                 Location/Qualifiers
source                  1..845
                        mol_type = protein
                        organism = Hepatitis B virus
SEQUENCE: 105
MPLSYQHFRK LLLLDDGTEA GPLEEELPRL ADADLHRRVA EDLNLGNLNV SIPWTHKVGN            60
FTGLYSSTVP IFNPEWQTPS FPKIHLQEDI INRCQQFVGP LTVNEKRRLK LIMPARFYPT           120
HTKYLPLDKG IKPYYPDQVV NHYFQTRHYL HTLWKAGILY KRETTRSASF CGSPYSWEQE           180
LQHGRLVIKT SQRHGDESFC SQSSGILSRS SVGPCIRSQL KQSRLGLQPR QGRLASSQPS           240
RSGSIRAKAH PSTRRYFGVE PSGSGHIDHS VNNSSSCLHQ SAVRKAAYSH LSTSKRQSSS           300
GHAVEFHCLP PNSAGSQSQG SVSSCWWLQF RNSKPCSEYC LSHLVNLRED WGPCDEHGEH           360
HIRIPRTPAR VTGGVFLVDK NPHNTAESRL VVDFSQFSRG ISRVSWPKFA VPNLQSLTNL           420
LSSNLSWLSL DVSAAFYHIP LHPAAMPHLL IGSSGLSRYV ARLSSNSRIN NNQYGTMQNL           480
HDSCSRQLYV SLMLLYKTYG WKLHLYSHPI VLGFRKIPMG VGLSPFLLAQ FTSAICSVVR           540
RAFPHCLAFS YMDDVVLGAK SVQHRESLYT AVTNFLLSLG IHLNPNKTKR WGYSLNFMGY           600
IIGSWGTLPQ DHIVQKIKHC FRKLPVNRPI DWKVCQRIVG LLGFAAPFTQ CGYPALMPLY           660
ACIQAKQAFT FSPTYKAFLS KQYMNLYPVA RQRPGLCQVF ADATPTGWGL AIGHQRMRGT           720
FVAPLPIHTA ELLAACFARS RSGAKLIGTD NSVVLSRKYT SFPWLLGCTA NWILRGTSFV           780
YVPSALNPAD DPSRGRLGLS RPLLRLPFQP TTGRTSLYAV SPSVPSHLPV RVHFASPLHV           840
AWRPP                                                                      845
```

-continued

```
SEQ ID NO: 106          moltype = AA   length = 214
FEATURE                 Location/Qualifiers
source                  1..214
                        mol_type = protein
                        organism = Hepatitis B virus
SEQUENCE: 106
MQLFHLCLII SCTCPTVQAS KLCLGWLWGM DIDPYKEFGA TVELLSFLPS DFFPSVRDLL    60
DTASALYREA LESPEHCSPH HTALRQAILC WGELMTLATW VGNNLEDPAS RDLVVNYVNT   120
NVGLKIRQLL WFHISCLTFG RETVLEYLVS FGVWIRTPPA YRPPNAPILS TLPETTVVRR   180
RDRGRSPRRR TPSPRRRRSP SPRRRRSQSR ESQC                               214

SEQ ID NO: 107          moltype = AA   length = 154
FEATURE                 Location/Qualifiers
source                  1..154
                        mol_type = protein
                        organism = Hepatitis B virus
SEQUENCE: 107
MAARLCCQLD PARDVLCLRP VGAESRGRPL SGPLGALPSP SPSAVPADHG AHLSLRGLPV    60
CAFSSAGPCA LRFTSARRME TTVNAHQILP KVLHKRTLGL SAMSTTDLEA YFKDCVFKDW   120
EELGEEIRLK VFVLGGCRHK LVCSPAPCNF FTSA                               154

SEQ ID NO: 108          moltype = AA   length = 400
FEATURE                 Location/Qualifiers
source                  1..400
                        mol_type = protein
                        organism = Hepatitis B virus
SEQUENCE: 108
MGGWSSKPRK GMGTNLSVPN PLGFFPDHQL DPAFGANSNN PDWDFNPVKD DWPAANQVGV    60
GAFGPRLTPP HGGILGWSPQ AQGILTTVST IPPPASTNRQ SGRQPTPISP PLRDSHPQAM   120
QWNSTAFHQT LQDPRVRGLY LPAGGSSSGT VNPAPNIASH ISSISARTGD PVTNMENITS   180
GFLGPLLVLQ AGFFLLTRIL TIPQSLDSWW TSLNFLGGSP VCLGQNSQSP TSNHSPTSCP   240
PICPGYRWMC LRRFIIFLFI LLLCLIFLLV LLDYQGMLPV CPLIPGSTTT STGPCKTCTT   300
PAQGNSMFPS CCCTKPTDGN CTCIPIPSSW AFAKYLWEWA SVRFSWLSLL VPFVQWFVGL   360
SPTVWLSAIW MMWYWGPSLY SIVSPFIPLL PIFFCLWVYI                         400

SEQ ID NO: 109          moltype = AA   length = 30
FEATURE                 Location/Qualifiers
REGION                  1..30
                        note = peptide
source                  1..30
                        mol_type = protein
                        organism = synthetic construct
SEQUENCE: 109
MPLSYQHFRK LLLLDDGTEA GPLEEELPRL                                     30

SEQ ID NO: 110          moltype = AA   length = 35
FEATURE                 Location/Qualifiers
REGION                  1..35
                        note = peptide
source                  1..35
                        mol_type = protein
                        organism = synthetic construct
SEQUENCE: 110
IPWTHKVGNF TGLYSSTVPI FNPEWQTPSF PKIHL                               35

SEQ ID NO: 111          moltype = AA   length = 33
FEATURE                 Location/Qualifiers
REGION                  1..33
                        note = peptide
source                  1..33
                        mol_type = protein
                        organism = synthetic construct
SEQUENCE: 111
VNEKRRLKLI MPARFYPTHT KYLPLDKGIK PYY                                 33

SEQ ID NO: 112          moltype = AA   length = 33
FEATURE                 Location/Qualifiers
REGION                  1..33
                        note = peptide
source                  1..33
                        mol_type = protein
                        organism = synthetic construct
SEQUENCE: 112
YPTHTKYLPL DKGIKPYYPD QVVNHYFQTR HYL                                 33

SEQ ID NO: 113          moltype = AA   length = 39
FEATURE                 Location/Qualifiers
REGION                  1..39
                        note = peptide
```

```
source                     1..39
                           mol_type = protein
                           organism = synthetic construct
SEQUENCE: 113
VVNHYFQTRH YLHTLWKAGI LYKRETTRSA SFCGSPYSW                              39

SEQ ID NO: 114             moltype = AA  length = 35
FEATURE                    Location/Qualifiers
REGION                     1..35
                           note = peptide
source                     1..35
                           mol_type = protein
                           organism = synthetic construct
SEQUENCE: 114
YFQTRHYLHT LWKAGILYKR ETTRSASFCG SPYSW                                  35

SEQ ID NO: 115             moltype = AA  length = 34
FEATURE                    Location/Qualifiers
REGION                     1..34
                           note = peptide
source                     1..34
                           mol_type = protein
                           organism = synthetic construct
SEQUENCE: 115
DQVVNHYFQT RHYLHTLWKA GILYKRETTR SASF                                   34

SEQ ID NO: 116             moltype = AA  length = 32
FEATURE                    Location/Qualifiers
REGION                     1..32
                           note = peptide
source                     1..32
                           mol_type = protein
                           organism = synthetic construct
SEQUENCE: 116
SQSQGSVSSC WWLQFRNSKP CSEYCLSHLV NL                                     32

SEQ ID NO: 117             moltype = AA  length = 33
FEATURE                    Location/Qualifiers
REGION                     1..33
                           note = peptide
source                     1..33
                           mol_type = protein
                           organism = synthetic construct
SEQUENCE: 117
TAESRLVVDF SQFSRGISRV SWPKFAVPNL QSL                                    33

SEQ ID NO: 118             moltype = AA  length = 38
FEATURE                    Location/Qualifiers
REGION                     1..38
                           note = peptide
source                     1..38
                           mol_type = protein
                           organism = synthetic construct
SEQUENCE: 118
NLLSSNLSWL SLDVSAAFYH IPLHPAAMPH LLIGSSGL                               38

SEQ ID NO: 119             moltype = AA  length = 38
FEATURE                    Location/Qualifiers
REGION                     1..38
                           note = peptide
source                     1..38
                           mol_type = protein
                           organism = synthetic construct
SEQUENCE: 119
SSNLSWLSLD VSAAFYHIPL HPAAMPHLLI GSSGLSRY                               38

SEQ ID NO: 120             moltype = AA  length = 33
FEATURE                    Location/Qualifiers
REGION                     1..33
                           note = peptide
source                     1..33
                           mol_type = protein
                           organism = synthetic construct
SEQUENCE: 120
WLSLDVSAAF YHIPLHPAAM PHLLIGSSGL SRY                                    33

SEQ ID NO: 121             moltype = AA  length = 34
FEATURE                    Location/Qualifiers
REGION                     1..34
```

```
                              note = peptide
source                        1..34
                              mol_type = protein
                              organism = synthetic construct
SEQUENCE: 121
HDSCSRQLYV SLMLLYKTYG WKLHLYSHPI VLGF                              34

SEQ ID NO: 122         moltype = AA  length = 36
FEATURE                Location/Qualifiers
REGION                 1..36
                       note = peptide
source                 1..36
                       mol_type = protein
                       organism = synthetic construct
SEQUENCE: 122
SPFLLAQFTS AICSVVRRAF PHCLAFSYMD DVVLGA                            36

SEQ ID NO: 123         moltype = AA  length = 34
FEATURE                Location/Qualifiers
REGION                 1..34
                       note = peptide
source                 1..34
                       mol_type = protein
                       organism = synthetic construct
SEQUENCE: 123
FLLAQFTSAI CSVVRRAFPH CLAFSYMDDV VLGA                              34

SEQ ID NO: 124         moltype = AA  length = 34
FEATURE                Location/Qualifiers
REGION                 1..34
                       note = peptide
source                 1..34
                       mol_type = protein
                       organism = synthetic construct
SEQUENCE: 124
RESLYTAVTN FLLSLGIHLN PNKTKRWGYS LNFM                              34

SEQ ID NO: 125         moltype = AA  length = 34
FEATURE                Location/Qualifiers
REGION                 1..34
                       note = peptide
source                 1..34
                       mol_type = protein
                       organism = synthetic construct
SEQUENCE: 125
NPNKTKRWGY SLNFMGYIIG SWGTLPQDHI VQKI                              34

SEQ ID NO: 126         moltype = AA  length = 39
FEATURE                Location/Qualifiers
REGION                 1..39
                       note = peptide
source                 1..39
                       mol_type = protein
                       organism = synthetic construct
SEQUENCE: 126
YPALMPLYAC IQAKQAFTFS PTYKAFLSKQ YMNLYPVAR                         39

SEQ ID NO: 127         moltype = AA  length = 35
FEATURE                Location/Qualifiers
REGION                 1..35
                       note = peptide
source                 1..35
                       mol_type = protein
                       organism = synthetic construct
SEQUENCE: 127
MPLYACIQAK QAFTFSPTYK AFLSKQYMNL YPVAR                             35

SEQ ID NO: 128         moltype = AA  length = 32
FEATURE                Location/Qualifiers
REGION                 1..32
                       note = peptide
source                 1..32
                       mol_type = protein
                       organism = synthetic construct
SEQUENCE: 128
QRMRGTFVAP LPIHTAELLA ACFARSRSGA KL                                32

SEQ ID NO: 129         moltype = AA  length = 38
FEATURE                Location/Qualifiers
```

```
REGION                          1..38
                                note = peptide
source                          1..38
                                mol_type = protein
                                organism = synthetic construct
SEQUENCE: 129
VLSRKYTSFP WLLGCTANWI LRGTSFVYVP SALNPADD                              38

SEQ ID NO: 130                  moltype = AA  length = 36
FEATURE                         Location/Qualifiers
REGION                          1..36
                                note = peptide
source                          1..36
                                mol_type = protein
                                organism = synthetic construct
SEQUENCE: 130
RKYTSFPWLL GCTANWILRG TSFVYVPSAL NPADDP                                36

SEQ ID NO: 131                  moltype = AA  length = 36
FEATURE                         Location/Qualifiers
REGION                          1..36
                                note = peptide
source                          1..36
                                mol_type = protein
                                organism = synthetic construct
SEQUENCE: 131
VLSRKYTSFP WLLGCTANWI LRGTSFVYVP SALNPA                                36

SEQ ID NO: 132                  moltype = AA  length = 35
FEATURE                         Location/Qualifiers
REGION                          1..35
                                note = peptide
source                          1..35
                                mol_type = protein
                                organism = synthetic construct
SEQUENCE: 132
DPASRDLVVN YVNTNVGLKI RQLLWFHISC LTFGR                                 35

SEQ ID NO: 133                  moltype = AA  length = 34
FEATURE                         Location/Qualifiers
REGION                          1..34
                                note = peptide
source                          1..34
                                mol_type = protein
                                organism = synthetic construct
SEQUENCE: 133
CLTFGRETVL EYLVSFGVWI RTPPAYRPPN APIL                                  34

SEQ ID NO: 134                  moltype = AA  length = 33
FEATURE                         Location/Qualifiers
REGION                          1..33
                                note = peptide
source                          1..33
                                mol_type = protein
                                organism = synthetic construct
SEQUENCE: 134
ALPSPSPSAV PADHGAHLSL RGLPVCAFSS AGP                                   33

SEQ ID NO: 135                  moltype = AA  length = 35
FEATURE                         Location/Qualifiers
REGION                          1..35
                                note = peptide
source                          1..35
                                mol_type = protein
                                organism = synthetic construct
SEQUENCE: 135
CAFSSAGPCA LRFTSARRME TTVNAHQILP KVLHK                                 35

SEQ ID NO: 136                  moltype = AA  length = 35
FEATURE                         Location/Qualifiers
REGION                          1..35
                                note = peptide
source                          1..35
                                mol_type = protein
                                organism = synthetic construct
SEQUENCE: 136
HQILPKVLHK RTLGLSAMST TDLEAYFKDC VFKDW                                 35

SEQ ID NO: 137                  moltype = AA  length = 34
```

```
FEATURE                 Location/Qualifiers
REGION                  1..34
                        note = peptide
source                  1..34
                        mol_type = protein
                        organism = synthetic construct
SEQUENCE: 137
LEAYFKDCVF KDWEELGEEI RLKVFVLGGC RHKL                               34

SEQ ID NO: 138          moltype = AA  length = 36
FEATURE                 Location/Qualifiers
REGION                  1..36
                        note = peptide
source                  1..36
                        mol_type = protein
                        organism = synthetic construct
SEQUENCE: 138
MENITSGFLG PLLVLQAGFF LLTRILTIPQ SLDSWW                             36

SEQ ID NO: 139          moltype = AA  length = 36
FEATURE                 Location/Qualifiers
REGION                  1..36
                        note = peptide
source                  1..36
                        mol_type = protein
                        organism = synthetic construct
SEQUENCE: 139
CPPICPGYRW MCLRRFIIFL FILLLCLIFL LVLLDY                             36

SEQ ID NO: 140          moltype = AA  length = 36
FEATURE                 Location/Qualifiers
REGION                  1..36
                        note = peptide
source                  1..36
                        mol_type = protein
                        organism = synthetic construct
SEQUENCE: 140
CIPIPSSWAF AKYLWEWASV RFSWLSLLVP FVQWFV                             36

SEQ ID NO: 141          moltype = AA  length = 32
FEATURE                 Location/Qualifiers
REGION                  1..32
                        note = peptide
source                  1..32
                        mol_type = protein
                        organism = synthetic construct
SEQUENCE: 141
PSSWAFAKYL WEWASVRFSW LSLLVPFVQW FV                                 32

SEQ ID NO: 142          moltype = AA  length = 31
FEATURE                 Location/Qualifiers
REGION                  1..31
                        note = peptide
source                  1..31
                        mol_type = protein
                        organism = synthetic construct
SEQUENCE: 142
SSWAFAKYLW EWASVRFSWL SLLVPFVQWF V                                  31

SEQ ID NO: 143          moltype = AA  length = 36
FEATURE                 Location/Qualifiers
REGION                  1..36
                        note = peptide
source                  1..36
                        mol_type = protein
                        organism = synthetic construct
SEQUENCE: 143
WLSAIWMMWY WGPSLYSIVS PFIPLLPIFF CLWVYI                             36

SEQ ID NO: 144          moltype = AA  length = 30
FEATURE                 Location/Qualifiers
REGION                  1..30
                        note = peptide
source                  1..30
                        mol_type = protein
                        organism = synthetic construct
SEQUENCE: 144
MMWYWGPSLY SIVSPFIPLL PIFFCLWVYI                                    30
```

-continued

```
SEQ ID NO: 145          moltype = AA  length = 31
FEATURE                 Location/Qualifiers
REGION                  1..31
                        note = peptide
source                  1..31
                        mol_type = protein
                        organism = synthetic construct
SEQUENCE: 145
WMMWYWGPSL YSIVSPFIPL LPIFFCLWVY I                                  31

SEQ ID NO: 146          moltype = AA  length = 37
FEATURE                 Location/Qualifiers
REGION                  1..37
                        note = peptide
source                  1..37
                        mol_type = protein
                        organism = synthetic construct
SEQUENCE: 146
MQLFHLCLII SCTCPTVQAS KLCLGWLWGM DIDPYKE                            37

SEQ ID NO: 147          moltype = AA  length = 509
FEATURE                 Location/Qualifiers
source                  1..509
                        mol_type = protein
                        organism = Homo sapiens
SEQUENCE: 147
MERRRLWGSI QSRYISMSVW TSPRRLVELA GQSLLKDEAL AIAALELLPR ELFPPLFMAA   60
FDGRHSQTLK AMVQAWPFTC LPLGVLMKGQ HLHLETFKAV LDGLDVLLAQ EVRPRRWKLQ  120
VLDLRKNSHQ DFWTVWSGNR ASLYSFPEPE AAQPMTKKRK VDGLSTEAEQ PFIPVEVLVD  180
LFLKEGACDE LFSYLIEKVK RKKNVLRLCC KKLKIFAMPM QDIKMILKMV QLDSIEDLEV  240
TCTWKLPTLA KFSPYLGQMI NLRRLLLSHI HASSYISPEK EEQYIAQFTS QFLSLQCLQA  300
LYVDSLFFLR GRLDQLLRHV MNPLETLSIT NCRLSEGDVM HLSQSPSVSQ LSVLSLSGVM  360
LTDVSPEPLQ ALLERASATL QDLVFDECGI TDDQLLALLP SLSHCSQLTT LSFYGNSISI  420
SALQSLLQHL IGLSNLTHVL YPVPLESYED IHGTLHLERL AYLHARLREL LCELGRPSMV  480
WLSANPCPHC GDRTFYDPEP ILCPCFMPN                                   509

SEQ ID NO: 148          moltype = AA  length = 33
FEATURE                 Location/Qualifiers
REGION                  1..33
                        note = peptide
source                  1..33
                        mol_type = protein
                        organism = synthetic construct
SEQUENCE: 148
MERRRLWGSI QSRYISMSVW TSPRRLVELA GQS                                33

SEQ ID NO: 149          moltype = AA  length = 35
FEATURE                 Location/Qualifiers
REGION                  1..35
                        note = peptide
source                  1..35
                        mol_type = protein
                        organism = synthetic construct
SEQUENCE: 149
VWTSPRRLVE LAGQSLLKDE ALAIAALELL PRELF                              35

SEQ ID NO: 150          moltype = AA  length = 40
FEATURE                 Location/Qualifiers
REGION                  1..40
                        note = peptide
source                  1..40
                        mol_type = protein
                        organism = synthetic construct
SEQUENCE: 150
PEPTIDELLP RELFPPLFMA AFDGRHSQTL KAMVQAWPFT                         40

SEQ ID NO: 151          moltype = AA  length = 33
FEATURE                 Location/Qualifiers
REGION                  1..33
                        note = peptide
source                  1..33
                        mol_type = protein
                        organism = synthetic construct
SEQUENCE: 151
LKAMVQAWPF TCLPLGVLMK GQHLHLETFK AVL                                33

SEQ ID NO: 152          moltype = AA  length = 35
FEATURE                 Location/Qualifiers
REGION                  1..35
```

-continued

```
                        note = peptide
source                  1..35
                        mol_type = protein
                        organism = synthetic construct
SEQUENCE: 152
CLPLGVLMKG QHLHLETFKA VLDGLDVLLA QEVRP                           35

SEQ ID NO: 153          moltype = AA  length = 33
FEATURE                 Location/Qualifiers
REGION                  1..33
                        note = peptide
source                  1..33
                        mol_type = protein
                        organism = synthetic construct
SEQUENCE: 153
LETFKAVLDG LDVLLAQEVR PRRWKLQVLD LRK                             33

SEQ ID NO: 154          moltype = AA  length = 33
FEATURE                 Location/Qualifiers
REGION                  1..33
                        note = peptide
source                  1..33
                        mol_type = protein
                        organism = synthetic construct
SEQUENCE: 154
VRPRRWKLQV LDLRKNSHQD FWTVWSGNRA SLY                             33

SEQ ID NO: 155          moltype = AA  length = 34
FEATURE                 Location/Qualifiers
REGION                  1..34
                        note = peptide
source                  1..34
                        mol_type = protein
                        organism = synthetic construct
SEQUENCE: 155
WTVWSGNRAS LYSFPEPEAA QPMTKKRKVD GLST                            34

SEQ ID NO: 156          moltype = AA  length = 35
FEATURE                 Location/Qualifiers
REGION                  1..35
                        note = peptide
source                  1..35
                        mol_type = protein
                        organism = synthetic construct
SEQUENCE: 156
IPVEVLVDLF LKEGACDELF SYLIEKVKRK KNVLR                           35

SEQ ID NO: 157          moltype = AA  length = 34
FEATURE                 Location/Qualifiers
REGION                  1..34
                        note = peptide
source                  1..34
                        mol_type = protein
                        organism = synthetic construct
SEQUENCE: 157
ELFSYLIEKV KRKKNVLRLC CKKLKIFAMP MQDI                            34

SEQ ID NO: 158          moltype = AA  length = 35
FEATURE                 Location/Qualifiers
REGION                  1..35
                        note = peptide
source                  1..35
                        mol_type = protein
                        organism = synthetic construct
SEQUENCE: 158
SIEDLEVTCT WKLPTLAKFS PYLGQMINLR RLLLS                           35

SEQ ID NO: 159          moltype = AA  length = 33
FEATURE                 Location/Qualifiers
REGION                  1..33
                        note = peptide
source                  1..33
                        mol_type = protein
                        organism = synthetic construct
SEQUENCE: 159
PTLAKFSPYL GQMINLRRLL LSHIHASSYI SPE                             33

SEQ ID NO: 160          moltype = AA  length = 33
FEATURE                 Location/Qualifiers
```

```
REGION                       1..33
                             note = peptide
source                       1..33
                             mol_type = protein
                             organism = synthetic construct
SEQUENCE: 160
LRRLLLSHIH ASSYISPEKE EQYIAQFTSQ FLS                                  33

SEQ ID NO: 161               moltype = AA  length = 33
FEATURE                      Location/Qualifiers
REGION                       1..33
                             note = peptide
source                       1..33
                             mol_type = protein
                             organism = synthetic construct
SEQUENCE: 161
YIAQFTSQFL SLQCLQALYV DSLFFLRGRL DQL                                  33

SEQ ID NO: 162               moltype = AA  length = 33
FEATURE                      Location/Qualifiers
REGION                       1..33
                             note = peptide
source                       1..33
                             mol_type = protein
                             organism = synthetic construct
SEQUENCE: 162
LQCLQALYVD SLFFLRGRLD QLLRHVMNPL ETL                                  33

SEQ ID NO: 163               moltype = AA  length = 35
FEATURE                      Location/Qualifiers
REGION                       1..35
                             note = peptide
source                       1..35
                             mol_type = protein
                             organism = synthetic construct
SEQUENCE: 163
VLSLSGVMLT DVSPEPLQAL LERASATLQD LVFDE                                35

SEQ ID NO: 164               moltype = AA  length = 33
FEATURE                      Location/Qualifiers
REGION                       1..33
                             note = peptide
source                       1..33
                             mol_type = protein
                             organism = synthetic construct
SEQUENCE: 164
LPSLSHCSQL TTLSFYGNSI SISALQSLLQ HLI                                  33

SEQ ID NO: 165               moltype = AA  length = 34
FEATURE                      Location/Qualifiers
REGION                       1..34
                             note = peptide
source                       1..34
                             mol_type = protein
                             organism = synthetic construct
SEQUENCE: 165
SISISALQSL LQHLIGLSNL THVLYPVPLE SYED                                 34

SEQ ID NO: 166               moltype = AA  length = 34
FEATURE                      Location/Qualifiers
REGION                       1..34
                             note = peptide
source                       1..34
                             mol_type = protein
                             organism = synthetic construct
SEQUENCE: 166
SYEDIHGTLH LERLAYLHAR LRELLCELGR PSMV                                 34

SEQ ID NO: 167               moltype = AA  length = 33
FEATURE                      Location/Qualifiers
REGION                       1..33
                             note = peptide
source                       1..33
                             mol_type = protein
                             organism = synthetic construct
SEQUENCE: 167
PSMVWLSANP CPHCGDRTFY DPEPILCPCF MPN                                  33

SEQ ID NO: 168               moltype = AA  length = 27
```

```
                        -continued

FEATURE                 Location/Qualifiers
REGION                  1..27
                        note = peptide
source                  1..27
                        mol_type = protein
                        organism = synthetic construct
SEQUENCE: 168
MERRRLWGSI QSRYISMSVW TSPRRLV                                        27

SEQ ID NO: 169          moltype = AA  length = 27
FEATURE                 Location/Qualifiers
REGION                  1..27
                        note = peptide
source                  1..27
                        mol_type = protein
                        organism = synthetic construct
SEQUENCE: 169
VWTSPRRLVE LAGQSLLKDE ALAIAAL                                        27

SEQ ID NO: 170          moltype = AA  length = 22
FEATURE                 Location/Qualifiers
REGION                  1..22
                        note = peptide
source                  1..22
                        mol_type = protein
                        organism = synthetic construct
SEQUENCE: 170
LPRELFPPLF MAAFDGRHSQ TL                                             22

SEQ ID NO: 171          moltype = AA  length = 27
FEATURE                 Location/Qualifiers
REGION                  1..27
                        note = peptide
source                  1..27
                        mol_type = protein
                        organism = synthetic construct
SEQUENCE: 171
FPPLFMAAFD GRHSQTLKAM VQAWPFT                                        27

SEQ ID NO: 172          moltype = AA  length = 26
FEATURE                 Location/Qualifiers
REGION                  1..26
                        note = peptide
source                  1..26
                        mol_type = protein
                        organism = synthetic construct
SEQUENCE: 172
KAMVQAWPFT CLPLGVLMKG QHLHLE                                         26

SEQ ID NO: 173          moltype = AA  length = 27
FEATURE                 Location/Qualifiers
REGION                  1..27
                        note = peptide
source                  1..27
                        mol_type = protein
                        organism = synthetic construct
SEQUENCE: 173
GVLMKGQHLH LETFKAVLDG LDVLLAQ                                        27

SEQ ID NO: 174          moltype = AA  length = 27
FEATURE                 Location/Qualifiers
REGION                  1..27
                        note = peptide
source                  1..27
                        mol_type = protein
                        organism = synthetic construct
SEQUENCE: 174
KAVLDGLDVL LAQEVRPRRW KLQVLDL                                        27

SEQ ID NO: 175          moltype = AA  length = 27
FEATURE                 Location/Qualifiers
REGION                  1..27
                        note = peptide
source                  1..27
                        mol_type = protein
                        organism = synthetic construct
SEQUENCE: 175
RWKLQVLDLR KNSHQDFWTV WSGNRAS                                        27
```

```
SEQ ID NO: 176         moltype = AA  length = 27
FEATURE                Location/Qualifiers
REGION                 1..27
                       note = peptide
source                 1..27
                       mol_type = protein
                       organism = synthetic construct
SEQUENCE: 176
WTVWSGNRAS LYSFPEPEAA QPMTKKR                                      27

SEQ ID NO: 177         moltype = AA  length = 27
FEATURE                Location/Qualifiers
REGION                 1..27
                       note = peptide
source                 1..27
                       mol_type = protein
                       organism = synthetic construct
SEQUENCE: 177
LFLKEGACDE LFSYLIEKVK RKKNVLR                                      27

SEQ ID NO: 178         moltype = AA  length = 27
FEATURE                Location/Qualifiers
REGION                 1..27
                       note = peptide
source                 1..27
                       mol_type = protein
                       organism = synthetic construct
SEQUENCE: 178
YLIEKVKRKK NVLRLCCKKL KIFAMPM                                      27

SEQ ID NO: 179         moltype = AA  length = 22
FEATURE                Location/Qualifiers
REGION                 1..22
                       note = peptide
source                 1..22
                       mol_type = protein
                       organism = synthetic construct
SEQUENCE: 179
SIEDLEVTCT WKLPTLAKFS PY                                           22

SEQ ID NO: 180         moltype = AA  length = 27
FEATURE                Location/Qualifiers
REGION                 1..27
                       note = peptide
source                 1..27
                       mol_type = protein
                       organism = synthetic construct
SEQUENCE: 180
PTLAKFSPYL GQMINLRRLL LSHIHAS                                      27

SEQ ID NO: 181         moltype = AA  length = 22
FEATURE                Location/Qualifiers
REGION                 1..22
                       note = peptide
source                 1..22
                       mol_type = protein
                       organism = synthetic construct
SEQUENCE: 181
LGQMINLRRL LLSHIHASSY IS                                           22

SEQ ID NO: 182         moltype = AA  length = 27
FEATURE                Location/Qualifiers
REGION                 1..27
                       note = peptide
source                 1..27
                       mol_type = protein
                       organism = synthetic construct
SEQUENCE: 182
LRRLLLSHIH ASSYISPEKE EQYIAQF                                      27

SEQ ID NO: 183         moltype = AA  length = 27
FEATURE                Location/Qualifiers
REGION                 1..27
                       note = peptide
source                 1..27
                       mol_type = protein
                       organism = synthetic construct
SEQUENCE: 183
SQFLSLQCLQ ALYVDSLFFL RGRLDQL                                      27
```

```
SEQ ID NO: 184          moltype = AA   length = 27
FEATURE                 Location/Qualifiers
REGION                  1..27
                        note = peptide
source                  1..27
                        mol_type = protein
                        organism = synthetic construct
SEQUENCE: 184
ALYVDSLFFL RGRLDQLLRH VMNPLET                                       27

SEQ ID NO: 185          moltype = AA   length = 27
FEATURE                 Location/Qualifiers
REGION                  1..27
                        note = peptide
source                  1..27
                        mol_type = protein
                        organism = synthetic construct
SEQUENCE: 185
VLSLSGVMLT DVSPEPLQAL LERASAT                                       27

SEQ ID NO: 186          moltype = AA   length = 27
FEATURE                 Location/Qualifiers
REGION                  1..27
                        note = peptide
source                  1..27
                        mol_type = protein
                        organism = synthetic construct
SEQUENCE: 186
LPSLSHCSQL TTLSFYGNSI SISALQS                                       27

SEQ ID NO: 187          moltype = AA   length = 27
FEATURE                 Location/Qualifiers
REGION                  1..27
                        note = peptide
source                  1..27
                        mol_type = protein
                        organism = synthetic construct
SEQUENCE: 187
QSLLQHLIGL SNLTHVLYPV PLESYED                                       27

SEQ ID NO: 188          moltype = AA   length = 27
FEATURE                 Location/Qualifiers
REGION                  1..27
                        note = peptide
source                  1..27
                        mol_type = protein
                        organism = synthetic construct
SEQUENCE: 188
SYEDIHGTLH LERLAYLHAR LRELLCE                                       27

SEQ ID NO: 189          moltype = AA   length = 27
FEATURE                 Location/Qualifiers
REGION                  1..27
                        note = peptide
source                  1..27
                        mol_type = protein
                        organism = synthetic construct
SEQUENCE: 189
SANPCPHCGD RTFYDPEPIL CPCFMPN                                       27

SEQ ID NO: 190          moltype = AA   length = 393
FEATURE                 Location/Qualifiers
source                  1..393
                        mol_type = protein
                        organism = Homo sapiens
SEQUENCE: 190
MEEPQSDPSV EPPLSQETFS DLWKLLPENN VLSPLPSQAM DDLMLSPDDI EQWFTEDPGP    60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT EVVRRCPHHE   180
RCSDSDGLAP PQHLIRVEGN LRVEYLDDRN TFRHSVVVPY EPPEVGSDCT TIHYNYMCNS   240
SCMGGMNRRP ILTIITLEDS SGNLLGRNSF EVRVCACPGR DRRTEEENLR KKGEPHHELP   300
PGSTKRALPN NTSSSPQPKK KPLDGEYFTL QIRGRERFEM FRELNEALEL KDAQAGKEPG   360
GSRAHSSHLK SKKGQSTSRH KKLMFKTEGP DSD                                393

SEQ ID NO: 191          moltype = AA   length = 30
FEATURE                 Location/Qualifiers
REGION                  1..30
                        note = peptide
```

```
source                      1..30
                            mol_type = protein
                            organism = synthetic construct
SEQUENCE: 191
APAPSWPLSS SVPSQKTYQG SYGFRLGFLH                                    30

SEQ ID NO: 192              moltype = AA   length = 30
FEATURE                     Location/Qualifiers
REGION                      1..30
                            note = peptide
source                      1..30
                            mol_type = protein
                            organism = synthetic construct
SEQUENCE: 192
TYQGSYGFRL GFLHSGTAKS VTCTYSPALN                                    30

SEQ ID NO: 193              moltype = AA   length = 30
FEATURE                     Location/Qualifiers
REGION                      1..30
                            note = peptide
source                      1..30
                            mol_type = protein
                            organism = synthetic construct
SEQUENCE: 193
PVQLWVDSTP PPGTRVRAMA IYKQSQHMTE                                    30

SEQ ID NO: 194              moltype = AA   length = 30
FEATURE                     Location/Qualifiers
REGION                      1..30
                            note = peptide
source                      1..30
                            mol_type = protein
                            organism = synthetic construct
SEQUENCE: 194
VRAMAIYKQS QHMTEVVRRC PHHERCSDSD                                    30

SEQ ID NO: 195              moltype = AA   length = 30
FEATURE                     Location/Qualifiers
REGION                      1..30
                            note = peptide
source                      1..30
                            mol_type = protein
                            organism = synthetic construct
SEQUENCE: 195
PPQHLIRVEG NLRVEYLDDR NTFRHSVVVP                                    30

SEQ ID NO: 196              moltype = AA   length = 25
FEATURE                     Location/Qualifiers
REGION                      1..25
                            note = peptide
source                      1..25
                            mol_type = protein
                            organism = synthetic construct
SEQUENCE: 196
EVGSDCTTIH YNYMCNSSCM GGMNR                                         25

SEQ ID NO: 197              moltype = AA   length = 30
FEATURE                     Location/Qualifiers
REGION                      1..30
                            note = peptide
source                      1..30
                            mol_type = protein
                            organism = synthetic construct
SEQUENCE: 197
VGSDCTTIHY NYMCNSSCMG GMNRRPILTI                                    30

SEQ ID NO: 198              moltype = AA   length = 30
FEATURE                     Location/Qualifiers
REGION                      1..30
                            note = peptide
source                      1..30
                            mol_type = protein
                            organism = synthetic construct
SEQUENCE: 198
LEDSSGNLLG RNSFEVRVCA CPGRDRRTEE                                    30

SEQ ID NO: 199              moltype = AA   length = 30
FEATURE                     Location/Qualifiers
REGION                      1..30
```

```
                        note = peptide
source                  1..30
                        mol_type = protein
                        organism = synthetic construct
SEQUENCE: 199
RVCACPGRDR RTEEENLRKK GEPHHELPPG                                              30

SEQ ID NO: 200          moltype = AA  length = 30
FEATURE                 Location/Qualifiers
REGION                  1..30
                        note = peptide
source                  1..30
                        mol_type = protein
                        organism = synthetic construct
SEQUENCE: 200
LDDRNTFRHS VVVPYEPPEV GSDCTTIHYN                                              30

SEQ ID NO: 201          moltype = AA  length = 30
FEATURE                 Location/Qualifiers
REGION                  1..30
                        note = peptide
source                  1..30
                        mol_type = protein
                        organism = synthetic construct
SEQUENCE: 201
RRCPHHERCS DSDGLAPPQH LIRVEGNLRV                                              30

SEQ ID NO: 202          moltype = AA  length = 30
FEATURE                 Location/Qualifiers
REGION                  1..30
                        note = peptide
source                  1..30
                        mol_type = protein
                        organism = synthetic construct
SEQUENCE: 202
SCMGGMNRRP ILTIITLEDS SGNLLGRNSF                                              30

SEQ ID NO: 203          moltype = AA  length = 30
FEATURE                 Location/Qualifiers
REGION                  1..30
                        note = peptide
source                  1..30
                        mol_type = protein
                        organism = synthetic construct
SEQUENCE: 203
YSPALNKMFC QLAKTCPVQL WVDSTPPPGT                                              30

SEQ ID NO: 204          moltype = AA  length = 30
FEATURE                 Location/Qualifiers
REGION                  1..30
                        note = peptide
source                  1..30
                        mol_type = protein
                        organism = synthetic construct
SEQUENCE: 204
APPVAPAPAA PTPAAPAPAP SWPLSSSVPS                                              30

SEQ ID NO: 205          moltype = AA  length = 30
FEATURE                 Location/Qualifiers
REGION                  1..30
                        note = peptide
source                  1..30
                        mol_type = protein
                        organism = synthetic construct
SEQUENCE: 205
IYKQSQHMTE VVRRCPHHER CSDSDGLAPP                                              30

SEQ ID NO: 206          moltype = AA  length = 30
FEATURE                 Location/Qualifiers
REGION                  1..30
                        note = peptide
source                  1..30
                        mol_type = protein
                        organism = synthetic construct
SEQUENCE: 206
KRALPNNTSS SPQPKKKPLD GEYFTLQIRG                                              30

SEQ ID NO: 207          moltype = AA  length = 30
FEATURE                 Location/Qualifiers
```

| | | |
|---|---|---|
| REGION | 1..30 | |
| | note = peptide | |
| source | 1..30 | |
| | mol_type = protein | |
| | organism = synthetic construct | |

SEQUENCE: 207
AQAGKEPGGS RAHSSHLKSK KGQSTSRHKK    30

| | | |
|---|---|---|
| SEQ ID NO: 208 | moltype = AA length = 25 | |
| FEATURE | Location/Qualifiers | |
| REGION | 1..25 | |
| | note = peptide | |
| source | 1..25 | |
| | mol_type = protein | |
| | organism = synthetic construct | |

SEQUENCE: 208
LKSKKGQSTS RHKKLMFKTE GPDSD    25

| | | |
|---|---|---|
| SEQ ID NO: 209 | moltype = AA length = 30 | |
| FEATURE | Location/Qualifiers | |
| REGION | 1..30 | |
| | note = peptide | |
| source | 1..30 | |
| | mol_type = protein | |
| | organism = synthetic construct | |

SEQUENCE: 209
LRKKGEPHHE LPPGSTKRAL PNNTSSSPQP    30

| | | |
|---|---|---|
| SEQ ID NO: 210 | moltype = AA length = 30 | |
| FEATURE | Location/Qualifiers | |
| REGION | 1..30 | |
| | note = peptide | |
| source | 1..30 | |
| | mol_type = protein | |
| | organism = synthetic construct | |

SEQUENCE: 210
KPLDGEYFTL QIRGRERFEM FRELNEALEL    30

| | | |
|---|---|---|
| SEQ ID NO: 211 | moltype = AA length = 30 | |
| FEATURE | Location/Qualifiers | |
| REGION | 1..30 | |
| | note = peptide | |
| source | 1..30 | |
| | mol_type = protein | |
| | organism = synthetic construct | |

SEQUENCE: 211
RFEMFRELNE ALELKDAQAG KEPGGSRAHS    30

| | | |
|---|---|---|
| SEQ ID NO: 212 | moltype = AA length = 720 | |
| FEATURE | Location/Qualifiers | |
| source | 1..720 | |
| | mol_type = protein | |
| | organism = Homo sapiens | |

SEQUENCE: 212
MWNLLHETDS AVATARRPRW LCAGALVLAG GFFLLGFLFG WFIKSSNEAT NITPKHNMKA  60
FLDELKAENI KKFLYNFTQI PHLAGTEQNF QLAKQIQSQW KEFGLDSVEL AHYDVLLSYP 120
NKTHPNYISI INEDGNEIFN TSLFEPPPPG YENVSDIVPP FSAFSPQGMP EGDLVYVNYA 180
RTEDFFKLER DMKINCSGKI VIARYGKVFR GNKVKNAQLA GAKGVILYSD PADYFAPGVK 240
SYPDGWNLPG GGVQRGNILN LNGAGDPLTP GYPANEYAYR RGIAEAVGLP SIPVHPIGYY 300
DAQKLLEKMG GSAPPDSSWR GSLKVPYNVG PGFTGNFSTQ KVKMHIHSTN EVTRIYNVIG 360
TLRGAVEPDR YVILGGHRDS WVFGGIDPQS GAAVVHEIVR SFGTLKKEGW RPRRTILFAS 420
WDAEEFGLLG STEWAEENSR LLQERGVAYI NADSSIEGNY TLRVDCTPLM YSLVHNLTKE 480
LKSPDEGFEG KSLYESWTKK SPSPEFSGMP RISKLGSGND FEVFFQRLGI ASGRARYTKN 540
WETNKFSGYP LYHSVYETYE LVEKFYDPMF KYHLTVAQVR GGMVFELANS IVLPFDCRDY 600
AVVLRKYADK IYSISMKHPQ EMKTYSVSFD SLFSAVKNFT EIASKFSERL QDFDKSNPIV 660
LRMMNDQLMF LERAFIDPLG LPDRPFYRHV IYAPSSHNKY AGESFPGIYD ALFDIESKVD 720

| | | |
|---|---|---|
| SEQ ID NO: 213 | moltype = AA length = 33 | |
| FEATURE | Location/Qualifiers | |
| REGION | 1..33 | |
| | note = peptide | |
| source | 1..33 | |
| | mol_type = protein | |
| | organism = synthetic construct | |

SEQUENCE: 213
NLLHETDSAV ATARRPRWLC AGALVLAGGF FLL    33

| | | |
|---|---|---|
| SEQ ID NO: 214 | moltype = AA length = 35 | |
| FEATURE | Location/Qualifiers | |

```
REGION                      1..35
                            note = peptide
source                      1..35
                            mol_type = protein
                            organism = synthetic construct
SEQUENCE: 214
GFFLLGFLFG WFIKSSNEAT NITPKHNMKA FLDEL                                    35

SEQ ID NO: 215              moltype = AA   length = 36
FEATURE                     Location/Qualifiers
REGION                      1..36
                            note = peptide
source                      1..36
                            mol_type = protein
                            organism = synthetic construct
SEQUENCE: 215
TPKHNMKAFL DELKAENIKK FLYNFTQIPH LAGTEQ                                   36

SEQ ID NO: 216              moltype = AA   length = 37
FEATURE                     Location/Qualifiers
REGION                      1..37
                            note = peptide
source                      1..37
                            mol_type = protein
                            organism = synthetic construct
SEQUENCE: 216
KQIQSQWKEF GLDSVELAHY DVLLSYPNKT HPNYISI                                  37

SEQ ID NO: 217              moltype = AA   length = 33
FEATURE                     Location/Qualifiers
REGION                      1..33
                            note = peptide
source                      1..33
                            mol_type = protein
                            organism = synthetic construct
SEQUENCE: 217
DIVPPFSAFS PQGMPEGDLV YVNYARTEDF FKL                                      33

SEQ ID NO: 218              moltype = AA   length = 36
FEATURE                     Location/Qualifiers
REGION                      1..36
                            note = peptide
source                      1..36
                            mol_type = protein
                            organism = synthetic construct
SEQUENCE: 218
KVFRGNKVKN AQLAGAKGVI LYSDPADYFA PGVKSY                                   36

SEQ ID NO: 219              moltype = AA   length = 37
FEATURE                     Location/Qualifiers
REGION                      1..37
                            note = peptide
source                      1..37
                            mol_type = protein
                            organism = synthetic construct
SEQUENCE: 219
VQRGNILNLN GAGDPLTPGY PANEYAYRRG IAEAVGL                                  37

SEQ ID NO: 220              moltype = AA   length = 32
FEATURE                     Location/Qualifiers
REGION                      1..32
                            note = peptide
source                      1..32
                            mol_type = protein
                            organism = synthetic construct
SEQUENCE: 220
AQKLLEKMGG SAPPDSSWRG SLKVPYNVGP GF                                       32

SEQ ID NO: 221              moltype = AA   length = 31
FEATURE                     Location/Qualifiers
REGION                      1..31
                            note = peptide
source                      1..31
                            mol_type = protein
                            organism = synthetic construct
SEQUENCE: 221
KVKMHIHSTN EVTRIYNVIG TLRGAVEPDR Y                                        31

SEQ ID NO: 222              moltype = AA   length = 34
```

```
FEATURE                 Location/Qualifiers
REGION                  1..34
                        note = peptide
source                  1..34
                        mol_type = protein
                        organism = synthetic construct
SEQUENCE: 222
AVVHEIVRSF GTLKKEGWRP RRTILFASWD AEEF                                34

SEQ ID NO: 223          moltype = AA  length = 33
FEATURE                 Location/Qualifiers
REGION                  1..33
                        note = peptide
source                  1..33
                        mol_type = protein
                        organism = synthetic construct
SEQUENCE: 223
TEWAEENSRL LQERGVAYIN ADSSIEGNYT LRV                                 33

SEQ ID NO: 224          moltype = AA  length = 35
FEATURE                 Location/Qualifiers
REGION                  1..35
                        note = peptide
source                  1..35
                        mol_type = protein
                        organism = synthetic construct
SEQUENCE: 224
NADSSIEGNY TLRVDCTPLM YSLVHNLTKE LKSPD                               35

SEQ ID NO: 225          moltype = AA  length = 32
FEATURE                 Location/Qualifiers
REGION                  1..32
                        note = peptide
source                  1..32
                        mol_type = protein
                        organism = synthetic construct
SEQUENCE: 225
LMYSLVHNLT KELKSPDEGF EGKSLYESWT KK                                  32

SEQ ID NO: 226          moltype = AA  length = 33
FEATURE                 Location/Qualifiers
REGION                  1..33
                        note = peptide
source                  1..33
                        mol_type = protein
                        organism = synthetic construct
SEQUENCE: 226
SGMPRISKLG SGNDFEVFFQ RLGIASGRAR YTK                                 33

SEQ ID NO: 227          moltype = AA  length = 33
FEATURE                 Location/Qualifiers
REGION                  1..33
                        note = peptide
source                  1..33
                        mol_type = protein
                        organism = synthetic construct
SEQUENCE: 227
SGYPLYHSVY ETYELVEKFY DPMFKYHLTV AQV                                 33

SEQ ID NO: 228          moltype = AA  length = 36
FEATURE                 Location/Qualifiers
REGION                  1..36
                        note = peptide
source                  1..36
                        mol_type = protein
                        organism = synthetic construct
SEQUENCE: 228
FYDPMFKYHL TVAQVRGGMV FELANSIVLP FDCRDY                              36

SEQ ID NO: 229          moltype = AA  length = 34
FEATURE                 Location/Qualifiers
REGION                  1..34
                        note = peptide
source                  1..34
                        mol_type = protein
                        organism = synthetic construct
SEQUENCE: 229
VLRKYADKIY SISMKHPQEM KTYSVSFDSL FSAV                                34
```

```
SEQ ID NO: 230          moltype = AA   length = 34
FEATURE                 Location/Qualifiers
REGION                  1..34
                        note = peptide
source                  1..34
                        mol_type = protein
                        organism = synthetic construct
SEQUENCE: 230
ERLQDFDKSN PIVLRMMNDQ LMFLERAFID PLGL                              34

SEQ ID NO: 231          moltype = AA   length = 35
FEATURE                 Location/Qualifiers
REGION                  1..35
                        note = peptide
source                  1..35
                        mol_type = protein
                        organism = synthetic construct
SEQUENCE: 231
LGLPDRPFYR HVIYAPSSHN KYAGESFPGI YDALF                             35

SEQ ID NO: 232          moltype = AA   length = 34
FEATURE                 Location/Qualifiers
REGION                  1..34
                        note = peptide
source                  1..34
                        mol_type = protein
                        organism = synthetic construct
SEQUENCE: 232
ESKVDPSKAW GEVKRQIYVA AFTVQAAAET LSEV                              34
```

FORMULATION OF A PEPTIDE VACCINE

CROSS-REFERENCE TO RELATED APPLICATIONS

This application is a is a Continuation of U.S. patent application Ser. No. 16/898,141, filed Jun. 10, 2020, which is a Continuation of U.S. patent application Ser. No. 16/311,629, filed Dec. 19, 2018, which is the National Phase of International Patent Application No. PCT/EP2017/064882, filed Jun. 19, 2017, published as WO 2017/220463, which claims priority to European Application No. 16175215.9, filed Jun. 20, 2016. The contents of these applications are herein incorporated by reference in their entirety.

SEQUENCE LISTING

The present application is filed along with a Sequence Listing in electronic format. The Sequence Listing is provided as a file entitled 069818-4282.xml, created on Mar. 3, 2023, which is 290,454 bytes in size. The information in the electronic format of the Sequence Listing is incorporated herein by reference in its entirety.

FIELD OF THE INVENTION

This invention is in the field of medicine and immunology. In particular, it relates to a novel composition for reconstituting peptides for vaccination. This composition is in particular suitable for preparing pharmaceutical peptide-based vaccines that further comprise an oil-based adjuvant.

BACKGROUND OF THE INVENTION

Clinical results have indicated that the era of successful therapeutic vaccination has arrived. Regression of lesions was shown for premalignant lesions caused by HPV and the clinical benefit of prolonged survival has been established. Vaccines based on synthetic long peptides are among the optimal vaccine platforms. Peptide vaccine or peptides-based vaccines are developed for the treatment of persistent infections and cancer, preferably targeting the immune system to clear cells that express viral antigens, cancer-antigens and/or neo-antigens. It is appreciated in the art that peptide-based vaccines capable of eliciting an effective cellular immune response ($CD4^+$ and $CD8^+$ T-cell response) targeting antigen-specific cytotoxic T cells capable of clearing the antigen-expressing cells. Antigens of choice include mutant sequences, selected cancer testis antigens and viral antigens (for review, see Melief et al. 2016 *Journal of Clinical Investigation*, Vol 125(9) pages 3401-3412).

One of the challenges of peptide-based vaccines is to provide for physically and chemically stable injectable solutions. This is in particular a challenge for peptide-based vaccine emulsions comprising more than one peptide and oil-based adjuvants. Injectable vaccine solutions are typically prepared on-site about 1 to 3 hours before administration to the patient using dried, mostly lyophilized peptides as a starting material. Therefore, there is a need for a suitable reconstitution composition that allows for the fast reconstitution of dried peptides, which can subsequently be admixed easily with oil-based adjuvants resulting in an emulsion that is physically and chemically stable for at least 2 to 3 hours storage at room temperature before being administered to the patient.

DETAILED DESCRIPTION OF THE INVENTION

Reconstitution Composition

Provided is a novel composition for reconstituting peptides for vaccination. This reconstitution composition comprises or consists of about 60-80% v/v aqueous solution comprising an organic acid, about 5-10% v/v propylene glycol (CAS no. 57-55-6), about 10-20% v/v lower alcohol and about 5-10% v/v non-ionic hydrophilic surfactant.

Preferably, the organic acid is a weak organic acid such as a carboxylic acid. A weak organic acid is to be understood herein as an organic acid having a $pK_a$ (logarithmic acid dissociation constant) of between −2 and 12. Preferably the weak organic acid has a $pK_a$ of between 1 and 10, or between 2 and 5 or even between 3 and 4. The weak organic acid may be, but is not limited to, any carboxylic acid selected from the group consisting of oxalic acid (ethanedioic acid), citric acid (2-hydroxypropane-1,2,3-tricarboxylic acid), malic acid (2-hydroxybutanedioic acid), carbonic acid (hydroxymethanoic acid), benzoic acid (benzenecarboxylic acid or phenylmethanoic acid), formic acid (methanoic acid), lactic acid (2-hydroxypropanoic acid), acetic acid (ethanoic acid), butyric acid (butanoic acid), valeric acid (pentanoic acid), caproic acid (hexanoic acid), and propionic acid (propanoic acid). Most preferably, the organic acid is citric acid.

The organic acid may be present in the aqueous solution at concentrations ranging from about 0.008 to 0.25M, or from about 0.01 to 0.2M, or from 0.05 to 0.1M. The reconstitution composition of the invention comprising 60-80%, or 65%-75% or 67%-72%, or about 70% of said aqueous solution preferably has a resulting concentration of said organic acid ranging from 0.05 to 0.2M, 0.006 to 0.16M, 0.008 to 0.12M, 0.03 to 0.08M, or preferably from 0.04 to 0.6M.

A lower alcohol is understood herein as an organic compound having a hydroxyl functional group bound to a saturated carbon atom of a lower alkyl or lower substituted alkyl group, wherein a lower alkyl or lower substituted alkyl group has at most 6 carbon atoms and preferably has the structure $CH_3-(CH_2)_n-OH$, wherein n=1, 2, 3, 4 or 5. Preferably, the lower alcohol is selected from the group consisting of methanol, ethanol, propanol, butanol and pentanol, most preferably the lower alcohol is ethanol.

The non-ionic hydrophilic surfactant preferably has a hydrophilic-lipophilic balance (HLB) value between 9 and 14, more preferably between 12 and 14. This surfactant may be, but is not limited to ethoxylated fatty acid mono- (in particular 5 ethoxyl groups), di- or tri- (in particular 20 ethoxyl groups) ester of sorbitan, wherein the fatty acid is preferably selected from the group consisting of oleate (e.g. ethoxylated sorbitan monooleate such as Tween 81® and/or ethoxylated sorbitan trioleate such as Tween 85®), palmitate, stearate (e.g. ethoxylated sorbitan tristearate such as Tween 65®), isostearate, laurate and the combinations thereof; ethoxylated fatty alcohols (in particular 5-10 ethoxyl groups) (e.g. Brij 76®, Brij 56®, Brij 96®), ethoxylated fatty acids (in particular 5-10 ethoxyl groups) (e.g. Simulsol 2599®, Myrj 45®), ethoxylated castor oil (in particular 25-35 ethoxyl groups) (e.g. Arlatone 650®, Arlatone G®, Cremophor EL®), and combinations thereof.

In one embodiment of the composition of the invention, the non-ionic hydrophilic surfactant:

a. is a mono-, di or triglyceride, preferably an ethoxylated triglyceride, and/or b. has a hydrophilic-lipophilic balance (HLB) value between 9 and 14.

The HLB value is calculated using the formula HLB=20 $(1-I_s/I_a)$, in which $I_s$ represents the saponification index or saponification value and $I_a$ represents the acid index or acid value of said surfactant or of said mixture of surfactants. These two indices, saponification and acid values, are determined by methods described in the European Pharmacopoeia (Edition 8.8, section 2.5.6 and 2.5.1, respectively).

In a preferred embodiment, the non-ionic hydrophilic surfactants is ethoxylated castor oil, more in particular polyoxyl 35 hydrogenated castor oil or polyoxyethyleneglyceroltriricinoleate 35 (CAS no. 61791-12-6) (e.g. Cremophor EL®) which is a mixture of polyoxyethylated triglycerides obtained by reacting castor oil with ethylene oxide in a molar ration of 1:35.

Preferably, the reconstitution composition of the invention comprises or consists of about 75% v/v aqueous solution comprising about 0.1M citric acid in water, about 6.25% v/v propylene glycol (CAS no. 57-55-6), about 12.5% v/v ethanol and about 6.25% v/v polyoxyethyleneglyceroltriricinoleate 35 (CAS no. 61791-12-6). In other words, the reconstitution composition comprises or consist of about 0.075M citric acid, about 6.25% v/v propylene glycol (CAS no. 57-55-6), about 12.5% v/v ethanol and about 6.25% v/v polyoxyethyleneglyceroltriricinoleate 35 (CAS no. 61791-12-6) in water.

Also preferred is a reconstitution composition comprising or consisting of about 75% v/v aqueous solution comprising about 0.1M citric acid in water, about 6.25% v/v propylene glycol (CAS no. 57-55-6), about 12.5% v/v ethanol, about 6.25% v/v polyoxyethyleneglyceroltriricinoleate 35 (CAS no. 61791-12-6) and 20 µg/mL CpG ODN1826, or comprising or consisting of about 0.075M citric acid, about 6.25% v/v propylene glycol (CAS no. 57-55-6), about 12.5% v/v ethanol, about 6.25% v/v polyoxyethyleneglyceroltriricinoleate 35 (CAS no. 61791-12-6) and 20 µg/mL CpG ODN1826 in water.

The reconstitution composition is in particular suitable for reconstituting stored peptides as defined herein below under Pharmaceutical composition, i.e. preferably having a length of between 15 and 100 amino acids. The difficulty to form stable solutions upon reconstitution of peptides of the length defined above is appreciated in the art, especially in case of different peptides, i.e. peptides having different amino acid sequences and hence have different chemical properties and behave physically different. As a result, it is hard to reconstitute them in one and the same solution. On top of that, in case one or more of these peptides comprise cysteines, the tendency to form SS-bridges has to be dealt with. Although intramolecular disulfide bonds may be required in vaccine peptides in order to be immunogenic, intermolecular disulfide bridge formation is undesirable as it results in instable solutions.

The inventors now have identified that the reconstitution composition of the present invention is in particular suitable for forming highly stable reconstituted peptides compositions wherein the amount of intermolecular disulfide bridges is minimalized, without compromising on immunogenicity of the reconstituted peptides. Therefore, the reconstitution composition of the invention prevents intermolecular disulfide formation of the peptides to be reconstituted as further defined herein, without comprising on immunogenicity of these peptides.

Preferably, the reconstitution composition of the invention is a sterile and/or pharmaceutical-grade or clinical-grade composition, suitable for parental administration to a subject, i.e. a mammalian species or human being. Preferably, the reconstitution composition of the invention is manufactured using Good Manufacturing Practice (GMP) and has GMP quality as defined by both the European Medicines Agency and the Food and Drug Administration. The reconstitution composition of the invention may be packaged in a vial. The invention also provides for a vial comprising a volume of reconstitution composition suitable for reconstituting a single pharmaceutical dosage unit as further defined herein, or multiples thereof, i.e. a volume suitable for reconstituting a 2, 3, 4, 5, 6, 7, 8, 9, 10 or more pharmaceutical dosage units. Preferably, said vial is stored at a temperature at which the reconstitution composition is stable for at least 1 month, 2 months, 3 months, 6 months or 1 year or even 2 years. Preferably, said temperature is between −25° C. and 25° C., or between −23° C. and −18° C., or between 0° C. and 10° C., or between 2° C. and 8° C., or between 18° C. and 23° C.

Preferably, the volume of reconstitution composition of the invention present in the vial is at most 50 mL, preferably between 0.1 and 10 mL, preferably between 1 and 10 mL, such as, 0.5, 1, 2, 3, 4, 5 or 10 mL, or any value in between. A vial is to be understood herein as a container that can have any shape. Optionally, a vial is to be understood herein as a syringe.

Pharmaceutical Composition

The reconstitution composition of the invention is in particular suitable for reconstituting peptides for the preparation of a medicament or pharmaceutical composition. Such pharmaceutical composition may be a vaccine, preferably a peptide vaccine. A "vaccine" is to be understood herein as a composition comprising antigenic compounds, optionally complemented with further immune stimulating compounds, for generating immunity for the prophylaxis and/or treatment of diseases such as conditions associated with persistent infection and/or metaplasia and/or dysplasia and/or neoplasia. A "peptide-based vaccine" or "peptide vaccine" (these terms are used herein interchangeably) is to be understood herein as a vaccine wherein peptides constitute the active ingredients, i.e. the antigenic compounds. Preferably, such peptides are synthetic long peptides. More preferably, comprising Human Leukocyte Antigen (HLA)-epitopes capable of inducing CD4+ and/or CD8+ T cell responses.

Therefore, provided is a pharmaceutical composition comprising peptides reconstituted in the reconstitution composition of the invention. Preferably, the pharmaceutical composition of the invention is a vaccine, preferably a peptide-based vaccine. Such a peptide-based vaccine may be used for the treatment of persistent infections, pre-cancerous conditions and cancer, preferably activating the cellular immune system to clear infected, pre-cancerous and/or cancerous cells that express viral antigens, Tumor-Associated-Antigens, like cancer testis antigens and/or Tumor-Specific antigens, like oncogenic or non-oncogenic viral antigens and/or neo-antigens resulting from DNA mutations.

The pharmaceutical composition is preferably for, and therefore formulated to be suitable for, administration to a subject, preferably a human or animal subject. Preferably, the administration is parenteral, e.g. intravenous, subcutaneous, intramuscular, intradermal intracutaneous and/or intratumoral administration, i.e. by injection.

The inventors found that the reconstitution composition comprising reconstituted peptides is in particular suitable for admixing with an oil-based adjuvant, resulting in a chemically and physically stable peptide-vaccine solution.

"Chemically stable" is referred herein in the context of a peptide solution and/or peptide-vaccine composition and is to be understood herein as a solution or composition comprising peptides that do not chemically degrade or decompose, for instance because of the formation of intra- or intermolecular disulfide bridges, to an unacceptable degree; i.e. the amount of un-degraded, un-decomposed and/or unreacted peptides within the solution and/or composition is at least 90%, 91%, 92%, 93%, 94%, 95%, 96%, 97%, 98%, 99% or even 100% by weight as compared to its original, after storage of the solution or composition for at least about 0.5, 1, 1.5, 2 or at least 3 hours at room temperature. Chemical stability can be assessed using any suitable technique known in the art, for instance using UPLC/MS as exemplified herein. When using UPLC/MS, a solution/composition is defined as chemically stable if the total % area of new peaks appearing after storage of at least about 0.5, 1, 1.5, 2 or at least 3 hours at room temperature is at most 20%, 15%, 10%, 9%, 8%, 7%, 6%, 5%, 4%, 3%, 2%, 1%, or 0% as compared to its original, wherein new peaks are understood to be the peaks on a UPLC chromatograms of the stored solution that were not identified on the UPLC chromatograms of the original ("original" being understood herein as the freshly prepared solution directly after preparation), when measured under the same conditions. Preferably, the total % area of new peaks appearing after storage of 3 hours at room temperature is at most 20%, 15%, 10%, 9%, 8%, 7%, 6%, 5%, 4%, 3%, 2%, 1%, or 0%, preferably at most 10% as compared to its original, when measured under the same conditions.

"Physically stable" is referred herein in the context of a peptide solution and/or peptide-vaccine composition and is to be understood herein as a solution or composition comprising peptides that do not precipitate or re-disperse. Physical stability can be assessed using any suitable technique known in the art, for instance by visual inspection or by particle distribution using a Malvern Mastersizer as exemplified herein, wherein average particle size is expressed in D(0.5). When using Malvern Mastersizer for assessing physical stability as exemplified herein, a solution/composition is defined as physically stable if the average D (0.5) after storage of at least about 0.5, 1, 1.5, 2 or at least 3 hours at room temperature is increased at most 50%, 40%, 30%, 20%, 10% or 5% as compared to its original (i.e. the freshly prepared solution directly after preparation). Preferably, a solution/composition is defined as physically stable if the average D(0.5) after storage of 3 hours at room temperature is increased at most 50%, 40%, 30%, 20%, 10% or 5%, preferably at most 20%, as compared to its original.

Preferably, the pharmaceutical composition of the invention further comprises an adjuvant. The term "adjuvant" is used herein to refer to substances that have immune-potentiating effects and are added to or co-formulated with an antigenic agent in order to enhance, induce, elicit, and/or modulate the immunological response against the antigenic agent when administered to a subject. Oil-based adjuvants can be used to form emulsions (e.g. water-in-oil or oil-in-water emulsions) and are appreciated in the art to enhance and direct the immune response. The presence of such adjuvant in a therapeutic vaccine is highly beneficial. Therefore, the present invention also provides for a pharmaceutical composition or medicament comprising or consisting of the reconstitution composition of the invention, reconstituted peptides and an oil-based adjuvant, more in particular the invention provides for a pharmaceutical composition comprising about 0.5-10 mg/mL peptides in about 40-60% v/v of the reconstitution composition of the invention and about 40-60% v/v of an oil-based adjuvant.

The oil-based adjuvant may be any mineral or non-mineral oil-based adjuvant known in the art. Preferably the oil-based adjuvant is a mineral oil-based adjuvant. Non-limiting examples of oil-based adjuvants are bio-based oil adjuvants (based on vegetable oil/fish oil, etc.), squalene-based adjuvant (e.g. MF59), Syntex Adjuvant Formulation (SAF; Lidgate, Deborah M, *Preparation of the Syntex Adjuvant Formulation (SAF, S4-m, and SAF-*1), In: *Vaccine Adjuvants, Volume 42 of the series Methods in Molecular Medicine*™ p229-237, ISSN1543-1894), Freund's Complete Adjuvant (FCA), Freund's Incomplete Adjuvant (FIA), adjuvants based on peanut oil (e.g. Adjuvant 65), Lipovant (Byars, N. E., Allison, A. C., 1990. *Immunologic adjuvants: general properties, advantages, and limitations*. In: Zola, H. (Ed.), *Laboratory Methods in Immunology*. p 39-51), ASO4 (A. Tagliabue, R. Rappuoli *Vaccine adjuvants: the dream becomes real Hum. Vaccine,* 4 (5), 2008, p 347-349), Montanide adjuvants, which are based on purified squalene and squalene emulsified with highly purified mannide monooleate (e.g. Montanide ISA 25 VG, 28 VG, 35 VG, 50 V, 50 V2, 51 VG, 61 VG, 70 VG, 70 M VG, 71 VG, 720 VG, 760 VG, 763 A VG, 775 VG, 780 VG, 201 VG, 206 VG, 207 VG). Preferably the oil-based adjuvant is a mineral oil-based adjuvant. More preferably, the oil-based adjuvant is Montanide ISA 51VG (Seppic), which is a mixture of Drakeol VR and mannide monooleate.

Preferably, the pharmaceutical composition comprises or consists of an amount of peptides that constitutes a pharmaceutical dosage unit. A pharmaceutical dosage unit is defined herein as the amount of active ingredients (i.e. the total amounts of peptides in a peptide-based vaccine) that is applied to a subject at a given time point. A pharmaceutical dosage unit may be applied to a subject in a single volume, i.e. a single shot, or may be applied in 2, 3, 4, 5 or more separate volumes or shots that are applied preferably at different locations of the body, for instance in the right and the left limb. Reasons for applying a single pharmaceutical dosage unit in separate volumes may be multiples, such as avoid negative side effects, avoiding antigenic competition and/or composition analytics considerations. It is to be understood herein that the separate volumes of a pharmaceutical dosage may differ in composition, i.e. may comprise different kinds or composition of active ingredients and/or adjuvants. It is to be understood that for all active ingredients (antigenic peptides) within the whole pharmaceutical dosage unit a single reconstitution composition is used, as one of the benefits of the invention is that the reconstitution composition of the invention is suitable for reconstituting, and subsequent emulsification using an oil-based adjuvant, of different peptide mixtures. A single reconstitution composition, and preferably a single oil-based adjuvant, minimizes the chance of human failure in reconstitution and emulsification.

A single injection volume or shot (i.e. volume applied on one location at a certain time point), comprising a total pharmaceutical dosage, or part thereof in case multiple shots applied at substantially the same time point, may between 100 µL and 2 mL, or between 100 µL and 1 mL. The single injection volume may be 100 µL, 200 µL, 300 µL, 400 µL, 500 µL, 600 µL, 700 µL, 800 µL, 900 µL, 1 mL, 1.1 mL, 1.2 mL, 1.3 mL, 1.4 mL, 1.5 mL, 1.6 mL, 1.7 mL, 1.8 mL, 1.9 mL, 2 mL, 3 mL or any value in between.

A pharmaceutical dosage unit may be an effective amount or part of an effective amount. An "effective amount" is to be understood herein as an amount or dose of active ingredients required to prevent and/or reduce the symptoms of a disease (e.g., chronic infection, pre-cancerous condition and/or cancer) relative to an untreated patient. The effective amount of active compound(s) used to practice the present invention for preventive and/or therapeutic treatment of a disease or condition varies depending upon the manner of administration, the age, body weight, and general health of the subject. Ultimately, the attending physician or veterinarian will decide the appropriate amount and dosage regimen. Such amount is referred to as an "effective" amount. This effective amount may also be the amount that is able to induce an effective cellular T cell response in the subject to be treated, or more preferably an effective systemic cellular T cell response.

Preferably, pharmaceutical dosage unit, or total amount of peptides applied to a subject at a given time point, either in a single or in multiple injections at a certain time point, comprises an amount of peptides in the range from 0.1 µg to 20 mg, such as about 0.1 µg, 0.5 g, 1 µg, 5 µg, 10 µg, 15 µg, 20 µg, 30 µg, 40 µg, 50 µg, 60 µg, 70 µg, 80 µg, 90 µg, 100 µg, 150 µg, 200 µg, 250 µg, 300 µg, 350 µg, 400 µg, 450 µg, 500 µg, 650 µg, 700 µg, 750 µg, 800 µg, 850 µg, 900 µg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 15 mg or about 20 mg or any value in between. Preferred ranges of pharmaceutical dosage units are from 0.1 µg to 20 mg, 1 µg to 10 mg, 10 µg to 5 mg, 0.5 mg to 2 mg, 0.5 mg to 10 mg or 1 mg to 5 mg or 2 to 4 mg.

Preferably, the pharmaceutical composition comprises or consists of about 1-2 mg/mL peptides in 40-60% v/v of the reconstitution composition as defined above and 40-60% v/v of an oil-based adjuvant. The pharmaceutical composition may comprise or consist about 40%, 41%, 42%, 43%, 44%, 45%, 46%, 47%, 48%, 49%, 50%, 51%, 52%, 53%, 54%, 56%, 57%, 58%, 59% or 60% v/v of an oil-based adjuvant. Preferably, the pharmaceutical composition comprises or consists of about 1-2 mg/mL peptides in about 50% v/v of the reconstitution composition as defined above and about 50% v/v of an oil-based adjuvant, preferably Montanide ISA 51 VG (Seppic). In other words, preferably, the pharmaceutical composition comprises or consists of about 1-2 mg/mL peptide, 0.038M citric acid, about 3.13% v/v propylene glycol (CAS no. 57-55-6), about 6.25% v/v ethanol, about 3.13% v/v polyoxyethyleneglyceroltriricinoleate 35 (CAS no. 61791-12-6) and about 50% of an oil-based adjuvant, preferably Montanide ISA 51 VG (Seppic), in water.

The pharmaceutical composition of the invention may comprise one or more further immune response stimulating compounds or adjuvants. Advantageously, the medicament according to the invention may additionally comprise one or more synthetic adjuvants. Such a further immune response stimulating compound or adjuvant may be (i) admixed to the pharmaceutical composition according to the invention after reconstitution of the peptides and optional emulsification with an oil-based adjuvant as defined above, (ii) may be part of the reconstitution composition of the invention defined above, (iii) may be physically linked to the peptide(s) to be reconstituted or (iv) may be administered separately to the subject, mammal or human, to be treated. It is to be construed herein that when an immune response stimulating compound is admixed to the medicament according to the invention, it is depicted as an adjuvant; when administered separately, it is depicted as an immuno-modulatory agent, or an immuno-modulator, which terms are used herein interchangeably. Particularly preferred are adjuvants that are known to act via the Toll-like receptors and/or via a RIG-I (Retinoic acid-Inducible Gene-1) protein and/or via an endothelin receptor. Immune modifying compounds that are capable of activation of the innate immune system can be activated particularly well via Toll like receptors (TLRs), including TLRs 1-10. Compounds capable of activating TLR receptors and modifications and derivatives thereof are well documented in the art. TLR1 may be activated by bacterial lipoproteins and acetylated forms thereof, TLR2 may in addition be activated by Gram positive bacterial glycolipids, LPS, LPA, LTA, fimbriae, outer membrane proteins, heat shock proteins from bacteria or from the host, and Mycobacterial lipoarabinomannans. TLR3 may be activated by dsRNA, in particular of viral origin, or by the chemical compound poly(I:C). TLR4 may be activated by Gram negative LPS, LTA, Heat shock proteins from the host or from bacterial origin, viral coat or envelope proteins, taxol or derivatives thereof, hyaluronan containing oligosaccharides and fibronectins. TLR5 may be activated with bacterial flagellae or flagellin. TLR6 may be activated by mycobacterial lipoproteins and group B *Streptococcus* heat labile soluble factor (GBS-F) or *Staphylococcus* modulins. TLR7 may be activated by imidazoquinolines, such as imiquimod, resiquimod and derivatives imiquimod or resiquimod (e.g. 3M-052). TLR9 may be activated by unmethylated CpG DNA or chromatin-IgG complexes. In particular TLR3, TLR7 and TLR9 play an important role in mediating an innate immune response against viral infections, and compounds capable of activating these receptors are particularly preferred in a the compositions or medicaments according to the invention. Particularly preferred adjuvants comprise, but are not limited to, synthetically produced compounds comprising dsRNA, poly(I:C), poly I:CLC, unmethylated CpG DNA which trigger TLR3 and TLR9 receptors, IC31, a TLR 9 agonist, IMSAVAC, a TLR 4 agonist, Montanide ISA-51, Montanide ISA 720 (an adjuvant produced by Seppic, France). RIG-I protein is known to be activated by ds-RNA just like TLR3 (Kato et al, (2005) *Immunity*, 1: 19-28). A particularly preferred TLR ligand is a pam3cys and/or derivative thereof, preferably a pam3cys lipopeptide or variant or derivative thereof, preferably such as described in WO2013051936A1, more preferably U-Pam12 or U-Pam14 or AMPLIVANT®. Further preferred adjuvants are Cyclic dinucleotides (CDNs), Muramyl dipeptide (MDP) and poly-ICLC. In a preferred embodiment, the adjuvants of the invention are non-naturally occurring adjuvants such as the pam3cys lipopeptide derivative as described in WO2013051936A1, Poly-ICLC, imidazoquinoline such as imiquimod, resiquimod or derivatives thereof, CpG oligodeoxynucleotides (CpG-ODNs) having a non-naturally occurring sequence, and peptide-based adjuvants, such as muramyl dipeptide (MDP) or tetanus toxoid peptide, comprising non-naturally occurring amino acids. Further preferred are adjuvants selected from the group consisting of: 1018 ISS, aluminum salts, Amplivax, AS 15, BCG, CP-870,893, CpG7909, CyaA, dSLIM, GM-CSF, IC30, IC31, ImuFact EV1P321, IS Patch, ISS, ISCOMATRIX, Juvlmmune, LipoVac, MF59, monophosphoryl lipid A, Montanide IMS 1312, Montanide ISA 206, Montanide ISA 50V, OK-432, OM-174, OM-197-MP-EC, ONTAK, PepTel®, vector system, PLGA microparticles, SRL172, Virosomes and other Virus-like particles, Pam3Cys-GDPKHPKSF, YF-17D, VEGF trap, R848, beta-glucan, Aquila's QS21 stimulon, vadimezan, AsA404 (DMXAA), STING (stimulator of IFN genes) agonist (e.g. c-di-GMP VacciGrade™), PCI, NKT (natural killer T cell) agonist (e.g. alpha-galactosylceramide or alpha-GalCer, RNAdjuvant® (Curevac), retinoic acid inducible protein I ligands (e.g. 3pRNA or 5'-triphosphate RNA).

As indicated above, an adjuvant may be physically linked to the peptide(s) to be reconstituted. Physical linkage of adjuvants and costimulatory compounds or functional groups to antigenic peptides as defined herein below provides an enhanced immune response by improved targeting to antigen-presenting cells, in particular dendritic cells, that internalize, metabolize and display antigen and by simultaneously stimulating such cells to up-regulate expression of a variety of co-stimulatory molecules, thereby becoming efficient T cell response inducing and enhancing cells. Another preferred immune modifying compound is an inhibitor of an endothelin receptor such as BQ-788 (Buckanovich R J et al., (2008) *Nature Medicine* 14: 28; Ishikawa K, (1994) *PNAS* 91: 4892), and/or derivatives thereof. BQ-788 is N-cis-2,6-dimethylpiperidinocarbonyl-L-gamma-methylleucyl-D-1-methoxycarbonyltryptophanyl-D-norleucine. Another preferred immune response stimulating compound or adjuvant is Interferon alpha (IFNα), more preferably pegylated Interferon alpha. Furthermore, the use of antigen presenting cell (co)stimulatory molecules, as set out in WO99/61065 and in WO03/084999, in combination with the peptides and compositions of the invention is preferred. In particular the use of 4-1BB and/or CD40 ligands, agonistic antibodies, OX40 ligands, CD27 ligands or functional fragments and derivatives thereof, as well as synthetic compounds with similar agonistic activity are preferably administered separately or combined with the peptides of the invention to subjects to be treated in order to further stimulate the mounting of an optimal immune response in the subject.

The peptides to be reconstituted in the reconstitution composition of the invention and/or comprised within the pharmaceutical composition of the invention, preferably have a length from about 15 to about 100 amino acids. Preferably, the peptides to be reconstituted are between 15-100 amino acids in length, or 15-95 amino acids, or 15-90 amino acids, or 15-85 amino acids, or 15-70 amino acids, or 15-65 amino acids, or 15-60 amino acids, or 15-55 amino acids, or 15-50 amino acids, or 15-45 amino acids, or 15-40 amino acids, or 17-39 amino acids, or 19-43 amino acids, or 22-40 amino acids, or 22-45 amino acids, or 28-40 amino acids or 30-39 amino acids in length. Preferably, the peptides to be reconstituted are at most 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, or 30 amino acids. Preferably, the peptides to be reconstituted are at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 amino acids. Preferably, the peptides to be reconstituted are at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 amino acids and no more than 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, or 30 amino acids, or any combination of these lower and upper limits.

The peptides to be reconstituted in the reconstitution composition of the invention and/or comprised within the pharmaceutical composition of the invention, may be peptides derived from protein antigens. A "protein antigen" is to be understood herein as a protein or polypeptide that comprises antigenic regions capable of inducing an immune response in a host animal or human. Protein antigens that are specifically expressed by infected, pre-cancerous and/or cancerous cells are suitable targets for therapeutic vaccines. Such protein antigens may be viral or non-viral antigens. Examples of viral antigens that are targets for prophylactic and therapeutic vaccines are antigens derived from Epstein Bar virus induced lymphoma's (EBV), Human T lymphotrophic virus I, Hepatitis B virus (HBV), Human papilloma virus (HPV), Kaposi sarcoma herpes virus (KSHV), Hepatitis C virus (HVC), KSV and Merkel cell carcinoma virus. Non-limiting examples of viral protein antigens are protein antigens from EBV, e.g. LMP1 or late membrane protein 1 (e.g. UniprotKB P03230) and LMP2 or late membrane protein 2 (e.g. UniprotKB P13285); protein antigens from Human T lymphotrophic virus I, e.g. Tax protein (e.g. UniprotKB P14079; P0C213; P03409); protein antigens from HBV e.g. genotypes A, B, C or D, e.g. protein HBsAg (e.g. UniprotKB Q773S4), X-protein (e.g. UniprotKB Q8V1H6) Large envelope protein (e.g. UniprotKB P03138) and capsid protein (e.g. UniprotKB P03147); protein antigens from HCV, e.g. genome polyprotein (e.g. UniprotKB P26663; Q99IB8; A3EZI9) and HCV protein (e.g. UniprotKB Q99398); protein antigens from HPV e.g. oncogenic genotypes 6, 11, 16 or 18, e.g. E6 oncoprotein (e.g. UniprotKB P03126; P06463) and E7 oncoprotein (e.g. UniprotKB P03129; P06788) protein antigens from KSHV, e.g. protein ORF36 (e.g. UniprotKB F5HGH5), Core gene UL42 family protein (e.g. UniprotKB Q77ZG5), Virion egress protein UL31 homolog (e.g. UniprotKB F5H982), Triplex capsid protein VP19C homolog (e.g. UniprotKB F5H8Y5), Viral macrophage inflammatory protein 2 (e.g. UniprotKB Q98157), mRNA export factor ICP27 homolog (e.g. UniprotKB Q2HR75), ORF52 (e.g. UniprotKB F5HBL8), Viral IRF4-like protein (e.g. UniprotKB Q2HR73), Bcl-2 (e.g. UniprotKB Q76RI8), Large tegument protein deneddylase (e.g. UniprotKB Q2HR64), V-cyclin (e.g. UniprotKB O40946), VIRF-1 (e.g. UniprotKB F5HF68) and E3 ubiquitin-protein ligase MIR1 (e.g. UniprotKB P90495) and antigen protein Merkel cell carcinoma virus, e.g. large T protein (e.g. UniprotKB E2IPT4; K4P159), e.g. small T protein (e.g. UniprotKB B6DVX0; B6DVX6).

Non-viral antigens that are suitable targets for prophylactic and therapeutic vaccines may be tumor specific antigens and/or tumor associated antigen. Tumor specific antigens are antigens that are exclusively expressed by tumor cells and not by any other cell and are often mutated proteins, such as $Kras^{G12D}$ and mutant P53, or neo-antigens developed in due course by DNA mutations and malfunctioning DNA repair mechanisms. Tumor associated antigens are endogenous antigens present in both tumor and normal cells but are dysregulated in their expression or cellular localization, such as the HER-2/neu receptor. Non limiting examples of such non-viral antigens that may be targets for therapeutic vaccines are Her-2/neu (or ErbB-2, Human Epidermal growth factor Receptor 2 (e.g. UniprotKB P04626); WT-1 or Wilms tumor protein (e.g. UniprotKB P19544); NY-ESO-1 or cancer/testis antigen 1 (e.g. UniprotKB P78358); MAGE-A3 or melanoma-associated antigen-A3 (e.g. UniprotKB P43357); BAGE or B melanoma antigen (e.g UniProtKB Q13072); CEA or carcinoembryonic antigen (e.g UniProtKB Q13984); AFP or α-fetoprotein (e.g UniProtKB P02771); XAGE-1B or X antigen family member 1 (e.g UniProtKB Q9HD64); survivin or BIRC5, Baculoviral IAP repeat-containing protein 5 (e.g. UniprotKB O15392); P53 (e.g. UniprotKB P04637); h-TERT or Telomerase reverse transcriptase (e.g. UniprotKB O14746); mesothelin (e.g. UniProtKB H3BR90); PRAME or Melanoma antigen preferentially expressed in tumors (e.g. UniprotKB P78395); MUC-1 or mucin-1 (e.g. UniprotKB P15941); Mart-1/Melan-A or Melanoma antigen recognized by T-cells 1 (e.g. UniprotKB Q16655); GP-100 or Melanocyte protein PMEL (e.g. UniprotKB P40967); tyrosinase (e.g. UniprotKB U3M8N0); tyrosinase-related protein-1 (e.g. UniprotKB P17643); tyrosinase-related protein-2 (e.g. UniprotKB O75767); PAP or PAPOLA, Poly(A) polymerase alpha (e.g. UniprotKB P51003); PSA or Prostate-specific antigen (e.g. UniprotKB P07288); PSMA or prostate-specific membrane antigen, or Glutamate carboxypeptidase 2 (e.g. UniprotKB Q04609).

Preferred tumor specific antigen targets for peptide-vaccines are viral oncogenes and neo-antigens. "Neo-antigen" is to be understood herein as a tumor antigen that arises from a tumor-specific mutation(s) which alters the amino acid sequence of genome-encoded proteins. Neo-antigens can be identified by whole-genome sequencing elucidating all, or nearly all, mutated neo-antigens that are uniquely present in a cancer (or neoplasia or tumor) of an individual patient. This collection of mutated neo-antigens may be analyzed to identify a specific, optimized subset of mutated neo-epitopes for use as an antigen source for the development of a personalized cancer vaccine for treatment of the patient's cancer. Methods to identify such neo-antigens are described in WO2014/168874, which is incorporated herein by reference.

Peptides "derived" from an antigen protein is to be understood herein as to comprise a contiguous amino acid sequence selected from the antigen protein, which may be modified by deletion or substitution of one or more amino acids, by extension at the N- and/or C-terminus with additional amino acids or functional groups, which may improve bio-availability, targeting to T-cells, or comprise or release immune modulating substances that provide adjuvant or (co)stimulatory functions.

The peptide to be reconstituted and/or comprised within the pharmaceutical composition may comprise or consist of a non-naturally occurring sequence as a result of the synthesis of non-natural lengths or as a result of comprising additional amino acids not originating from the protein antigen where the peptide is derived for and/or as a result of comprising a modified amino acid and/or a non-naturally occurring amino acid and/or a covalently linked functional group such as a fluorinated group, a fluorocarbon group, a human toll-like receptor ligand and/or agonist, an oligonucleotide conjugate, PSA, a sugar chains or glycan, a pam3cys and/or derivative thereof preferably such as described in WO2013051936A1, CpG oligodeoxynucleotides (CpG-ODNs), Cyclic dinucleotides (CDNs), a DC pulse cassette, a tetanus toxin derived peptide, a human HMGB1 derived peptide; either within the peptide or appended to the peptide, as indicated above. The peptide of the invention may comprise 2-aminoisobutyric acid (Abu, an isostere of cysteine). A cysteine of the peptide of the invention may be replaced by Abu.

Preferably, a peptide to be reconstituted and/or comprised within the pharmaceutical composition of the invention, is an isolated peptide, wherein "isolated" does not reflect the extent to which the peptide is purified, but indicates that the peptide has been removed from its natural milieu (i.e., that has been subject to human manipulation), and may be a recombinantly produced peptide or a synthetically produced peptide.

The use of relatively short peptides is highly preferred for medical purposes as these can be efficiently synthesized in vitro, which is not possible or uneconomical for native proteins larger than approximately 100, i.e. 95, 96, 97, 98, 99, 100, 101, 102, 103, 104, 105 amino acids. Chemical synthesis of peptides is routine practice and various suitable methods are known to the skilled person. Chemical synthesis of peptides also overcomes the problems associated with recombinant production of intact proteins, which is difficult to standardize and requires extensive purification and quality control measures. Peptides with a length that exceeds the length of human leukocyte antigen (HLA) class I and class II epitopes (e.g. having a length as specified herein for peptides to be reconstituted and/or comprised within the pharmaceutical composition of the invention) are particularly advantageous for use as vaccine component because they are large enough to be taken up by professional antigen presenting cells (APC), in particular Dendritic cell (DC), as explained in WO02/070006, and processed in the DC before cell surface presentation of the contained HLA class I-presented and HLA class II-presented epitopes takes place. Therefore, the disadvantageous induction of T cell tolerance by the systemic presentation of minimal HLA class I-presented epitopes on non-antigen presenting cells (as shown in Toes et al., *Proc Natl Acad Sci* (1996) USA 93(15):7855, and Toes et al., *Immunol* (1996) 156(10):3911), is prevented by the application of peptides exceeding the length of human leukocyte antigen (HLA) class I and class II epitopes (as shown in Zwaveling et al., *J. Immunol.* (2002) 169:350-358). As compared to vaccination with the peptides having a length as specified herein for peptides to be reconstituted and/or comprised within the pharmaceutical composition of the invention, therapeutic vaccination with full length proteins are likely to be less potent (Rosalia et al. *Eur. J. Immunol* (2013) 43: 2554-2565).

Peptides to be reconstituted and/or comprised in a pharmaceutical composition of the invention are preferably peptides of about 15 to about 100 amino acids in length, also denominated herein as long peptides, that each exceed the length of human leukocyte antigen (HLA) class I and class II presented epitopes and that either on its own or mixed induce a combined CD4+ and CD8+ T cell response that is therapeutically successful and inducing cure in a high percentage of patients. Preferably, the long peptides of the invention are synthetic peptides, denominated herein as synthetic long peptides (SLPs).

A "CTL epitope" is understood herein as a linear fragment of a polypeptide antigen that is liberated from the source protein by proteasome mediated proteolytic cleavage and subsequently presented by an HLA class I molecule on the cell surface of an antigen presenting cell (APC), preferably a human antigen presenting cell. A CTL epitope of the invention is preferably capable of activating a $CD8^+$ T cell response. A CTL epitope typically comprises at least 8 up to 12, or exceptionally up to 13 or 14 amino acids. Preferably a CTL epitope consists of 8-14 amino acids, i.e. has a length of at least 8 up to 14 amino acids.

A "Th-cell epitope" is understood herein to be a linear peptide fragment that is recognized by an HLA class II molecule. A Th-cell epitope is capable of inducing a $CD4^+$ T cell response. An HLA class II-restricted $CD4^+$ T-helper cell (Th-cell) epitope typically comprises 15 up to 20, or exceptionally even more, amino acids. Preferably, an HLA class II-restricted T-helper cell epitope comprises 10-20 or 10-15 amino acids.

Most preferably, the Th-cell epitope of the peptide to be reconstituted and/or comprises in the pharmaceutical composition of the invention, is capable of activating a $CD4^+$ T-helper memory and/or $CD4^+$ T-helper effector response, i.e. activation of a CD45RO-positive $CD4^+$ T-helper cell.

This will lead, by virtue of the 'license to kill' signal through CD40-triggering of DC (Lanzavecchia (1998) *Nature*, 393: 413) to a more robust CD8+ effector and memory cytotoxic T cell response. In another setting the activated CD4+ T-helper cells may activate non-HLA restricted killer cells of the immune system.

Within the context of the present invention "a peptide which comprises at most 100 consecutive amino acids from a protein antigen" means that the number of consecutive amino acids originating from the protein antigen and present in a peptide as defined herein, is 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, or 30 amino acids or less. Within the context of the present invention "a peptide which comprises at least 15 consecutive amino acids from a protein antigen" means that the number of consecutive amino acids originating from the protein antigen and present in a peptide as defined herein, is at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 or more amino acids. Within the context of the present invention "a peptide which comprises 15-100 consecutive amino acids from a protein antigen" means that the number of consecutive amino acids originating from the protein antigen and present in a peptide as defined herein, is at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 amino acids and no more than 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, or 30 amino acids. More preferably, the length of the contiguous amino acid sequence from the protein antigen comprised within the peptide to be reconstituted is 15-100 amino acids, or preferably 15-95 amino acids, or 15-90 amino acids, or 15-85 amino acids, or 15-70 amino acids, or 15-25 amino acids, or 15-60 amino acids, or 15-55 amino acids, or 15-50 amino acids, even more preferably 15-45 amino acids, even more preferably, 15-40 amino acids, even more preferably 17-39, even more preferably 19-43 amino acids, even more preferably 22-40 amino acids, even more preferably 28-40 and even more preferably 30-39 amino acids.

Preferably, the pharmaceutical composition according to the invention does not comprise any peptides which fulfill both of the following properties:

a. the percentage of basic amino acid residues equals the percentage of acidic amino acid residues, and b. the percentage of hydrophobic amino acid residues is 48% or higher.

For the purposes of this embodiment, amino acid residues are classified as "acidic", "basic", "hydrophobic" or "neutral" as follows:

| Amino acid | Category |
|---|---|
| Asp | Acidic |
| Glu | Acidic |
| Arg | Basic |
| Lys | Basic |
| His | Basic |
| Ala | Hydrophobic |
| Phe | Hydrophobic |
| Leu | Hydrophobic |
| Ile | Hydrophobic |

-continued

| Amino acid | Category |
|---|---|
| Val | Hydrophobic |
| Tyr | Hydrophobic |
| Trp | Hydrophobic |
| Cys | Neutral |
| Gly | Neutral |
| Met | Neutral |
| Pro | Neutral |
| Asn | Neutral |
| Gln | Neutral |
| Ser | Neutral |
| Thr | Neutral |

The peptides to be reconstituted and/or comprised within the pharmaceutical composition of the invention are preferably antigenic peptides. "Antigenic peptides" are to be understood herein as (highly) immunogenic and capable of inducing a potent combined antigen-directed CD4+ T helper and CD8+ cytotoxic T cell response, when administered as a vaccine composition to a subject, preferably a human or animal subject. The peptide may be predicted to be immunogenic and/or may be proven to be immunogenic using in vitro or ex vivo assays or by doing in vivo tests appreciated in the art to establish immunogenicity. Preferably, the peptide can be used effectively in the prevention, partial clearance and/or treatment or full clearance of an antigen related disease or condition in a subject, preferably as detectable by:

activation or an induction of the immune system and/or an increase in antigen specific activated CD4+ and/or CD8+ T-cells in peripheral blood or in tissues as established by Elispot assay or by tetramer staining of CD4+ or CD8+ T cells or an increase of the cytokines produced by these T-cells as established by intracellular cytokine staining of CD4+ and CD8+ T cells in flow cytometry after at least one week of treatment; and/or inhibition of proliferation of antigen related infection or a detectable decrease of antigen expressing cells or a decrease in cell viability of antigen expressing cells; and/or induction or increased induction of cell death of antigen expressing cells; and/or inhibition or prevention of the increase of antigen expressing cells.

In a preferred embodiment, a vaccine composition of the invention comprises a combination of peptides wherein said combination of peptides covers at least 70%, 80%, 90%, 92%, 94%, 95%, 96%, 97%, 98%, 99% or 100% of the HLA class I molecules that are encoded by HLA alleles predominant in the population of human subjects to be treated. HLA alleles that are predominant in the population of human subjects to be treated. Preferred HLA class I epitopes in peptides according to the invention are epitopes capable of binding to: HLA-A0101; HLA-A0201; HLA-A0206; HLA-A0301; HLA-A1101; HLAA2301; HLA-A2402; HLA-A2501; HLA-A2601; HLA-A2902; HLA-A3001; HLAA3002; HLA-A3101; HLA-A3201; HLA-A3303; HLA-A6801; HLA-A6802; HLAA7401; HLA-B0702; HLA-B0801; HLA-B1301; HLA-B1302; HLA-B1402; HLAB1501; HLA-B1502; HLA-B1525; HLA-B1801; HLA-B2702; HLA-B2705; HLAB3501; HLA-B3503; HLA-B3701; HLA-B3801; HLA-B3901; HLA-B4001; HLAB4002; HLA-B4402; HLA-B4403; HLA-B4601; HLA-B4801; HLA-B4901; HLAB5001; HLA-B5101; HLA-B5201; HLA-B5301; HLA-B5501; HLA-B5601; HLAB5701; HLA-B5801 and HLA-B5802. In a preferred embodiment, a peptide of the invention, covers at least 10%, 20%, 30%, 40%, 50%, 60%, 70%, 80%, 90%, or 100% of the HLA class I molecules that are encoded by HLA alleles predominant in the population of human subjects to be treated, wherein "Cover an HLA class I molecule" is understood herein as comprising a CTL epitope that shows binding affinity, preferably intermediate binding affinity, more preferably high binding affinity to said HLA class I molecule. Preferably, a peptide of the invention covers at least 10%, 20%, 30%, 40%, 50%, 60%, 70%, 80%, 90%, or 100% of group of HLA class I molecules consisting of: HLA-A0101; HLA-A0201; HLA-A0206; HLA-A0301; HLA-A1101; HLA-A2301; HLA-A2402; HLA-A2501; HLA-A2601; HLA-A2902; HLA-A3001; HLA-A3002; HLA-A3101; HLA-A3201; HLA-A3303; HLA-A6801; HLA-A6802; HLA-A7401; HLA-B0702; HLA-B0801; HLA-B1301; HLA-B1302; HLA-B1402; HLA-B1501; HLA-B1502; HLA-B1525; HLA-B1801; HLA-B2702; HLA-B2705; HLA-B3501; HLA-B3503; HLA-B3701; HLA-B3801; HLA-B3901; HLA-B4001; HLA-B4002; HLA-B4402; HLA-B4403; HLA-B4601; HLA-B4801; HLA-B4901; HLA-B5001; HLA-B5101; HLA-B5201; HLA-B5301; HLA-B5501; HLA-B5601; HLA-B5701; HLA-B5801 and HLA-B5802.

The reconstitution composition can be used for reconstituting a single type of peptides (i.e. all having substantially the same, or the same amino acid sequence) or for mixtures of different peptides having different amino acid sequences. A pharmaceutical composition of the invention preferably comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 and up to 33 different peptides. "Different peptides" are to be understood herein as having a different amino acid sequences, preferably having less than 60%, 50%, 40%, or preferably less than 30% sequence identity, as determined over their whole length. The different peptides to be reconstituted and/or comprised within the pharmaceutical composition of the invention may be peptides having a length as defined herein above that together overlap the entire amino acid sequence of the protein antigen from which these peptides are derived. However, in some instances, immunization with the complete set of overlapping (synthetic) long peptides spanning the full length protein antigens is not feasible, and a selection needs to be made. To narrow the number of peptides in a vaccine, preferably the most immunogenic long peptides are selected and incorporated that are recognized by the highest percentage of patients.

At least one of the peptides to be reconstituted and/or comprised within the pharmaceutical composition of the invention may have at least one cysteine residue that is capable of intermolecular disulfide bridging, or may have at least two cysteine residues that are capable of intra- and inter-molecular disulfide bridge formation. Preferably, a vaccine composition according to the invention comprises a combination of peptides wherein said combination of peptides covers at least 70%, 80%, 90%, 92%, 94%, 95%, 96%, 97%, 98%, 99% or 100% of the HLA class I molecules that are encoded by HLA alleles predominant in the population of human subjects to be treated as defined herein above.

The amount of peptides to be reconstituted in the reconstitution composition of the invention preferably is a pharmaceutical dosage unit and/or amount to be injected in a single volume, as defined herein above.

Dried peptides may be peptides free of further constituents but may also comprise buffer components such as Trifluor acetic acid (TFA), salts such as sodium, potassium or phosphate salts (e.g. NaCl, KCl and NaPO$_4$). The amount of further constituents is preferably less than 30%, more preferably less than 25%, of the total weight of the dry peptides to be reconstituted. Dried peptides to be reconstituted may be in a physical dried state as can be obtained by processes such as, but not limited to, rotor evaporation, lyophilization (freeze drying) and spray drying.

Preferred protein antigens, from which the peptides to be reconstituted and/or comprised within the pharmaceutical composition of the invention are derived, are defined herein below.

HPV-Derived Peptides

The peptides to be reconstituted and/or comprised within the pharmaceutical composition of the invention may be (mixes of) peptides derived from the early HPV antigen proteins E2, E6 or E7. Preferably, the contiguous amino acid sequence is selected from the full length amino acid sequences of the HPV E6 and E7 proteins from a high risk HPV serotype, such as serotypes 16, 18, 31, 33 or 45, more preferably from the amino acid sequences of the HPV E6 and E7 serotypes 16, 18, 31 or 33, most preferably from serotypes 16 or 18, of which 16 is most preferred. The amino acid sequence of the HPV serotype 16 E2 (UniProtKB-P03120), E6 (UniProtKB-P03126) and E7 (UniProtKB-P03129) proteins are depicted in SEQ ID NO: 14-16, respectively. The amino acid sequence of the HPV serotype 18 E2 (UniProtKB-P06790), E6 (UniProtKB-P06463) and E7 (UniProtKB-P06788) proteins are depicted in SEQ ID NO: 17-19, respectively.

Preferred peptides and peptide mixes to be reconstituted and/or comprised within the pharmaceutical composition of the invention and derived from HPV E6 and E7 proteins are as defined in WO00/75336 A2. Preferred peptides are peptides comprising or consisting of a contiguous sequence within an immunogenic region represented by any one of SEQ ID NO: 20-26.

Preferably, one or more peptides to be reconstituted and/or comprised within the pharmaceutical composition of the invention comprises a CTL epitope selected from the group represented by SEQ ID NO: 27-67.

Preferred peptides and peptide mixes to be reconstituted and/or comprised within the pharmaceutical composition of the invention and derived from HPV E2, E6 and E7 proteins are as defined in WO2002/070006 A2 and WO2002/090382, which is incorporated herein by reference. Preferred peptides are peptides comprising or consisting of a contiguous sequence within the following HPV immunogenic regions E2 (31-120); E2 (151-195); E2 (271-365); E6 (81-158); E7 (31-77), preferably of the HPV16 serotype and defined herein by SEQ ID NO: 68-72, respectively.

Preferably, one or more peptides to be reconstituted and/or comprised within the pharmaceutical composition of the invention comprises a Th epitope that is selected from DR1/E2 351-365, DR2/E2 316-330, DR2/E2 346-355, DR4/E2 51-70, E2 61-76, DQ6/E2 311-325, DR15/E7 50-62, DR3/E7 43-77, DQ2/E7 35-50 and DR1/E6 127-142 (represented herein by SEQ ID NO: 73-82, respectively).

Preferably, the peptides to be reconstituted and/or comprised within the pharmaceutical composition of the invention comprise at least one T cell epitope that is recognized by a T cell that infiltrates a cervical neoplastic lesion or by a T cell that is present in or isolated from a lymph node from the pelvic region, that is draining from the cervical neoplastic lesion. Preferably, the T cell epitope is present in or isolated from a draining lymph node comprising metastatic tumor cells. Such epitopes are disclosed in e.g., WO2008/147187 A1, US20060182762A1, WO2006013336A1, WO2009148230A2, WO2009148229A2, WO2002044384A2 which is incorporated herein by reference.

In yet a preferred peptide to be reconstituted and/or comprised within the pharmaceutical composition of the invention, the contiguous amino acid sequence comprises an epitope that is selected from the group consisting of a contiguous amino acid sequence selected from the group consisting of the amino acid sequences represented by SEQ ID NO: 83-104, which have been proven to be T-cell epitopes that are recognized by a T cells that infiltrates a cervical neoplastic lesion or by a T cell from a draining lymph node.

A preferred class II CD4⁺ Th cell epitope comprised in a peptide to be reconstituted and/or comprised within the pharmaceutical composition of the invention is selected from the group consisting a contiguous amino acid sequence selected from the group consisting of the amino acid sequences represented by SEQ ID NO: 83-99.

A preferred class I CD8⁺ CTL cell epitope comprised in a peptide to be reconstituted and/or comprised within the pharmaceutical composition of the invention is selected from the group consisting a contiguous amino acid sequence selected from the group consisting of the amino acid sequences represented by SEQ ID NO: 85, 82, 100-104.

Preferred peptides to be reconstituted and/or comprised within the pharmaceutical composition of the invention comprise or consist of a contiguous amino acid sequence selected from the group consisting of the amino acid sequences represented by SEQ ID NO: 1-13.

Preferred mixes of peptides to be reconstituted and/or comprised within a vaccine composition of the invention are mixes of peptides that have at least 1, 2, 3, 4 or 5 of the peptides comprising or consisting of the sequences selected from SEQ ID NO: 1-5; at least 1, 2, 3, 4, 5 or 6 of the peptides comprising or consisting of a contiguous amino acid sequence selected from the group consisting of the amino acid sequences represented by SEQ ID NO: 1-6; and at least 1, 2, 3, 4, 5, 6 or 7 of the peptides comprising or consisting of a contiguous amino acid sequence selected from the group consisting of the amino acid sequences represented by SEQ ID NO: 7-13. Preferably, the pharmaceutical composition comprises a mixture of peptides having sequence SEQ ID NO: 1-5 or SEQ ID NO: 1-6 or SEQ ID NO: 7-13. Preferably, the different peptides in the mixture are present in the pharmaceutical composition in substantially equal ratios.

HBV-derived Peptides

The peptides to be reconstituted and/or comprised within the pharmaceutical composition of the invention may be (mixes of) peptides derived from the various genotypes, e.g. from the HBV-A proteins, HBV polymerase (UniProtKB-P03159), HBV core protein (UniProtKB-P0C625), HBV X protein, and HBV large surface protein (UniProtKB-P03141), which are represented herein by SEQ ID NO: 105-108. Preferred peptides, peptides mixes and epitopes present within these peptides have been disclosed in e.g. WO2015/187009, WO2014/102540 A1, WO 93/03753, WO 95/03777, US2010/0068228A1, US2009/0311283 A1, which are incorporated herein by reference.

Preferred, one or more peptides to be reconstituted and/or comprised within the pharmaceutical composition of the invention comprise or consist of an amino acid sequence selected from the group consisting of SEQ ID NO: 109-146.

Preferably, the peptide to be reconstituted and/or comprised within the pharmaceutical composition of the invention comprises or consist of a peptide selected from the group consisting of SEQ ID NO: 109, 113, 118, 121, 122, 126, 129, 132, 133, 134, 135, 138 and 142, more preferably selected from the group consisting of SEQ ID NO: 109, 113, 118, 121, 122, 126, 129, 132, 133, 135, 138 and 142, even more preferably selected from the group consisting of SEQ ID NO: 113, 118, 121, 122, 126, 129, 132, 133, 134, 135 and 142, even more preferably selected from the group consisting of SEQ ID NO: 113, 118, 121, 122, 126, 129, 132, 133, 135 and 142, even more preferably selected from the group consisting of SEQ ID NO: 118, 121, 129, 132, 133 and 142, most preferably selected from the group of SEQ ID NO: 133, 142 and 121. Preferably, the one or more peptides to be reconstituted and/or comprised within the pharmaceutical composition of the invention comprises or consists of a peptide selected from the group consisting of SEQ ID NO: 109, 118, 121, 122, 126, 129, 132-135. Preferably, the one or more peptides to be reconstituted and/or comprised within the pharmaceutical composition of the invention comprises or consists of a peptide selected from the group consisting of SEQ ID NO: 122, 129 and 133.

Preferred mixes of peptides to be reconstituted and/or comprised within a vaccine composition of the invention are mixes of peptides at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 and up to 33 different peptides of the peptides consisting of or comprising of a peptide selected from the group consisting of SEQ ID NO: 109-146, more preferably selected from the group consisting of SEQ ID NO: 109, 113, 118, 121, 122, 126, 129, 132, 133, 134, 135, 138 and 142, more preferably selected from the group consisting of SEQ ID NO: 109, 113, 118, 121, 122, 126, 129, 132, 133, 135, 138 and 142, even more preferably selected from the group consisting of SEQ ID NO: 113, 118, 121, 122, 126, 129, 132, 133, 134, 135 and 142, even more preferably selected from the group consisting of SEQ ID NO: 113, 118, 121, 122, 126, 129, 132, 133, 135 and 142, even more preferably selected from the group consisting of SEQ ID NO: 118, 121, 129, 132, 133 and 142, most preferably selected from the group of SEQ ID NO: 133, 142 and 121. Further preferred is a composition that comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 and up to 33 different peptides of the peptides consisting of or comprising of a peptide selected from the group consisting of SEQ ID NO: 109, 118, 121, 122, 126, 129, 132-135, more preferably selected from the group consisting of SEQ ID NO: 121, 129 and 133. Further preferred mixes to be reconstituted and/or comprised within the pharmaceutical composition of the invention are a mix comprising a peptide that comprises or consists of a peptide of SEQ ID NO: 121 in combination with a peptide that comprises or consists of at least one of SEQ ID NO: 139, 140, 133, 139, 142, 118, 129; and a mix comprising a peptide that comprises or consists of a peptide of SEQ ID NO: 133 in combination with a peptide that comprises or consists of at least one of SEQ ID NO: 139, 140, 63, 139, 142, 118, 129. Preferably, the different peptides in the mixture are present in the pharmaceutical composition in substantially equal ratios.

PRAME-Derived Peptides

The peptides to be reconstituted and/or comprised within the pharmaceutical composition of the invention may be (mixes of) peptides derived from PRAME (UniProtKB-P78395), which is represented herein by SEQ ID NO: 147. Preferred peptides, peptides mixes and epitopes present within these peptides have been disclosed in e.g., WO 2008/118017 A2 which is incorporated herein by reference. Preferably, one or more of the peptides to be reconstituted comprise or consist a peptide selected from the group consisting of the amino acid sequence defined by SEQ ID NO: 148-167. Preferred mixes of peptides to be reconstituted and/or comprised within a vaccine composition of the invention are mixes at least 2, 3, 4, 5, 6, 7, 8, 9, 10, 11, 12, 13, 14, 15, 16, 17, 18, 19 or 20 different peptides selected from SEQ ID NO: 148-167.

Preferably, the one or more peptides to be reconstituted and/or comprised within the pharmaceutical composition of the invention comprises a Th epitope that is selected from SEQ ID NO: 168-169.

P53-Derived Peptides

The peptides to be reconstituted and/or comprised within the pharmaceutical composition of the invention may be (mixes of) peptides derived from P53 (e.g. UniprotKB P04637), which is represented herein by SEQ ID NO: 190. Preferred peptides, peptides mixes and epitopes present within these peptides have been disclosed in e.g., WO 2008/147186 A2, which is incorporated herein by reference. Preferably, one or more of the peptides to be reconstituted comprise or consist a peptide selected from the group consisting of the amino acid sequence defined by SEQ ID NO: 191-211, more preferably selected from the group consisting of the amino acid sequence defined by SEQ ID NO: 191-204.

Preferred mixes of peptides to be reconstituted and/or comprised within a vaccine composition of the invention are mixes at least 2, 3, 4, 5, 6, 7, 8, 9, 10, 11, 12, 13, 14, 15, 16, 17, 18, 19 or 20 different peptides selected from SEQ ID NO: 191-211.

PSMA-Derived Peptides

The peptides to be reconstituted and/or comprised within the pharmaceutical composition of the invention may be (mixes of) peptides derived from PSMA (e.g. UniprotKB Q04609), which is represented herein by SEQ ID NO: 212. Preferred peptides, peptides mixes and epitopes present within these peptides have been disclosed in e.g., WO 2013/006050 A1, which is incorporated herein by reference. Preferably, one or more of the peptides to be reconstituted comprise or consist a peptide selected from the group consisting of the amino acid sequence defined by SEQ ID NO: 213-232.

Preferred mixes of peptides to be reconstituted and/or comprised within a vaccine composition of the invention are mixes at least 2, 3, 4, 5, 6, 7, 8, 9, 10, 11, 12, 13, 14, 15, 16, 17, 18, 19 or 20 different peptides selected from SEQ ID NO: 213-232.

Also comprised within the preferred antigen proteins, peptides to be reconstituted and epitopes within these peptides are antigen proteins, peptides and epitopes that show substantial identity to any of the specific antigen proteins, peptides and epitopes defined herein. Sequence identity is herein defined as a relationship between two or more amino acid sequences (polypeptide or protein), as determined by comparing the sequences. In the art, "identity" also means the degree of sequence relatedness between amino acid sequences as determined by the match between strings of such sequences. Sequence identity can be determined by alignment of two peptide sequences using global or local alignment algorithms, depending on the length of the two sequences. Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, CA 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water', the default Gap opening penalty is 10.0 and the default gap extension penalty is 0.5; default scoring matrices are Blossum62 for proteins). When sequences have a substantially different overall length, local alignments, such as those using the Smith Waterman algorithm, are preferred.

Alternatively, percentage identity may be determined by searching against public databases, using algorithms such as FASTA, BLAST, etc. Thus, the protein sequences of the present invention can further be used as a "query sequence" to perform a search against public databases to, for example, identify other family members or related sequences. Such searches can be performed using the BLASTp and BLASTx programs (version 2.0) of Altschul, et al. (1990) *J. Mol. Biol.* 215:403-10. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25(17): 3389-3402. When utilizing BLAST and Gapped BLAST programs, the default parameters of the respective programs (e.g., BLASTx and BLASTp) can be used. See the homepage of the National Center for Biotechnology Information at http://www.ncbi.nlm.nih.gov/.

An antigen protein, peptide or epitope that show substantial identity to its related antigen protein, peptide or epitope defined herein is to be understood herein to have at least 70%, 75%, 80%, 85%, 90%, 91%, 92%, 93%, 94%, 95%, 96%, 97%, 98%, or 99% identity to any one of the specific sequences referred to herein, based on the full length of said specific sequence (i.e. over its whole length or as a whole).

Medical Use

Provided is a method for preventing or treating a persistent or chronic infection, pre-cancerous disorder and/or cancer. In other words, provided is the pharmaceutical composition of the invention as defined herein above for use as a medicament, preferably for the prevention or treatment of a persistent or chronic infection, pre-cancerous disorder and/or cancer. Such method or use comprises the step of administrating the pharmaceutical composition of the invention to a subject that is in need of such prevention and/or treatment. A subject in need of prevention and/or treatment may also be referred to as a patient, and may refer to an animal such as a mammal, including, but not limited to, a human or a non-human mammal, such as a non-human primate, bovine, equine, canine, ovine, or feline.

Preferably, a pharmaceutical dosage unit as defined herein above is provided. As also indicated herein above, this pharmaceutical dosage unit may be given once in a single shot or as multiple volumes administered at different locations. For example, a pharmaceutical dosage unit may be divided over two shots each administered in one of the two legs or arms of the subject to be treated. The two shots may comprise the same or different peptides mixes. For instance, a first shot may comprise SEQ ID NO 1-5 or SEQ ID NO: 1-6 and a second shot may comprise SEQ ID NOs 7-13, wherein both shots are administered at a single or substantially single time point, wherein substantially single time point is to be understood as within at most about 15 minutes, preferably, within at most 2 minutes.

The administration of the single or multiple shot may be carried out once or alternatively may be repeated subsequently, such as, but not limited to, daily, bi-weekly, weekly, once every two weeks, once every three weeks, once every four weeks, once every five weeks, once every six weeks, monthly, once per 2 months, once per 3 months, once per 4 months, once per 5 months, once per 6 months, once per 7 months, once per 8 months, once a year, once per 2 years, once per 5 years or once per 10 years.

Preferably, the pharmaceutical composition is administered in an effective amount as defined herein above. Preferably, the pharmaceutical composition of the invention is for intravenous or subcutaneous, or intramuscular administration, although other administration routes can be envisaged, such as mucosal administration or intradermal and/or intracutaneous administration or intratumoral administration, e.g., by injection. The pharmaceutical composition of the invention may be administered by a single administration. Alternatively, the administration may be repeated if needed and/or distinct peptides or peptide mixes or composition comprising different peptides or peptide mixes may be sequentially administered, wherein sequentially may be in time and/or location.

Preferably, the pharmaceutical composition is a vaccine composition for inducing a T cell response against at least one epitope comprised in a peptide. Preferably, the vaccine is for the prevention, partial clearance and/or treatment or full clearance of a antigen associated disease or condition in a subject, e.g. a persistent infection, cancerous (neoplasia) or precancerous disorder, preferably as detectable by:

activation or an induction of the immune system and/or an increase in antigen specific activated CD4+ and/or CD8+ T-cells in peripheral blood or in tissues as established by Elispot assay or by tetramer staining of CD4+ or CD8+ T cells or an increase of the cytokines produced by these T-cells as established by intracellular cytokine staining of CD4+ and CD8+ T cells in flow cytometry after at least one week of treatment; and/or inhibition of proliferation of antigen related infection or a detectable decrease of antigen expressing cells or a decrease in cell viability of antigen expressing cells; and/or induction or increased induction of cell death of antigen expressing cells; and/or inhibition or prevention of the increase of antigen expressing cells.

Examples of cancers to be prevented and/or treated via a method of the invention include, without limitation, cervical intraepithelial neoplasia (CIN), Vulvar intraepithelial neoplasia (VIN), vaginal intraepithelial neoplasia (VaIN), anal intraepithelial neoplasia (AIN), and penal intraepithelial neoplasia (PIN), as well as cancer of the cervix, vulva, vagina, anus, penis, aerodigestive track, and head & neck; liver cancer, leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, uterine cancer, testicular cancer, lung carcinoma, small cell lung carcinoma, non-small cell lung carcinoma, bladder carcinoma, multiple myeloma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

The method of the invention may be part of a combination therapy, which may be provided as a separate treatment or added to the pharmaceutical composition of the invention. The method of the invention may be combined with checkpoint control blockers, monoclonal antibodies (mAbs) targeting selected TNF receptor family members (e.g. CD40, 4-1 BB/CD137, OX-40/CD134, and CD27), immunosuppressive cytokines (e.g. IL-10, TGF-β and IL-6) and/or γC cytokines (e.g. IL-7, IL-15, and IL-21 or IL-2), IDO (indoleamine 2,3-dioxygenase) inhibitors, thalidomide and/or derivatives thereof, further immunomodulators (e.g. compounds that are known to deplete immunosuppressive Tregs and/or MDSCs), standard of care treatment, e.g. chemotherapy, radiotherapy, surgery, IFN-α conditioning, antiviral therapy, antibacterial therapy, UV therapy, anti-inflammatory therapy, etc. In case of the treatment or prevention of a pre-cancerous disorder or a cancer, the peptide-based vaccine may be combined with radiotherapy and/or chemotherapy such as treatment with carboplatin, paclitaxel, CarboTaxol (a combination of carboplatin, paclitaxel) and/or cisplatin. For example, the method of the invention may be part of a chemotherapy regimen wherein chemotherapy is applied once every three weeks. Preferably, a first pharmaceutical dosage unit of a pharmaceutical composition of the invention is administered 2 weeks after the second or third cycle of chemotherapy.

Method for Reconstitution

Also provided is a method for reconstituting dried, preferably lyophilized, peptides, comprising the following subsequent steps:

a) providing a vial comprising dried, preferably lyophilized, peptides;

b) thawing the peptides, preferably for about 5-30 min;

c) adding the reconstitution composition of the invention to the vial comprising the peptides, preferably without swirling the vial;

d) allowing to admix, preferably for about 0.5-5 minutes; and
e) swirling until a clear solution is obtained, preferably for about 1-3 minutes.

Preferably, steps b) to e) are performed at room temperature.

Further provided is a method for preparing a pharmaceutical composition, comprising the subsequent steps of:
(i) collect reconstituted peptides obtainable by the method for reconstituting dried peptides as defined above in a first syringe;
(ii) connect the first syringe of step (i) to a second syringe comprising the oil-based adjuvant using a connector;
(iii) push the content of the first syringe into the second syringe and backwards
(iv) repeat step (iii) about 10-50 times in a total in about 10-50 seconds.

Preferably, steps (i) to (iv) are performed at room temperature.

The clear solution obtained in step e) in the method for reconstituting dried peptides is to be understood herein as a reconstitution composition comprising reconstituted peptides, which can be used as starting material, i.e. as "reconstituted peptides" in step (i) of a method for preparing a pharmaceutical composition.

Preferably, the dried, preferably lyophilized, peptides in the vial and used as starting material in step a) in the method for reconstituting dried peptides, are peptides as defined herein above as peptides to be reconstituted and/or peptide to be comprised in the pharmaceutical composition of the invention. Preferably, said vial comprises peptides in an amount for injection as a single volume in a method for prevention and/or treatment, preferably a method of treatment and/or prevention as defined herein, i.e. a single pharmaceutical dosage unit, or part thereof in case of multiple injections at difference locations of the subjects body at substantially the same time point. Alternatively, the amount of dried peptides in the vial in step a) is exceeding the amount for injection as a single volume in said method. For instance, the amount of peptides within the vial may be twice the amount for injection as a single volume. In the latter case, half of the amount of reconstituted volume may be admixed with an amount of oil-based adjuvant in a method for preparing a pharmaceutical composition such as the pharmaceutical composition of the invention, in order to end up with a single volume of pharmaceutical composition for injection in a method or treatment or prevention, or, alternatively, the total amount of reconstituted volume may be admixed with an amount of oil-based adjuvant in order to end up with two volumes of pharmaceutical composition for injection.

Preferably, the peptides in step b) of the method to reconstitute peptides, are thawed at room temperature for about 5-30 min, or 10-30 min, such as for 5, 10, 15, 20, 25 or 30 minutes, or any value in between.

Preferably, the admixing in step d) of the method to reconstitute peptides, is without substantially swirling or stirring the vial preferably for about 0.5-2 minutes at room temperature, such as for 0.5, 1, 1.5 or 2 minutes. In other words, preferably the peptides in step d) is allowed to admix with the reconstitution composition while standing still.

The swirling in step e) of the method to reconstitute peptides, is performed by swirling until a clear solution is obtained. As indicated, this is performed preferably for about 1-3 minutes. However, for some peptides longer or shorter swirling time is required. However, a clear solution should preferably be obtainable within 20 minutes. Therefore, the swirling may be performed in a range from 1 to 20 min, from 1 to 10 min, from 1 to 5 minutes or from 1 to 3 minutes, such as 1, 2, 3, 4, 5, 6, 7, 8, 9, 10, 15 or 20 minutes, or any value in between, preferably until a clear solution is obtained upon visual inspection.

The reconstitution composition of step c) of the method for reconstituting peptides, and the oil-based adjuvant of step (ii) of the method for preparing a pharmaceutical composition, are as defined earlier herein. Preferably, the amount of reconstitution composition in step c) is in a range of from about 0.5 and 2 mL, preferably 1 mL. Preferably, the amount of reconstituted peptides in step (i) is the total amount of reconstituted peptides as obtained after step e), i.e. within the clear solution obtained after step e). However, optionally less is used, as exemplified above. Preferably, the volume of this reconstitution composition is admixed with oil-based adjuvant in step (ii) to (iv) in a ratio of about 2:1 to about 1:2, such as 2:1, 1.9:1, 1.8:1, 1.7:1, 1.6:1, 1.5:1, 1.4:1, 1.1:1, 1:1, 1:1.9, 1:1.8, 1:1.7, 1:1.6, 1:1.5, 1:1.4, 1:1.3, 1:1.2, or 1:1.1, preferably 1:1 of reconstitution composition: oil-based adjuvant.

The connector in (ii) may be any connector suitable in the art to connect two syringes that allow fluids to be exchanged between the two syringes, such as but not limited to, T and I connectors. The repeats (iv) may be about 10-50 times, such as, but are not limited to, 10, 15, 20, 25, 30, 45, 50 times, or any value in between.

Kit of Parts

Further, provided is a kit of parts comprising a:
1. a first vial containing dried, preferably lyophilized, peptides, wherein preferably the peptides are peptides as defined herein above;
2. a second vial containing a reconstitution composition of the invention; and, optionally,
3. a third vial containing an oil-based adjuvant, preferably as defined herein above.

Preferably, the all components, i.e. dried peptides, reconstitution composition and oil-based adjuvant, are sterile and/or pharmaceutical-grade or clinical-grade. Preferably, these components are manufactured using Good manufacturing practice (GMP) and have GMP quality as defined by both the European Medicines Agency and the Food and Drug Administration.

Preferably, the first vial is stored at a temperature at which the reconstitution composition is stable for at least 1 month, 2 months, 3 months, 6 months or 1 year or even 2 years. Preferably, said temperature is between −25° C. and 25° C., or between −23° C. and −18° C., or between 0° C. and 10° C., or between 2° C. and 8° C., or between 18° C. and 23° C. Preferably, the second vial is stored at a temperature at which the reconstitution composition is stable for at least 1 month, 2 months, 3 months, 6 months or 1 year or even 2 years. Preferably, said temperature is between −25° C. and 25° C., or between −23° C. and −18° C., or between 0° C. and 10° C., or between 2° C. and 8° C., or between 18° C. and 23° C. . . . Preferably, the third vial is stored at a temperature at which the reconstitution composition is stable for at least 1 month, 2 months, 3 months, 6 months or 1 year or even 2 years. Preferably, said temperature is between −25° C. and 25° C., or between −23° C. and −18° C., or between 0° C. and 10° C., or between 2° C. and 8° C., or between 18° C. and 23° C. Preferably, the first, second and third vial are stored at the same temperature.

Optionally, said kit of parts further comprises a manual describing the method for reconstituting dried peptides as defined herein above, storage conditions, a method for preparing a pharmaceutical composition as defined herein above and/or a manual for storing the first, second and/or third vial. In addition, the kit of parts may comprise a manual for administering the pharmaceutical composition to be prepared. Preferably, the volume of the first, second and/or third vial is at most 50 mL, preferably between 0.1 and 10 mL, preferably between 1 and 10 mL, such as, 0.5, 1, 2, 3, 4, 5 or 10 mL, or any value in between. A vial is to be understood herein as a container that can have any shape. Optionally a vial is to be understood herein as a syringe. Optionally, the first vial can be connected via a connector by an active handling process to the second vial to allow the reconstitution composition to contact and dissolute the peptides. Optionally, the second vial can subsequently be connected to the third vial to allow the reconstitution composition comprising the peptides to be admixed with the oil-based adjuvant. Optionally, the kit of parts further comprises one or more connectors, such as a T-connector, and/or an injection unit, such as a needle. Preferably, the amount of peptides in the first file, the amount of reconstitution composition in the second file and/or the amount or oil-based adjuvant in the third file are as defined in the method for reconstituting peptides and/or the method for preparing a pharmaceutical composition as defined earlier herein.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 0.1% of the value.

The sequence information as provided herein should not be so narrowly construed as to require inclusion of erroneously identified bases. The skilled person is capable of identifying such erroneously identified bases and knows how to correct for such errors.

All patent and literature references cited in the present specification are hereby incorporated by reference in their entirety.

BRIEF DESCRIPTION OF THE DRAWINGS

FIGS. 1A-1C show UPLC chromatograms of DP-6P (comprising SLPs represented by SEQ ID NOs: 1-6) in three different solvent mixtures, two hours after dissolution and storage at room temperature. (FIG. 1A) DP-6P (2.40 mg total peptide) dissolved in a mixture of 750 µL 0.1M Citric acid in water, 62.5 µL Propylene Glycol, 125 µL Ethanol and 62.5 µL Cremophor EL; (FIG. 1B) DP-6P (2.40 mg total peptide) dissolved in 20% v/v DMSO/water; (FIG. 1C) DP-6P (2.40 mg total peptide) dissolved in 20% v/v DMSO/water with 10 mM DTT.

FIGS. 2A-2D show UPLC chromatograms of DP-6P (comprising SLPs represented by SEQ ID NOs: 1-6) in two different solvent mixtures and at two time points after dissolution (t=0 and t=2 h). Both solvent mixtures contain Propylene Glycol, Ethanol, water and stabilizing or reducing agents. (FIG. 2A) DP-6P (2.40 mg total peptide) dissolved in a mixture of 600 µL water, 267 µL Propylene Glycol, 133 µL Ethanol and 1 mg/mL Ascorbic acid at t=0 (FIG. 2B) DP-6P (2.40 mg total peptide) dissolved in a mixture of 600 µL WFI, 267 µL Propylene Glycol, 133 µL Ethanol and 1 mg/mL Ascorbic acid at t=2 h; (FIG. 2C) DP-6P (2.40 mg total peptide) dissolved in a mixture of 750 µL 0.1M Citric acid in water, 62.5 µL Propylene Glycol, 125 µL Ethanol and 62.5 µL Cremophor EL at t=0; (FIG. 2D) DP-6P (2.40 mg total peptide) dissolved in a mixture of 750 µL 0.1M Citric acid in water, 62.5 µL Propylene Glycol, 125 µL Ethanol and 62.5 µL Cremophor EL at t=2 h.

(FIG. 3A) DP-6P (2.40 mg total peptide) dissolved in the solvent mixture comprising Tween20 at t=0; (FIG. 3B) DP-6P (2.40 mg total peptide) dissolved in the solvent mixture comprising Tween20 at t=2 h; (FIG. 3C) DP-6P (2.40 mg total peptide) dissolved in the solvent mixture comprising Cremophor EL at t=0; (FIG. 3D) DP-6P (2.40 mg total peptide) dissolved in the solvent mixture comprising Cremophor EL at t=2 h.

FIGS. 4A-4D show UPLC chromatograms of DP-6P (comprising SLPs represented by SEQ ID NOs: 1-6) and DP-7P (comprising SLPs represented by SEQ ID NOs: 7-13) after reconstitution and emulsification with Montanide ISA 51 VG. The solvent mixture for reconstitution contains per mL 750 µL 0.1M Citric acid in water, 62.5 µL Propylene Glycol, 125 µL Ethanol and Cremophor EL (62.5 µL). Prior to analysis, peptides were extracted from the emulsion by adding an excess of the solvent mixture and forcing phase separation by centrifugation. (FIG. 4A) DP-6P (2.4 mg total peptide) dissolved in 1 mL solvent mixture comprising Cremophor EL at t=0 (immediately after vaccine preparation and extraction); (FIG. 4B) DP-6P (2.4 mg total peptide) dissolved in 1 mL solvent mixture comprising Cremophor EL at t=2 h (after 2 hours storage of the vaccine product, followed by extraction). (FIG. 4C) DP-7P (2.8 mg total peptide) dissolved in 1 mL solvent mixture comprising Cremophor EL at t=0 (immediately after vaccine preparation and extraction); (FIG. 4D) DP-7P (2.8 mg total peptide) dissolved in 1 mL solvent mixture comprising Cremophor EL at t=2 h (after 2 hours storage of the vaccine product, followed by extraction).

(FIG. 6A) three independent (repeated) preparations (prep1, prep2 and prep3) at t=0, indicating the robustness of the emulsification method. (FIG. 6B) Two independent (repeated) preparations at t=0 (prep1t0 h and prep1t2 h) and t=2 h (prep2t0 h and prep2t2 h), demonstrating both robustness of the emulsification method as well as in-use physical stability of the emulsion for at least 2 hours at room temperature.

Figure 8A:
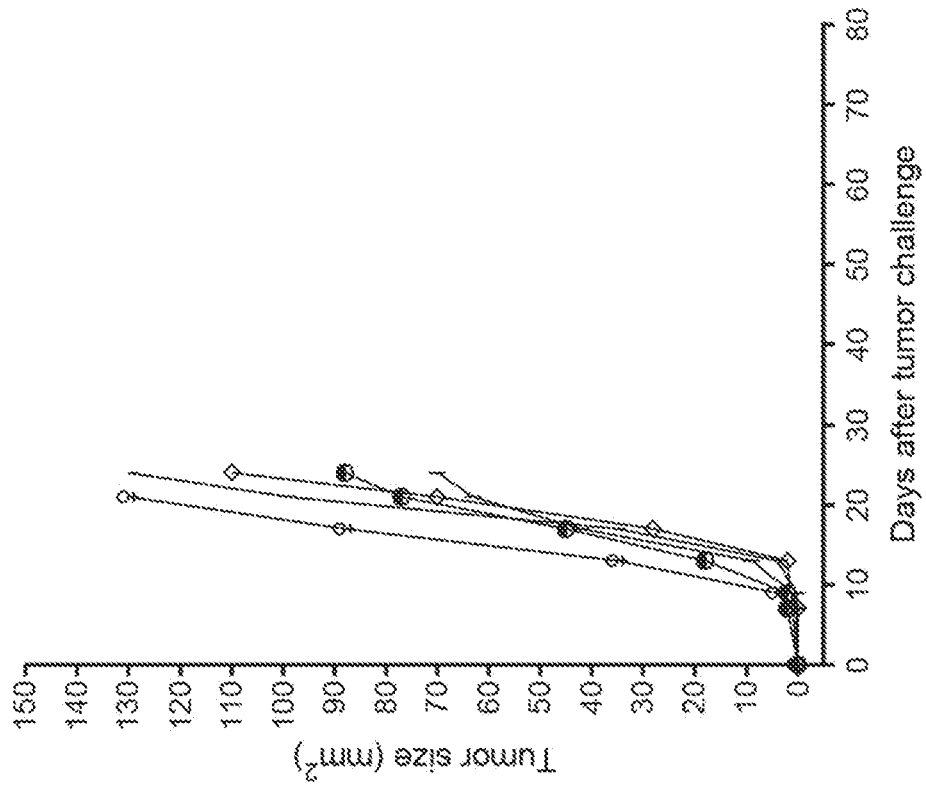
FIGS. 8A-8D show outgrowth of TC-1 tumors in mice vaccinated with either (FIG. 8A) 40% v/v DMSO/WFI emulsified 1:1 with Montanide only (DMSO), (FIG. 8B)
Figure 8B:
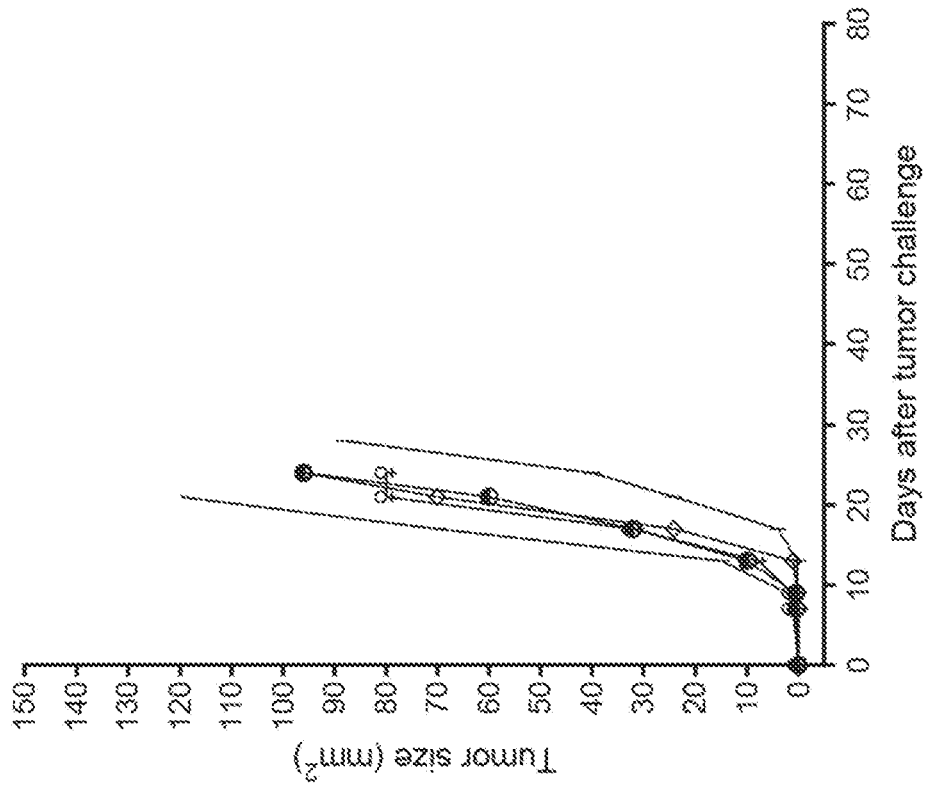
Figure 8D:
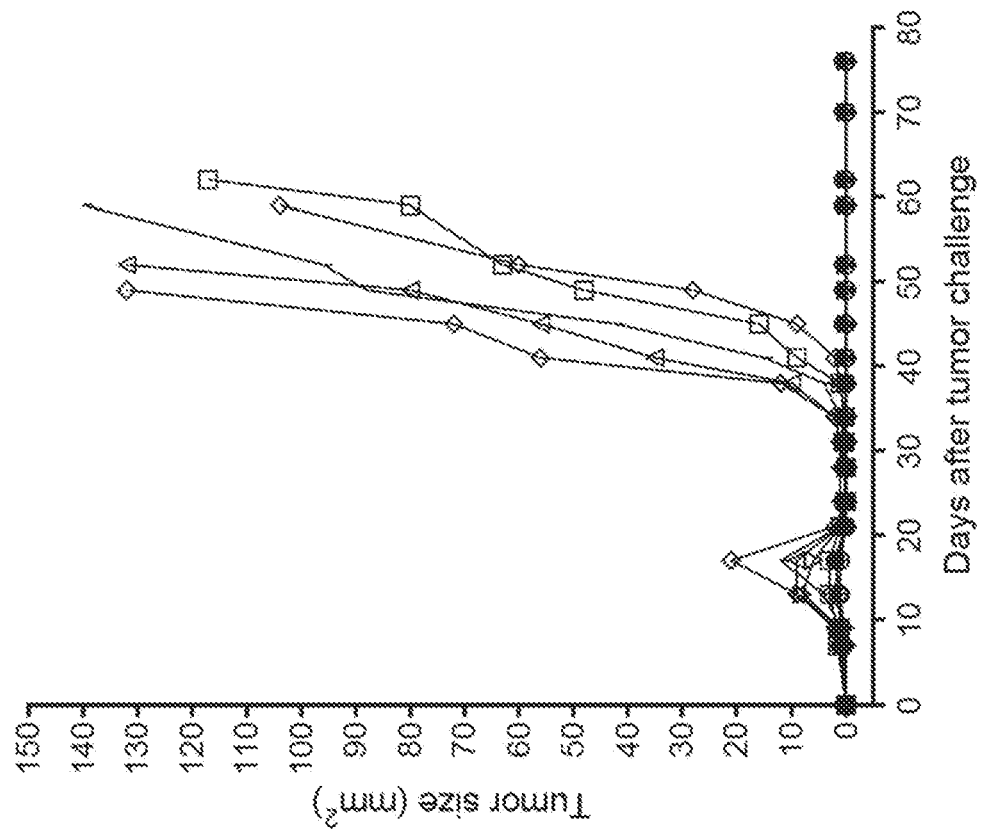
Figure 8C:
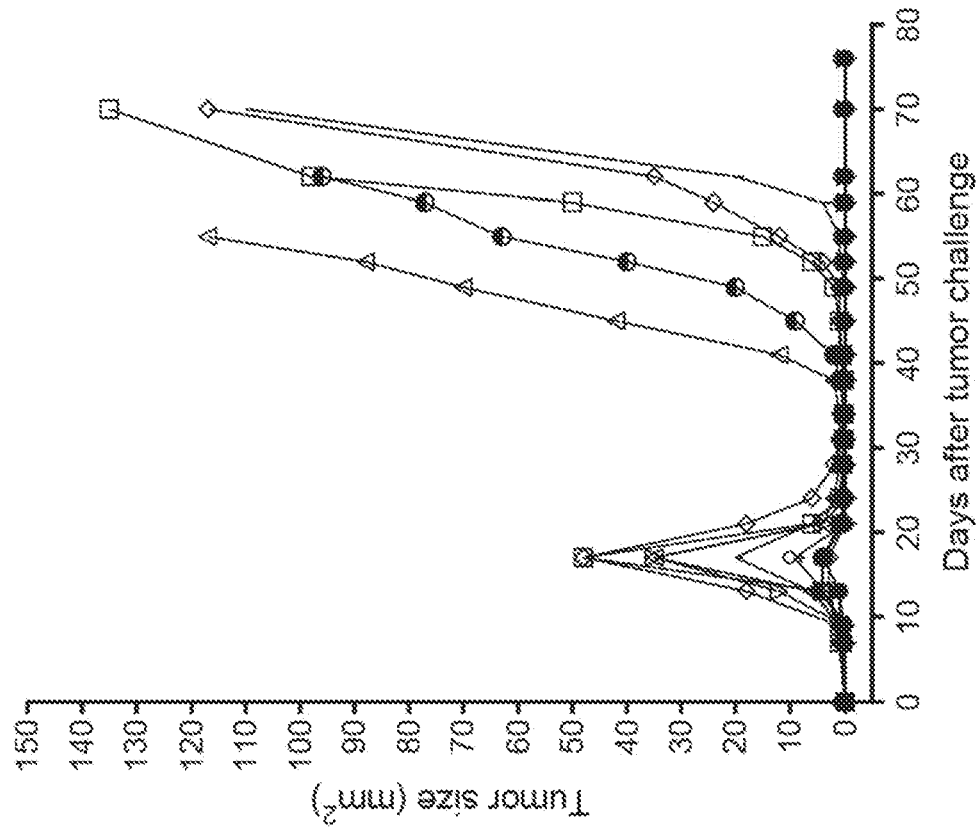

Reconstitution (Rec.) composition (750 µL 0.1M Citric acid in water, 62.5 µL Propylene Glycol, 125 µL Ethanol and 62.5 µL Cremophor EL) emulsified 1:1 Montanide only (Rec. composition), or with (FIG. 8C) SLP represented by SEQ ID NO: 6 and CpG ODN1826 dissolved in 40% v/v DMSO/ WFI emulsified 1:1 with Montanide (DMSO+SLP) or (FIG. 8D) SLP represented by SEQ ID NO: 6 and CpG ODN1826 dissolved in Reconstitution (Rec.) composition (750 µL 0.1M Citric acid in water, 62.5 µL Propylene Glycol, 125 µL Ethanol and 62.5 µL Cremophor EL) emulsified with 1:1 Montanide (Rec. composition+SLP).

Figure 9A:
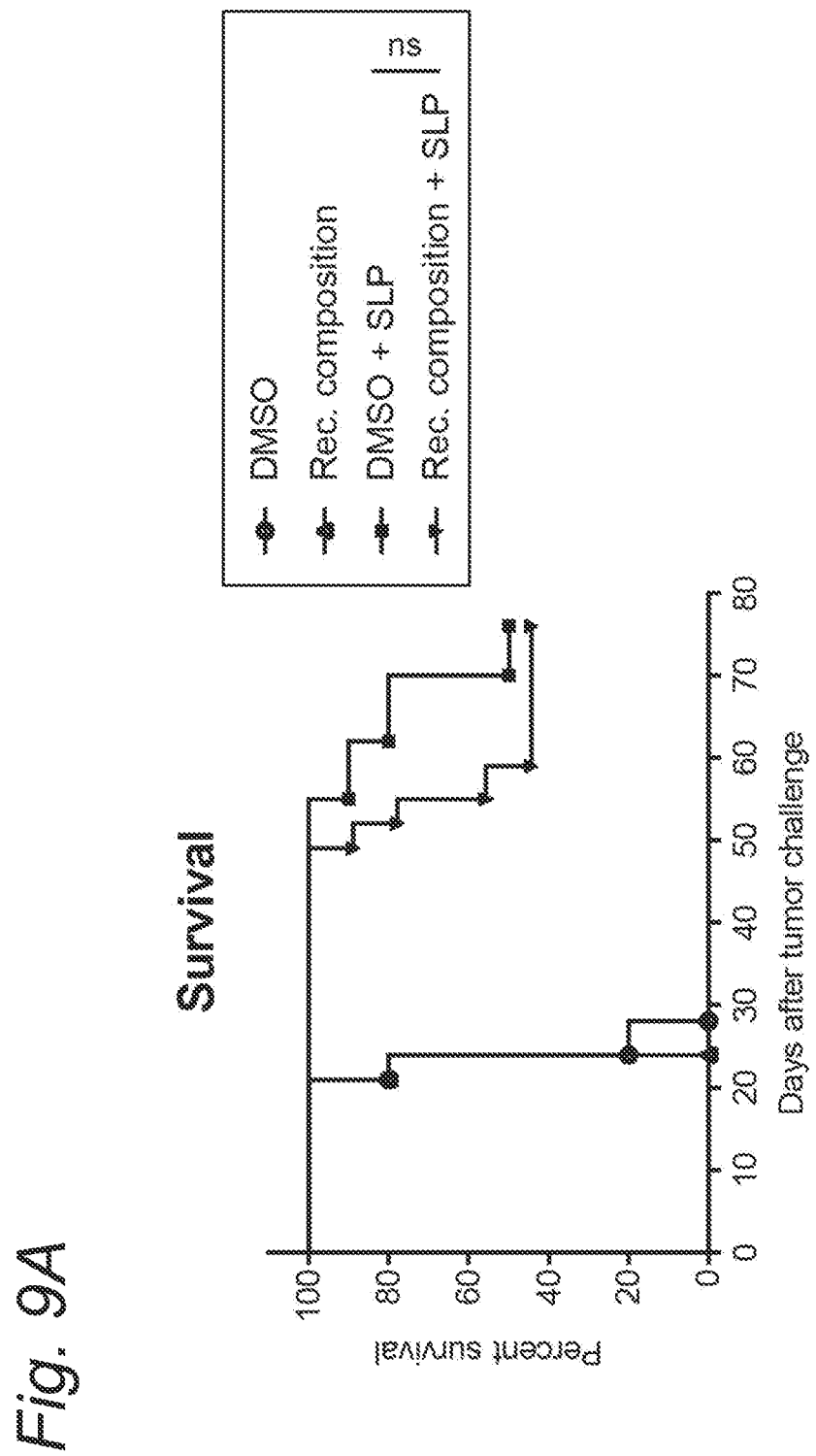
Figure 9B:
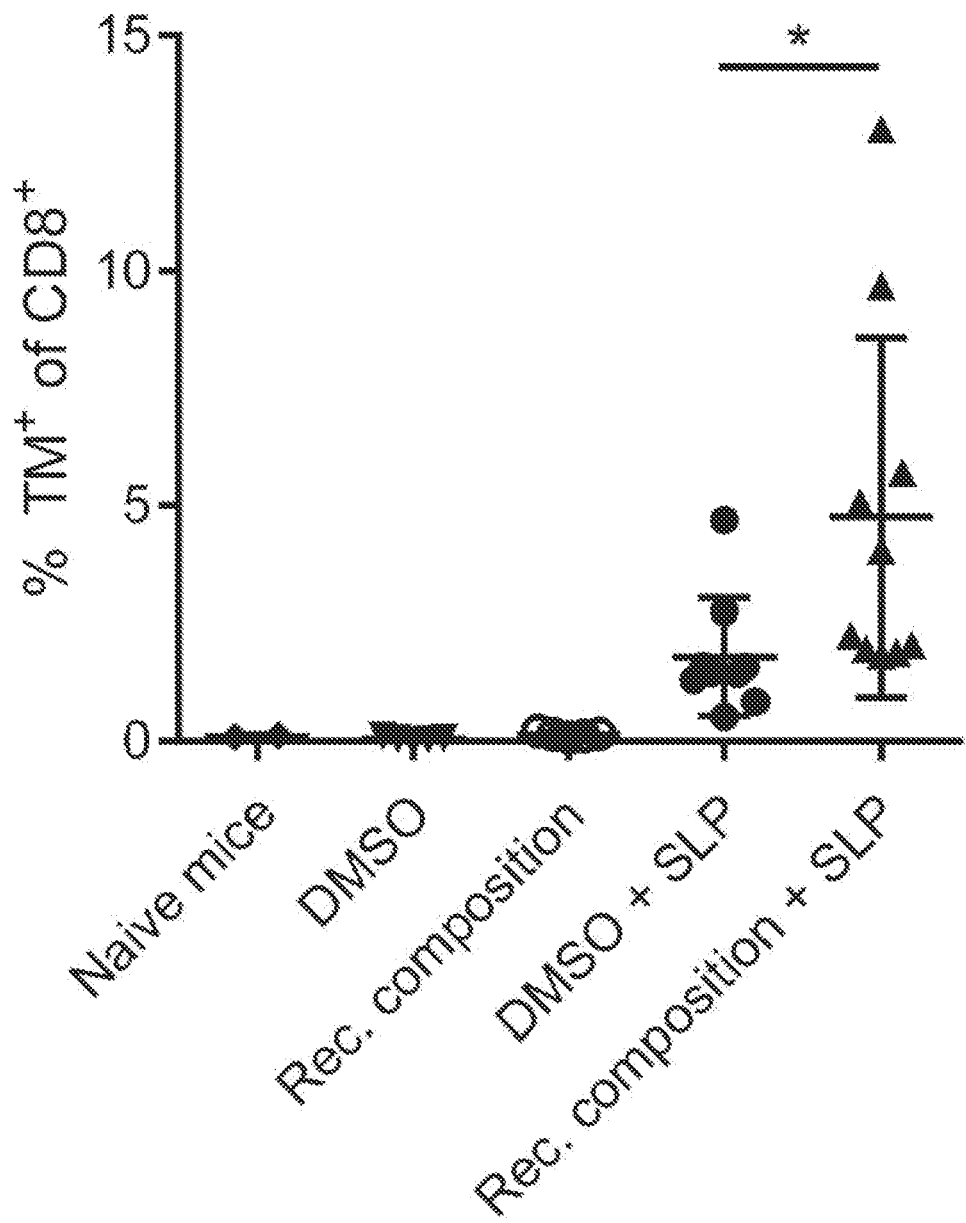

FIGS. 9A-9B show Kaplan-Meier plot (survival) (FIG. 9A) and percentage of induced $D^b$-RAYNIVTF (tetramer) positive CD8$^+$ T cells (FIG. 9B) of Group 1 mice challenged with TC-1 tumors and subsequently vaccinated with 40% v/v DMSO/WFI emulsified 1:1 with Montanide only (DMSO), Group 2 mice challenged with TC-1 tumors and subsequently vaccinated with Reconstitution composition (750 µL 0.1M Citric acid in water, 62.5 µL Propylene Glycol, 125 µL Ethanol and 62.5 µL Cremophor EL) emulsified 1:1 with Montanide only (Rec. composition), Group 3 mice challenged with TC-1 tumors and subsequently vaccinated with SLP represented by SEQ ID NO: 6 and CpG ODN1826 dissolved in 40% v/v DMSO/WFI emulsified 1:1 with Montanide (DMSO+SLP) and Group 4 mice challenged with TC-1 tumors and subsequently vaccinated with SLP represented by SEQ ID NO: 6 and CpG ODN1826 dissolved in Reconstitution composition (750 µL 0.1M Citric acid in water, 62.5 µL Propylene Glycol, 125 µL Ethanol and 62.5 µL Cremophor EL) emulsified 1:1 with Montanide (Rec. composition+SLP). Asterisk indicates significant difference (unpaired t-test, p=0.022); ns indicates non-significant difference (p=0.21).

Figure 10A:
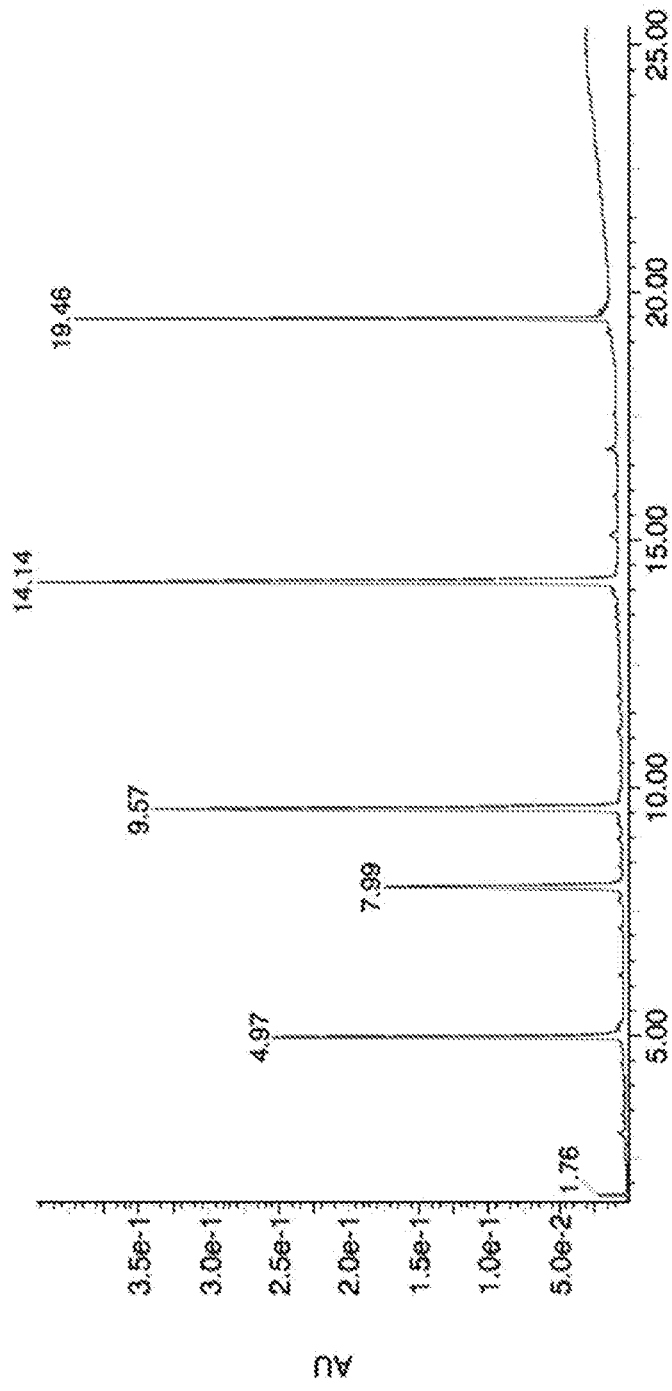
Figure 10B:
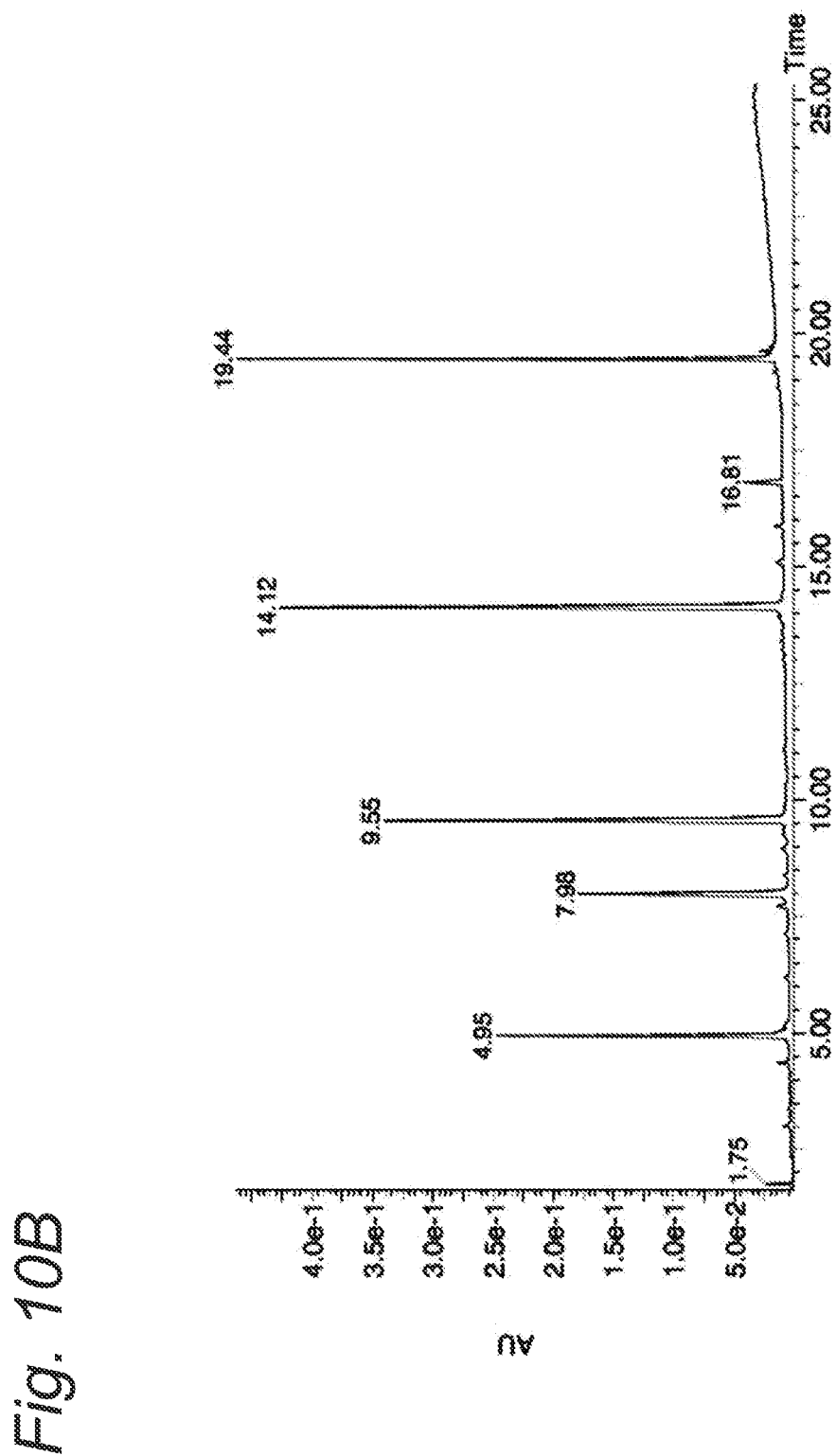

FIGS. 10A-10B show UPLC chromatograms of P53 DP-5P (comprising SLPs represented by SEQ ID NO: 191, 193, 194, 201 and 203). P53 DP-5P was reconstituted with a solvent mixture containing per mL 750 µL 0.1M Citric acid in water, 62.5 µL Propylene Glycol, 125 µL Ethanol and Cremophor EL (62.5 µL). Prior to analysis, the peptides were extracted from the final product emulsion by adding an excess of the solvent mixture and forcing phase separation by centrifugation. (FIG. 10A) P53 DP-5P (2.0 mg total peptide) dissolved in 1 mL solvent mixture comprising Cremophor EL at t=0 (immediately after vaccine preparation and extraction); (FIG. 10B) P53 DP-5P (2.0 mg total peptide) dissolved in 1 mL solvent mixture comprising Cremophor EL at t=2 h (after 2 hours storage of the vaccine product, followed by extraction).

EXAMPLES

Example 1

Introduction

The aim of this study was to find a suitable reconstitution method for a multipeptide HPV vaccine product involving dissolution of the peptide Drug Products HPV-DP-6P and HPV-DP-7P, followed by emulsification with Montanide ISA51VG. Previous studies have shown that in DMSO/WFI formulations, peptides containing one or more cysteine residues have a strong tendency to form disulfides. To improve the chemical stability of the Drug Products and prevent disulfide formation of the peptides, a new DMSO-free reconstitution solution was developed for reconstitution of both Drug Products. This new reconstitution solution should be able to dissolve the Drug Product and result in a stable emulsion with Montanide ISA51VG. Disulfide-formation should be minimal.

The study consists of four levels of analysis:
1. Screening for a suitable solvent combination to reconstitute the Drug Products, monitoring dissolution of the peptides by visual inspection.
2. Monitoring of the emulsion stability of the Drug Product emulsion with Montanide. Stability is assessed by visual inspection and by analysis of particle size of the emulsion droplets.
3. Analysis of the chemical stability of the Drug Product after reconstitution in solvents that were successful on level 1 and 2.
4. Analysis of the chemical stability of the Drug Product after reconstitution and emulsification, using solvents that were successful in level 1, 2 and 3. For this purpose, the peptides are dissolved, emulsified with Montanide ISA 51 VG, followed by extraction from the emulsion and analysis of the peptide composition.

Materials

The following lyophilized peptide compositions were used: DP-5P comprising peptides represented herein by SEQ ID NO: 1-5 admixed at equal net weights of 0.40 mg of each peptide per vial (total amount of protein per vial being 2.00 mg) and 0.56 mg TFA per vial; DP-6P comprising peptides represented herein by SEQ ID NO: 1-6 admixed at equal net weights 0.40 mg of each peptide per vial (total amount of protein per vial being 2.40 mg) and 0.67 mg TFA per vial; and DP-7P comprising peptides represented herein by SEQ ID NO: 7-13 admixed at equal net weights of 0.40 mg of each peptide per vial (total amount of protein per vial being 2.80 mg) and 0.96 mg TFA per vial.

The following chemicals were used: Cremophor EL, (Sigma Aldrich, Kolliphor EL, C5135); Propylene Glycol or PG (≥99.5%, Sigma Aldrich, W294004) Ethanol or EtOH (Absolute, VWR Emprove® Ph Eur, BP, USP. Article #1.00986.1000); Citric acid or CA (≥99%, Sigma Aldrich C1909); MilliQ water (from EQP-063); Sterile Montanide ISA 51VG (SEPPIC, batch #14V011).

The following equipment was used: Syringe extrusion devices (Discofix-3 T-connector, B. Braun); DMSO-resistant syringes (2 mL NORM-JECT Luer Lock, Henke Sass Wolf); Waters UPLC/MS system; Malvern Mastersizer 2000; Protein Simple MFI 5200 flowcell.

Methods

Dissolution

Reconstitution composition was prepared by mixing the organic and aqueous solvents before adding them to the lyophilized Drug Product. 1 mL of various reconstitution compositions was added to the Drug Product and the mixture was allowed to stand for 5 minutes, while swirling the solution several times. Physical stability was assessed by visual inspection. Chemical stability was assessed using UPLC/MS (see below under Chemical stability of the Drug Product solution).

Emulsification with Montanide

Solvent combinations resulting in a visually clear Drug Product solution were used in emulsification experiments with Montanide ISA51 VG. Unless stated otherwise, reconstitution and emulsification was performed according to the protocol in Table 1. Where indicated, mixing of the contents of syringe A and B was performed differently. These adaptations of the procedure in Table 3 are indicated in the results section in Table 4 and Table 5.

TABLE 1

Reconstitution and emulsification of drug product (DP).

| Step | Description |
|---|---|
| 1 | At least 10 minutes and maximum 30 minutes before start formulation, thaw at room temperature 1 vial with DP, lyophilized powder for injection. Record time of removal from the freezer (hh;min). |
| 2 | Collect 1 mL reconstitution composition in a 2 mL syringe. |
| 3 | Record time of starting the reconstitution (hh;min). |
| 4 | Add the content of the syringe containing sterile reconstitution composition (1 mL) to the DP vial. Do not swirl the vial. Remove the syringe from the vial. |
| 5 | Allow the mixture to stand for 2 minutes at RT, followed by gentle swirling for 3 minutes. If the content of the vial is not completely dissolved, vortex for 30 seconds. |
| 6 | Collect the contents of the vial (1.0 mL) in a new syringe (syringe A). |
| 7 | Collect 1.0 mL Montanide ISA 51 VG in a third 2 mL syringe (syringe B). |
| 8 | Remove one of the white caps of the T-connector and firmly attach the syringe containing the peptide solution in reconstitution composition (1.0 mL) to the connector (Syringe A). |
| 9 | Remove the second white cap of the T-connector and attach the syringe containing 1.0 mL Montanide ISA 51 (Syringe B) to the connector. |
| 10 | Turn the switch-key and push the content of syringe A first slowly into syringe B and then from syringe B to A. This is 1 cycle. Start the stopwatch. Repeat the cycle in total 50 times 40-50 seconds. Record number of seconds (to be documented by second operator). |
| 11 | Collect the vaccine emulsion in one syringe. Remove the syringe from the T-connector and place a clean needle on the syringe. |

Laser Diffraction Experiments for Testing Emulsion Stability

Emulsion stability was monitored both by visual inspection and by analysis of the particle size distribution using a Malvern Mastersizer 2000.

For particle size analysis, dilution of the emulsion was performed either with water or with a 0.01 M citric acid in water solution to obtain the desired level of obscuration. Montanide was admixed with the reconstitution composition comprising reconstituted DP using a stirrer at a speed of 1750 rpm and a refractive index of 1.46 were applied. Particle size distribution was expressed in D(0.5) and D(0.9) for a volume-based distribution.

Micro Flow Imaging (MFI) for Testing Emulsion Stability

As a second technique for particle size analysis for assessing emulsion stability, Micro Flow Imaging was used. Prior to analysis, a dilution of the emulsion was prepared by adding one droplet of emulsion to 10 mL 0.01M aqueous citric acid solution and mixing until homogeneous, followed by 1:100 dilution of this solution in water. Samples were measured in a purge volume of 0.20 mL for the duration of 0.68 minutes or per 1 million particles in one single run. The results are expressed in Equivalent Circle Diameter (ECD).

Chemical Stability of the Drug Product Solution

For samples showing complete dissolution and an emulsion stability of >2 hours, the chemical stability of the Drug Product solutions (without additional dilution) was monitored with UPLC/MS on a Waters Acquity UPLC system coupled to a Waters TQD mass spectrometer using a Waters Acquity column (type: BEH130, C18, 1.7 µm, 2.1×150 mm). Data processing was performed with Masslynx 4.1 software. UV-detection was performed at 220 nm and the mobile phase was 0.05% TFA and 1% ACN in water (buffer A) and 0.05% TFA in ACN (buffer B) at a flowrate of 0.3 mL/min. The column temperature was 65° C. and the autosampler temperature was 5° C. An injection volume of 5 µL was used, and the gradient profile of Table 2 was applied.

UV-detection was performed during the full length of the gradient, and mass spectrometric analysis was performed from 2-30 min in the positive mode.

For analysis of chemical stability of the Drug Product solutions, samples were analyzed at various time points, at least up to 2 hours after dissolution.

TABLE 2

Gradient profile for UPLC/MS.

| Time (min) | Eluent A (%) | Eluent B (%) |
|---|---|---|
| 0 | 87 | 13 |
| 0.5 | 87 | 13 |
| 5.5 | 79.5 | 20.5 |
| 17.0 | 68 | 32 |
| 22.8 | 45 | 55 |
| 28.5 | 45 | 55 |
| 28.6 | 20 | 80 |
| 30.0 | 20 | 80 |
| 30.1 | 87 | 13 |
| 33.0 | 87 | 13 |

In-Use Chemical Stability of HPV-DP-6P and HPV-DP-7P Vaccine Emulsions

For samples showing complete dissolution, an emulsion stability of >2 hours, and a chemical stability of the Drug Product solutions (without additional dilution) of >2 hours, the in-use chemical stability of the vaccine emulsions with Montanide ISA 51 VG was monitored with UPLC/MS. For analysis of chemical stability of the reconstituted and emulsified Drug Products, samples were analyzed at various time points, at least up to 2 hours after dissolution. UPLC/MS analysis was performed according to the method describe above for chemical stability of the Drug Product solution, using an extra sample preparation step for extraction of the peptides from the vaccine emulsion. For sample preparation of emulsified products, the following steps were applied:

- Take 300 µL Reconstitution Solution and add this to a 15 mL Greiner tube
- Add 100 µL heptane
- Add 200 µL of the Drug Product emulsion. Pipet the solution up and down three times.
- Vortex the mixture for 30 seconds
- Centrifuge the mixture for 5 minutes at 4400 rpm to obtain a two-phase system
- With a 20-200 µL pipette, take a 100 µL sample from the bottom layer and transfer to a total recovery UPLC vial.
- Analyze with UPLC/UV/MS according to the method described for chemical stability of the Drug Product solutions.

Results

Solvent Screening for Reconstitution and Emulsification

Solvents were screened to define a reconstitution composition comprising both an aqueous and organic fraction that is suitable for reconstituting lyophilized peptides and forming a chemically and physically stable emulsion with Montanide. All experiments below were performed with DP-6P. The experiments were verified using DP-5P and DP-7P, but as data were highly comparable, only the data on DP-6P are shown here. Physical stability of the reconstituted proteins and emulsion in this screen was assessed by visual inspection.

As organic fraction, a wide variety of organic solvents was tested. The only single organic solvent capable of completely dissolving DP-6P when admixed with WFI (water for injection) was NMP (Table 3). However, no stable emulsion with Montanide could be obtained when using NMP/WFI as reconstitution composition. The use of saline instead of WFI slightly improved the emulsion stability, but still no emulsions with a stability of ≥2 h could be obtained in a reproducible manner.

TABLE 3

Solvent screening for dissolution of DP-6P.

| Aqueous | Organic 1 | Peptides solubility | Emulsion stability |
|---|---|---|---|
| 600 µL WFI | 400 µL Glycerol | Particles | NA |
| 600 µL WFI | 400 µL PG | Clear viscous solution | NA |
| 600 µL WFI | 400 µL EtOH | Particles | NA |
| WFI | 100-20% DMF | Particles | NA |
| 800 µL WFI | 200 µL NMP | Clear solution | homogeneous < 1 h |
| 800 µL WFI, 0.9% NaCl | 200 µL NMP | Clear solution | homogeneous < 2 h |

Organic Solvent Mixtures in Reconstitution

No single organic solvent was identified that in combination with WFI resulted in complete dissolution of DP-6P. Therefore, combinations of propylene glycol and other solvents were screened as organic fraction in the reconstitution composition. Physical stability was assessed by visual inspection. Chemical stability was assessed using UPLC/MS.

Figure 1A:
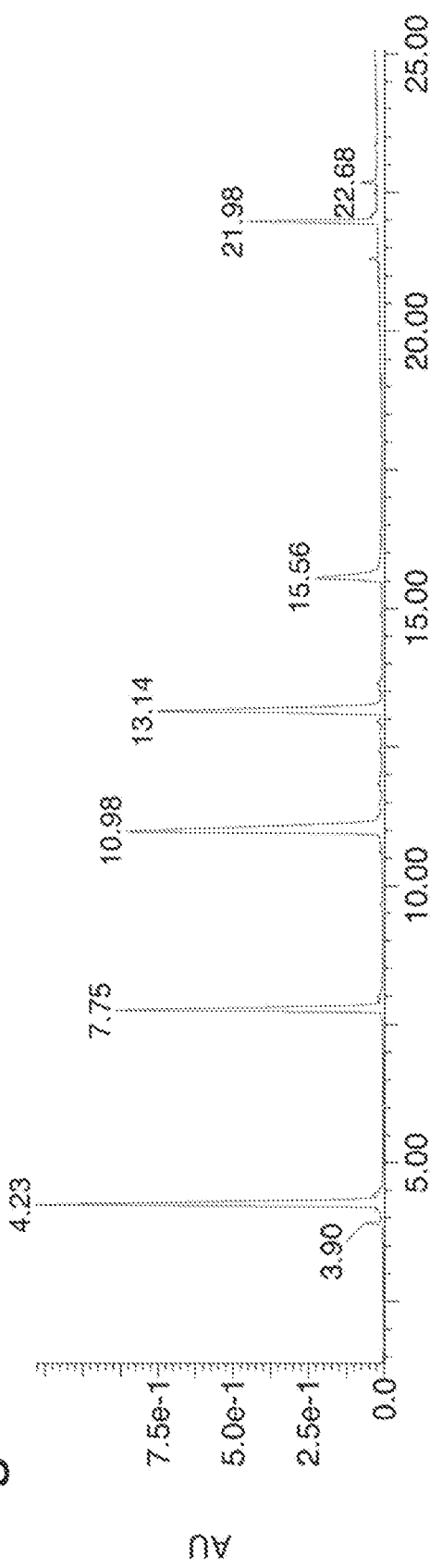
Figure 1B:
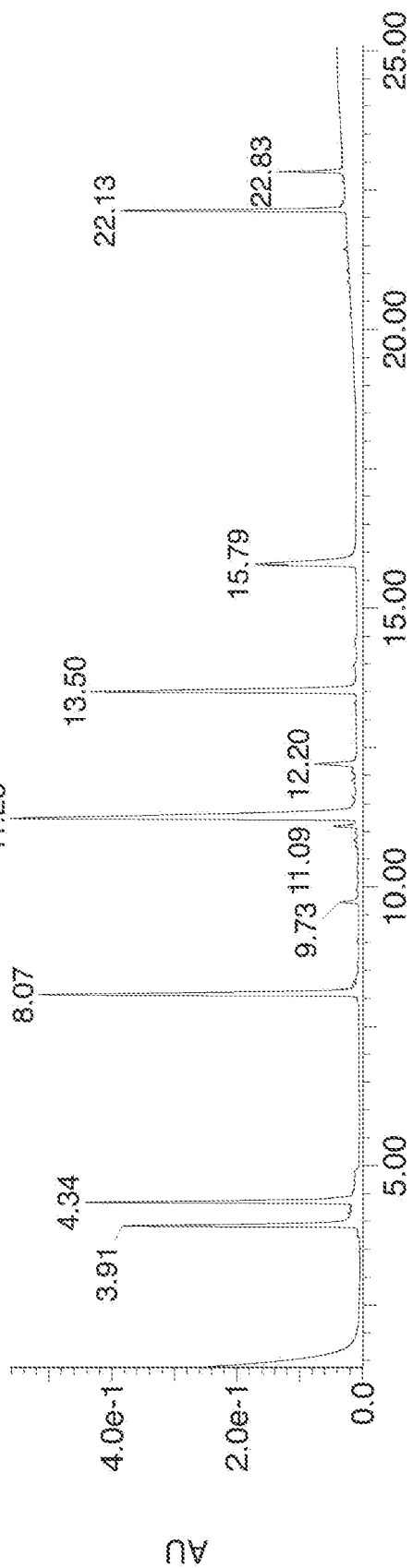

Although still no complete dissolution of DP-6P was observed, the most optional solvent combination identified for dissolution of DP-6P was a mixture of ethanol, propylene glycol and Cremophor EL as emulsifier with WFI (FIG. 1).

Figure 2B:
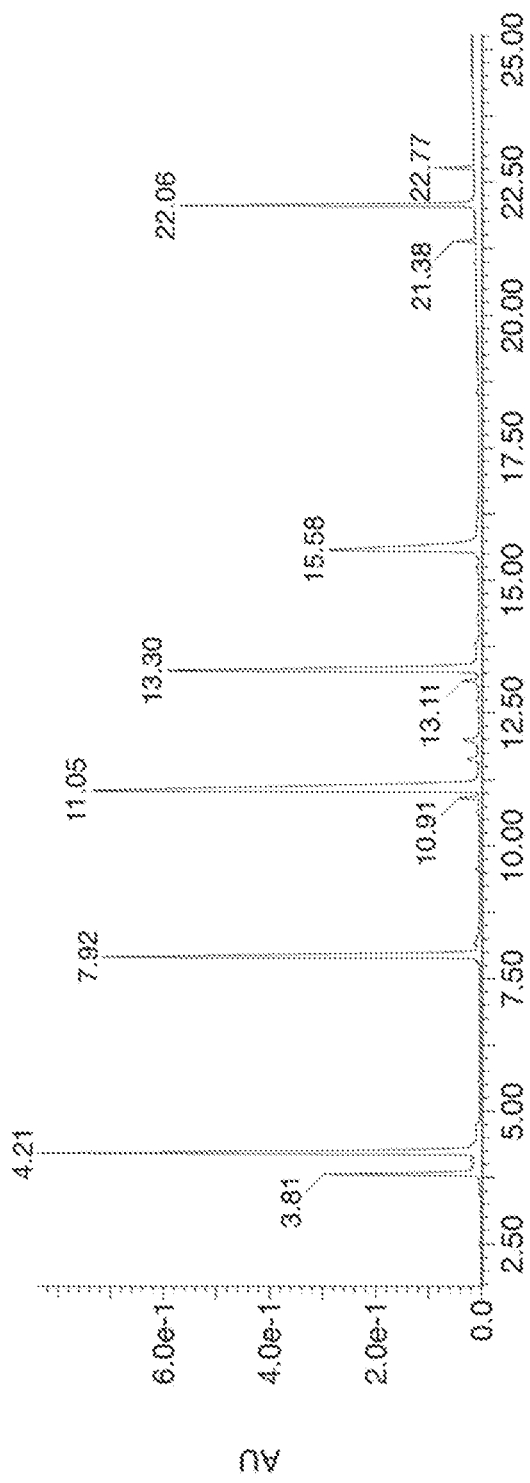
Figure 2C:
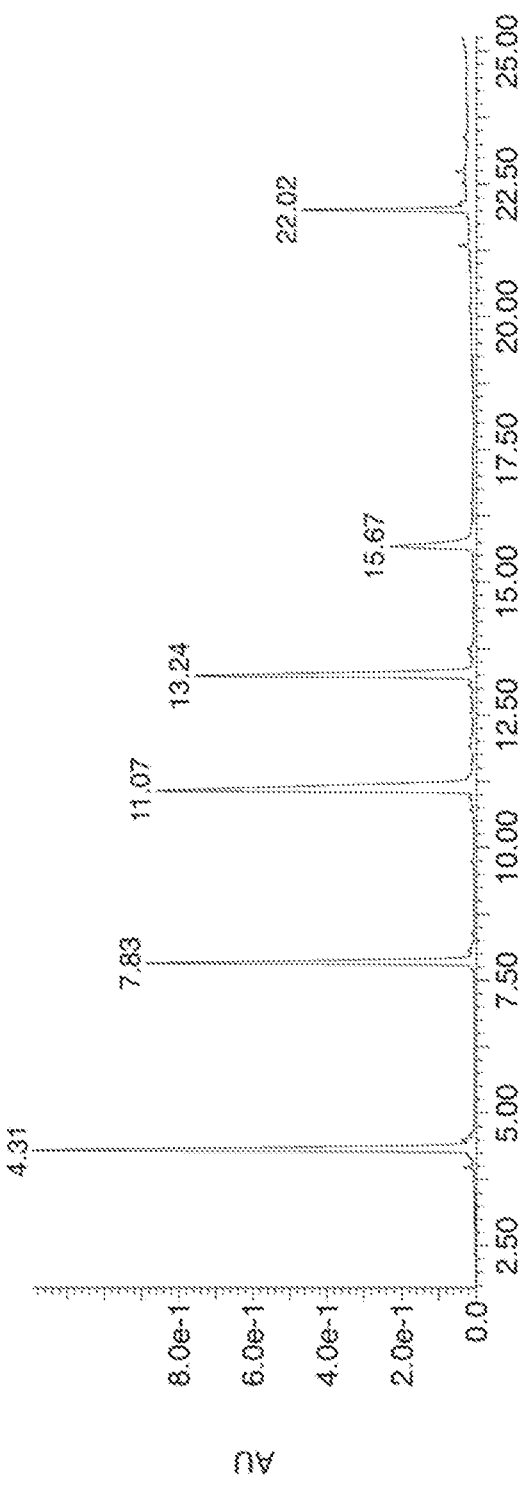
Figure 2D:
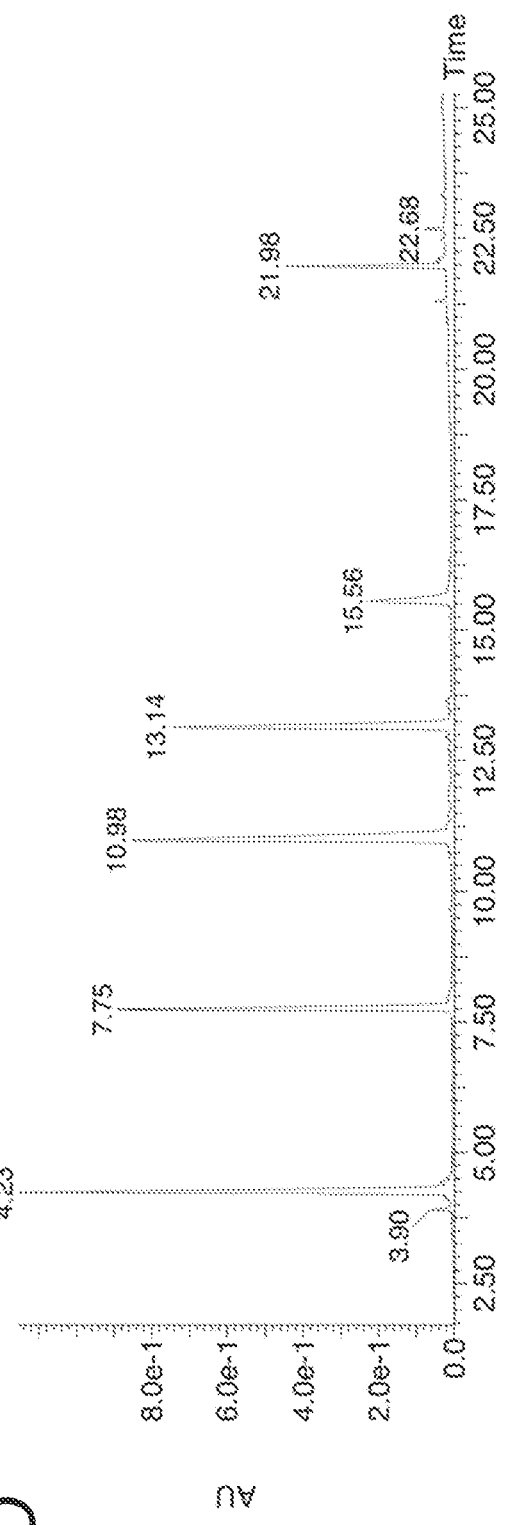
Figure 3A:
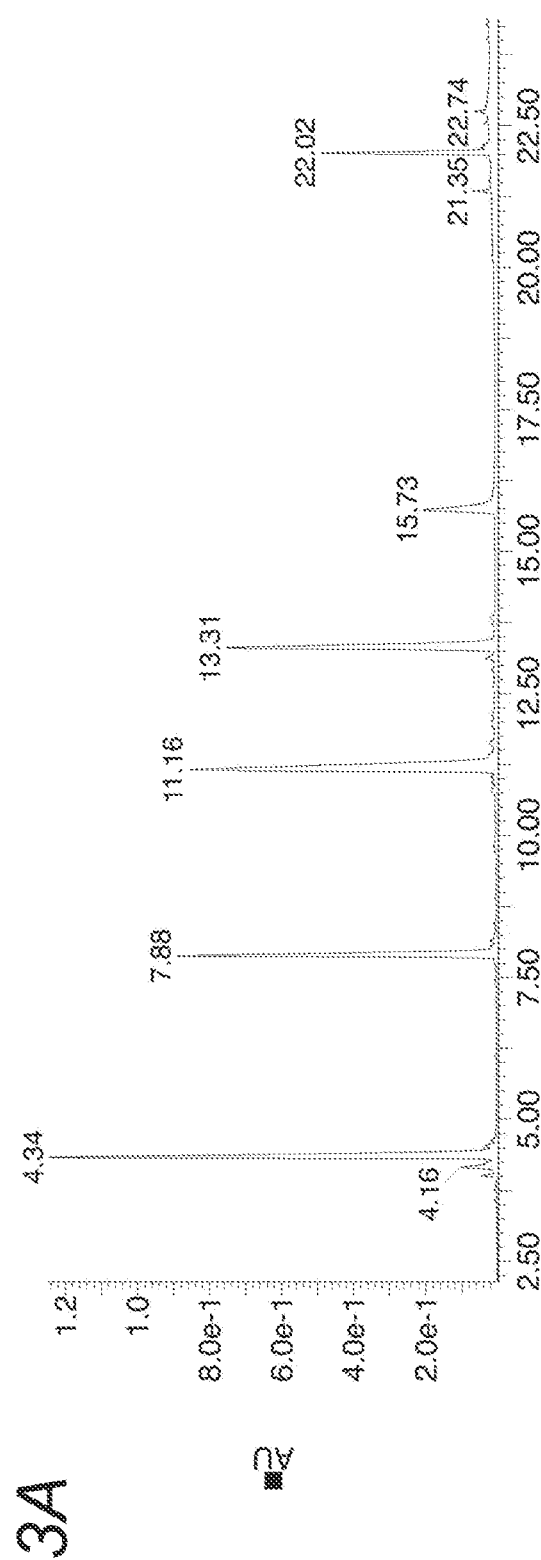
FIGS. 3A-3D show UPLC chromatograms of DP-6P (comprising SLPs represented by SEQ ID NOs: 1-6) in two different solvent mixtures. All solvent mixtures contain per mL 750 µL 0.1M Citric acid in water, 62.5 µL Propylene Glycol, 125 µL Ethanol and either Tween20 or Cremophor EL (62.5 µL).
Figure 3B:
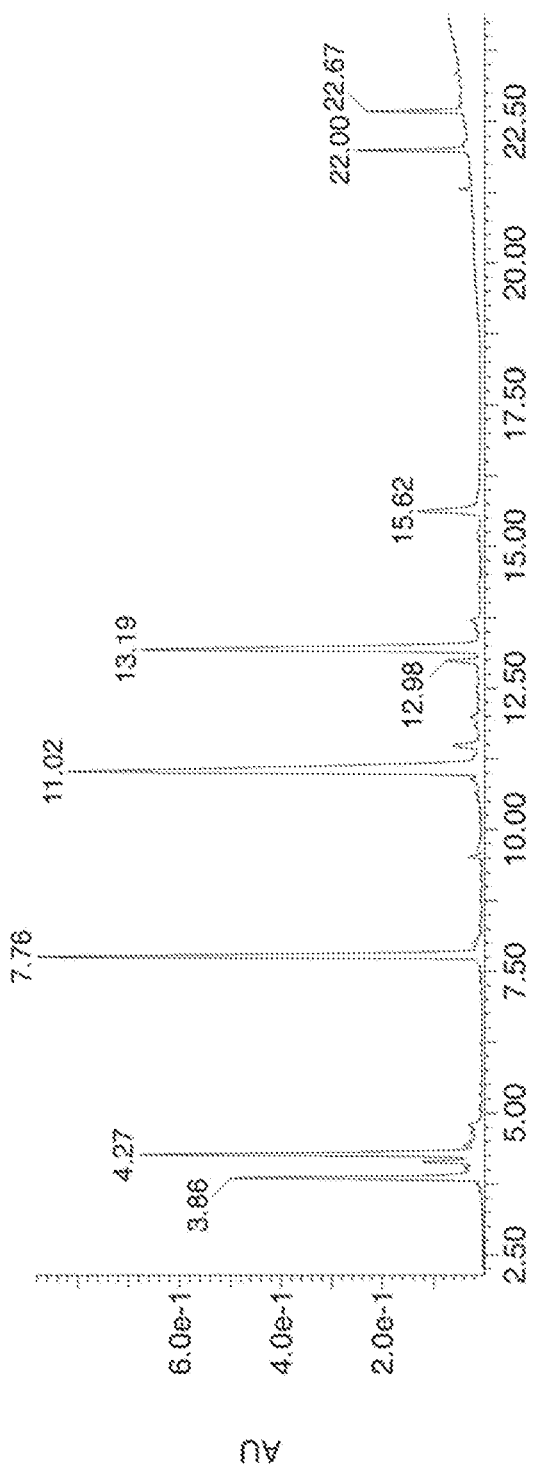
Figure 3C:
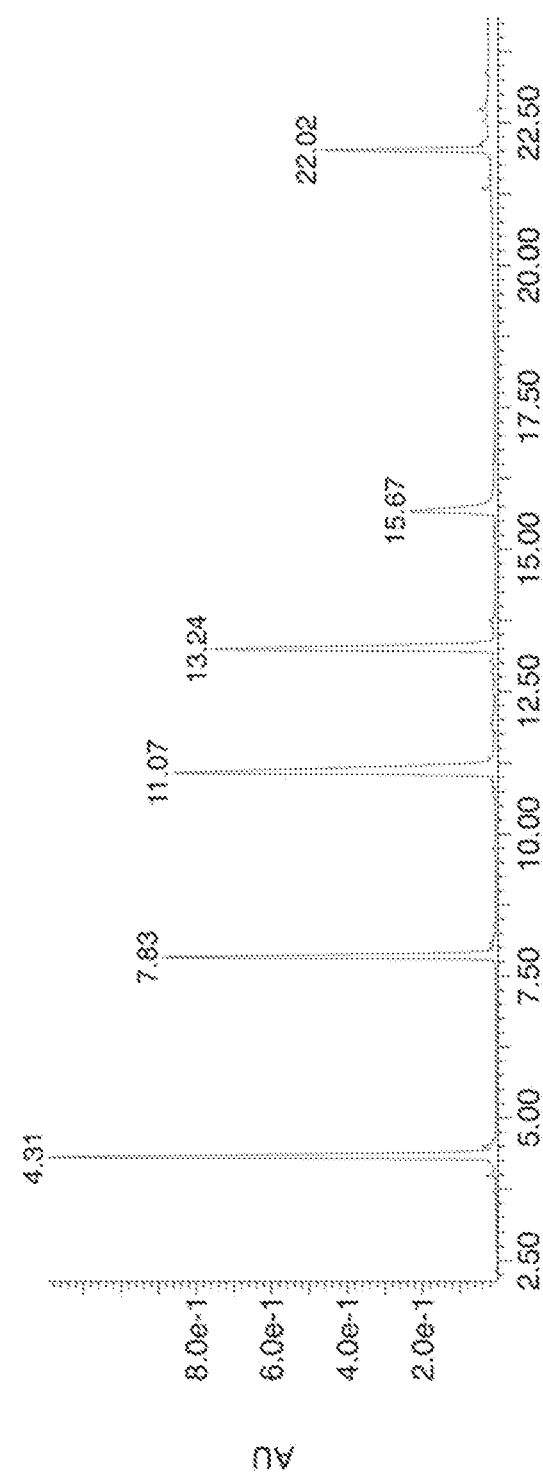
Figure 3D:
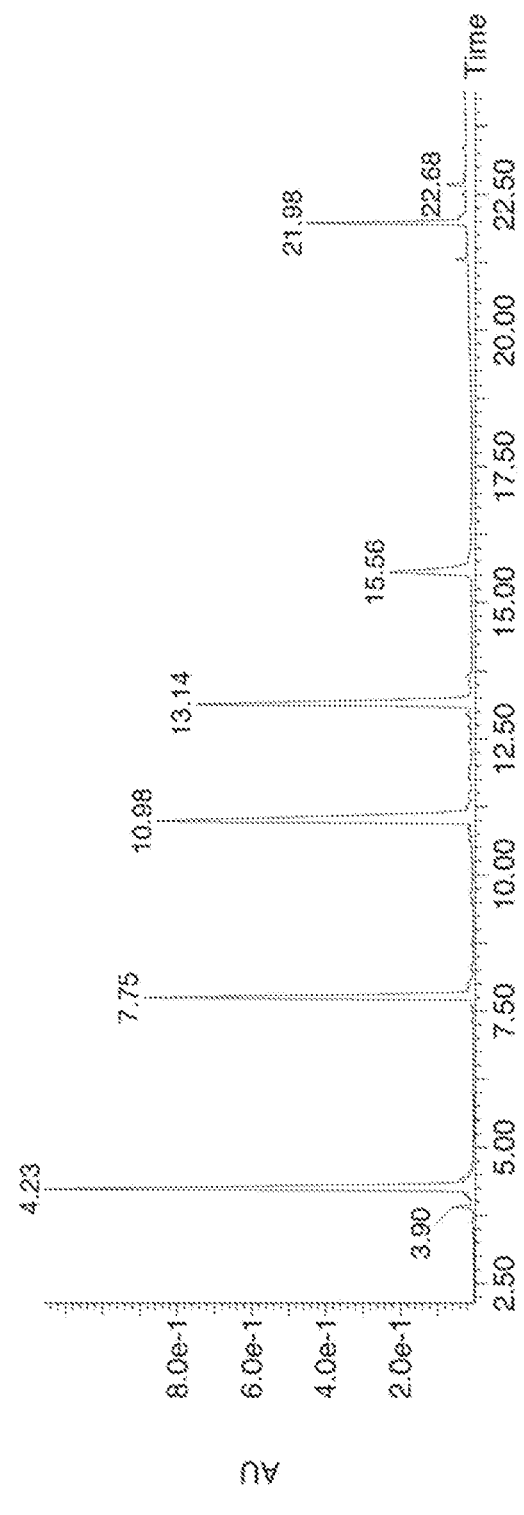

To further improve the dissolution process while limiting disulfide formation, the effect of adding several antioxidants and reducing agents to the solvent mixture (mixture of ethanol, propylene glycol, Cremophor EL and WFI) and the peptide solution was assessed. Chemical stability was analyzed with UPLC/MS to monitor the extent of disulfide formation. Addition of DTT (35 molar equivalents compared to peptide) or ascorbic acid (0.1-1% solution in WFI) did not result in a reduction of disulfide formation, whereas the addition of a 0.05-0.1 M aqueous citric acid solution to the solvent mixture resulted in both improved dissolution of DP-6P and limited disulfide formation of area % values of ≤1% per disulfide two hours after dissolution of the Drug Product. Citrate buffer at pH3 and a concentration of 0.05-0.1 M could not be used for emulsification because of poor peptide dissolution (data not shown). FIG. 2 presents chemical stability in time (t=0 and t=2 h) of DP reconstituted in a mixture of 1 mg/mL ascorbic acid in water, propylene glycol and ethanol versus a mixture of 0.1M citric acid in water, propylene glycol, ethanol, and Cremophor EL.

Testing Reconstitution Compositions after Reconstitution and after Subsequent Emulsification Cremophor EL as emulsifier is less preferred in vaccine formulations because of reported side effects at higher dosages. However, the dissolving and emulsifying properties of Tween 80, cyclodextrins, and Triton X as alternatives for Cremophor EL, were inadequate (data not shown). Upon visual inspection, promising results were obtained with a combination of propylene glycol, ethanol, citric acid in WFI and 2% Tween20. The results of emulsification experiments as summarized in Table 4 show that emulsions comprising propylene glycol and ethanol in combination with either Cremophor EL or Tween 20 result in most stable emulsions. However, it appeared that the chemical stability in solution of both DP-6P and DP-7P was significantly worse in the presence of Tween20 instead of Cremophor EL, i.e. with area % values of over 5% per disulfide two hours after dissolution of the Drug Product (see FIG. 3 for UPLC chromatograms of DP-6P; results for DP-5P and DP-7P were highly similar (data not shown).

Taken together, from the data presented in Table 4 and FIG. 3 it can be concluded that Cremophor EL is preferred as an emulsifier for DP-6P emulsions with Montanide, based on both physical and chemical stability of the product.

Figure 4C:
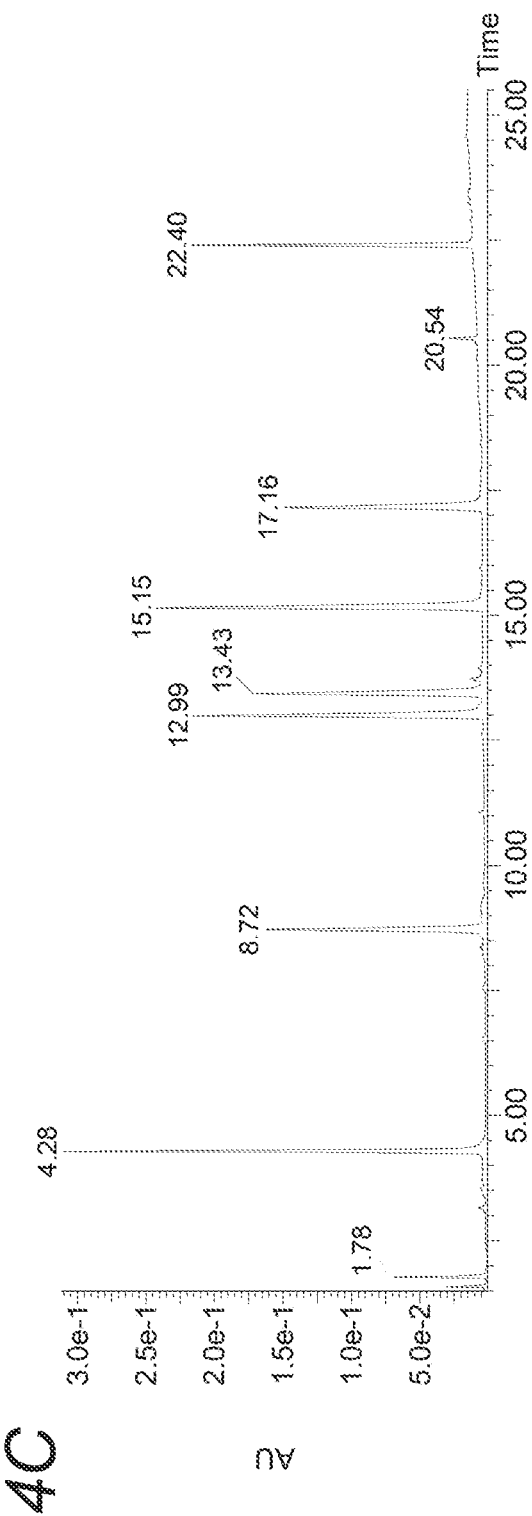
Figure 4D:
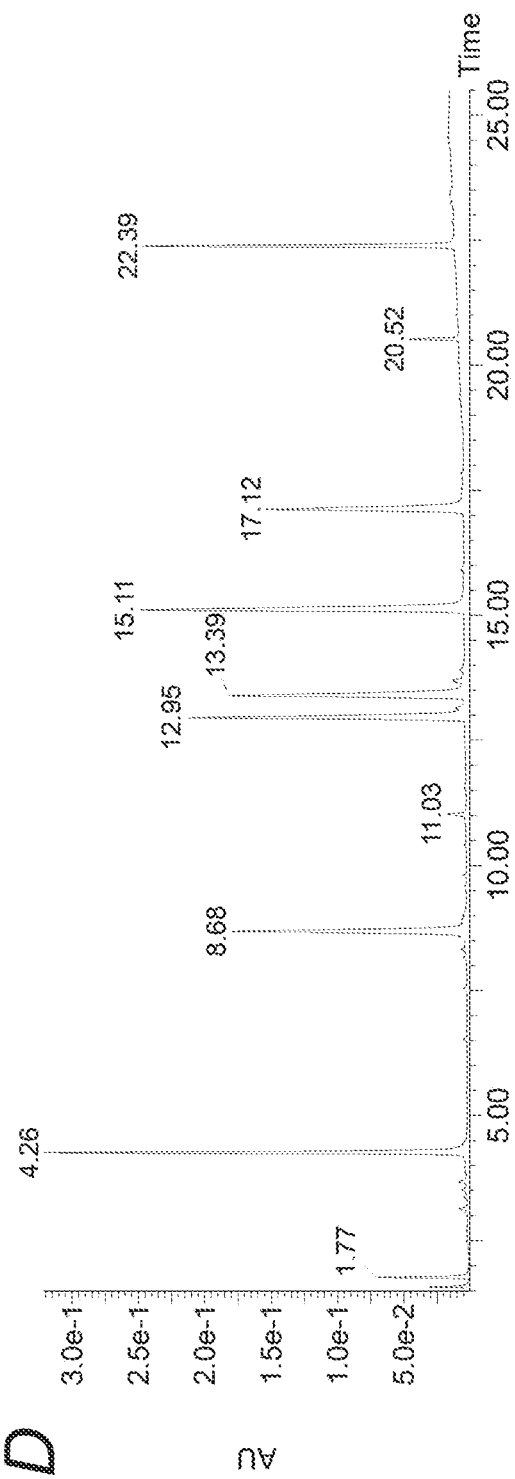

To demonstrate that the results obtained for chemical stability of Drug Product in solution can be translated to the in-use chemical stability of the Drug Product in the vaccine emulsion, the in-use stability of DP-6P and DP-7P vaccine emulsions was studied and results are presented in FIGS. 4 A, B, C and D. These results confirm that, after the emulsification step, the chemical stability of the Drug Products in the vaccine preparations is retained.

TABLE 4

Solvent screening with premixed organic and aqueous solvents (1 mL).

| Citric acid solution | Organic 1 | Organic 2 | Organic 3 | Peptides solubility | Physical emulsion stability |
|---|---|---|---|---|---|
| 0.1M, 800 µL | PG (3) | EtOH (2) | Cremophor EL (1) | + | − |
| 0.1M, 800 µL | PG (1) | 0 | Cremophor EL (1) | − | − |
| 0.1M, 800 µL | PG (2) | EtOH (1) | Cremophor EL (1) | + | − |
| 0.1M, 800 µL | PG (3) | EtOH (3) | Cremophor EL (2) | − | NA |
| 0.1M, 800 µL | PG (1) | EtOH (1) | Cremophor EL (2) | + | − |
| 0.1M, 775 µL | PG (2) | EtOH (1) | Cremophor EL (1) | −+ | − |
| 0.1M, 750 µL | PG (3) | EtOH (2) | Cremophor EL (1) | −+ | − |
| 0.1M, 750 µL | PG (1) | EtOH (2) | Cremophor EL (1) | −+ | + |
| 0.1M, 750 µL | 0 | EtOH (4) | Cremophor EL (1) | −+ | − |
| 0.1M, 700 µL | PG (3) | EtOH (2) | Cremophor EL (1) | − | − |
| 0.1M, 800 µL | PG (1) | EtOH (2) | Tween 20 (1) | −+ | + |
| 0.1M, 750 µL | PG (1) | EtOH (2) | Tween 20 (1) | −+ | NA |
| 0.1M, 600 µL | PG (1) | EtOH (2) | Tween 20 (1) | − | NA |
| 0.1M, 800 µL | PG (1) | EtOH (2) | Tween 20, 50% aq (1) | −+ | + |
| 0.1M, 800 µL | PG (1) | EtOH (2) | Tween 20, 25% aq (1) | −+ | + |
| 0.1M, 750 µL | PG (1) | EtOH (2) | Triton X (1) | − | NA |

TABLE 4-continued

Solvent screening with premixed organic and aqueous solvents (1 mL).

| Citric acid solution | Organic 1 | Organic 2 | Organic 3 | Peptides solubility | Physical emulsion stability |
|---|---|---|---|---|---|
| 0.1M, 600 μL | PG (1) | EtOH (2) | Triton X (1) | − | NA |
| 0.05M, 800 μL | PG (1) | EtOH (1) | Cremophor EL (2) | + | − |
| 0.05M, 775 μL | PG (2) | EtOH (1) | Cremophor EL (1) | −+ | − |
| 0.05M, 750 μL | PG (2) | EtOH (1) | Cremophor EL (1) | −+ | + |
| 0.05M, 700 μL | PG (2) | EtOH (1) | Cremophor EL (1) | − | ++ |

Fine-Tuning for Robustness in Emulsification
Peptide Solubility and Emulsion Stability A subsequent series of experiments was performed in which the ratio of PG/EtOH/Cremophor EL was varied, two different concentrations of citric acid solution were tested, different emulsification methods were applied and the ratio of organic vs. aqueous components of the mixture was varied. In general, 1 mL reconstitution composition was prepared by mixing the organic and aqueous solvents before adding them to the lyophilized Drug Product. Subsequently, an emulsion was prepared by adding 1 mL Montanide to the 1 mL of aqueous peptide solution using different mixing steps and/or connectors as indicated in Table 5 and 6.

TABLE 5

Variation in emulsification method using different reconstitution compositions:

| Emulsification method | Buffer composition | Peptides solubility | Emulsion stability |
|---|---|---|---|
| 20 slow* cycles and 80 fast* cycles | A | + | − |
| 40 cycles in 40 sec | A | + | − |
| 20 slow cycles and 80 fast cycles | B | + | − |
| 10 slow cycles and 40 fast cycles | B | + | − |
| 20 slow cycles and 80 fast cycles | C | +− | + |
| 10 slow cycles and 40 fast cycles | C | +− | +− |
| 20 slow cycles and 40 fast cycles | C | +− | + |
| 40 fast cycles | C | +− | + |
| 40 fast cycles | D | +− | + |
| 20 slow cycles and 40 fast cycles | E | − | ++ |
| 40 fast cycles | E | − | ++ |

*Slow cycles: 2 seconds per cycle. Fast cycles: 1 second per cycle.
A = 800 μL 0.05M citric acid and 200 μL PG/EtOH/Cremophor EL (1:1:2);
B = 800 μL 0.05M citric acid and 200 μL PG/EtOH/Cremophor EL (2:1:1);
C = 750 μL 0.1M citric acid and 250 μL PG/EtOH/Cremophor EL (2:1:1);
D = 750 μL 0.1M citric acid and 250 μL PG/EtOH/Cremophor EL (1:2:1); and,
E = 700 μL 0.1M citric acid and 300 μL PG/EtOH Cremophor EL (2:1:1).

Peptide Emulsion Stability in More Detail: PSD Analysis by Laser Diffraction

For five different reconstitution compositions, the effect of different emulsification methods on particle size was analysed with laser diffraction, using a Malvern Mastersizer 2000. For all samples, 1 mL reconstitution composition was prepared by mixing the organic and aqueous solvents before adding them to the lyophilized Drug Product. Subsequently, an emulsion was prepared by adding 1 mL Montanide to the 1 mL of aqueous peptide solution. Mixing of the organic and aqueous phases was performed in three different ways:
  Using the T-connector process and performing mixing cycles as indicated in Table 6;
  Using an I-connector and performing mixing cycles as indicated in Table 6; or,
  Adding 1 mL Montanide to the vial containing the peptide solution in reconstitution composition, and vortexing the mixture during 30 seconds.

A summary of the results is presented in Table 6. Approximate values for D(0.5) are given (volume based distribution).

TABLE 6

Emulsification of peptide formulations characteristics and average D(0.5) values using different reconstitution compositions:

| Reconstitutio composition | Emulsification process | Solubility | D(0.5) | Stability |
|---|---|---|---|---|
| A | T-connector, 20 slow and 80 fast cycles | − | 3 μm | ≥3 h |
| A | Vortex 30 seconds | − | 11 μm | 3 h |
| B | T-connector, 20 slow and 80 fast cycles | +− | 5-7 μm* | ≥3 h |
| B | T-connector, 40 fast cycles | +− | 9 μm | ≥3 h |
| B | I-connector, 10 slow and 40 fast cycles | +− | 11 μm | ≥2 h |
| C | T-connector, 40 fast cycles | +− | 4 μm | ≥2 h |
| D | T-connector, 40 fast cycles | +− | 11 μm | 1 h |
| E | T-connector, 20 slow and 80 fast cycles | + | 11 μm | 1 h |
| E | I-connector, 20 slow and 80 fast cycles | + | 12 μm | 1 h |

*Variation in PSD was observed for analysis diluted in WFI or diluted in 0.01M citric acid solution
A = 600 μL 0.1M citric acid and 400 μL PG/EtOH/Cremophor EL (5:4:2);
B = 750 μL 0.1M citric acid and 250 μL PG/EtOH/Cremophor EL (2:1:1);
C = 750 μL 0.1M citric acid and 250 μL PG/EtOH/Cremophor EL (1:2:1);
D = 775 μL 0.1M citric acid and 225 μL PG/EtOH/Cremophor EL (2:1:1); and,
E = 800 μL 0.1M citric acid and 200 μL PG/EtOH/Cremophor EL (2:1:1).

Both from Table 5 and Table 6, it appears that no difference in emulsion stability was observed between the different mixing methods and/or different types of connectors used. However, vortexing the mixture instead of using a connector resulted in emulsions with a much larger particle size, which is less favorable for stability. In general emulsions with a smaller particle size are more stable.

Further, emulsion stability was improved by increasing the percentage of the organic fraction (mixture) in the total volume of reconstitution composition. However, the highest volumes of organic content tested here (300-400 μL) resulted in decreased solubility of the Drug Product. Therefore, the optimum of organic content was between 200 and 300 μL per mL (about 250 μL) reconstitution composition. In addition, variation in the concentration of the citric acid (0.05 or 0.1M) solution did not seem to affect the emulsion stability, while slightly better dissolution of DP-6P was obtained when a 0.1 M citric acid solution was used.

Particle Size Analysis Using Micro Flow Imaging

To study the effect of citric acid concentration on emulsion stability and particle size of the emulsion in more detail, additional particle size analysis experiments were compared using the solvent that resulted in the smallest particle size after emulsification with 1 mL Montanide, i.e. a reconstitution composition with an organic- to aqueous-phase ratio of 1:3, wherein the organic phase contains PG, EtOH and Cremophor EL in a ratio of PG to EtOH to Cremophor EL of 1:2:1 (Table 6). Direct comparison experiments were performed, wherein the molar amount of citric acid in the aqueous phase was varied (0.05 and 0.1M citric acid, i.e. an end concentration of citric acid in reconstitution composition of 0.038 and 0.075M citric acid, respectively). DP-6P was dissolved in 1 mL of such reconstitution composition, followed by emulsification with 1 mL Montanide using a T-connector process and performing 50 fast mixing cycles. In these experiments, both dissolution of the Drug Product and particle size and emulsion stability were analyzed. As a read-out, Micro Flow Imaging (MFI) was performed using an MFI 5200 in order to visualize the particles with a camera so that irregularities can be studied visually. The PSD-comparison of 0.05 and 0.1M citric acid of citric acid reconstitution composition is shown in FIG. 5.

Figure 5:
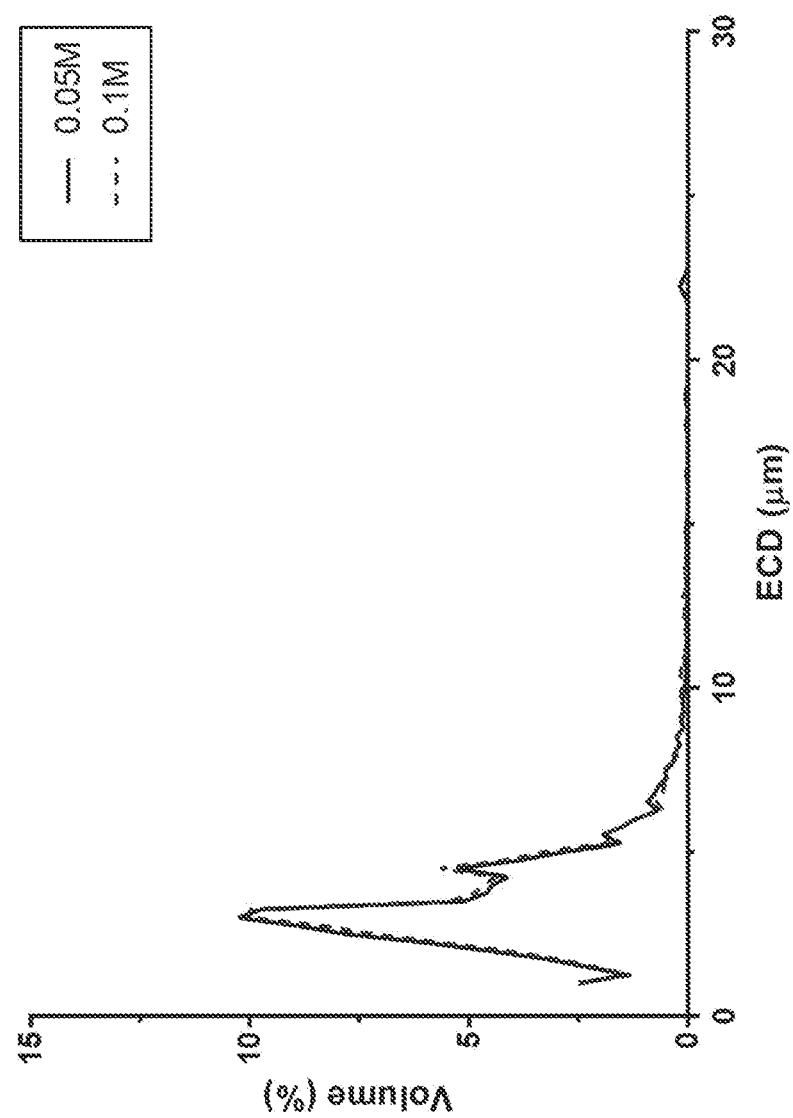
FIG. 5 shows particle size distribution comparison (overlay) between DP-6P emulsions using two different citric acid concentrations. DP-6P (2.40 mg total peptide) dissolved in a mixture of 750 µL 0.05M or 0.1M Citric acid in water, 62.5 µL Propylene Glycol, 125 µL Ethanol and 62.5 µL Cremophor EL, and subsequently emulsified with 1 mL Montanide ISA51 VG.
Figure 6A:
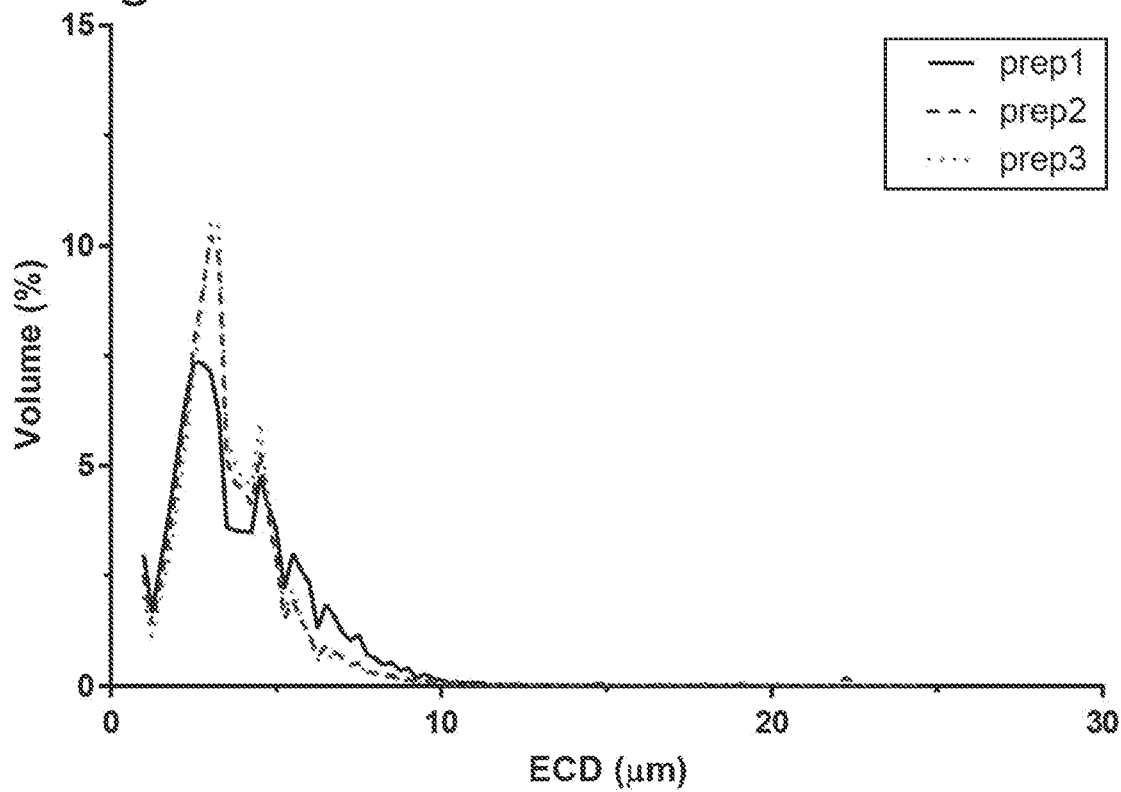
FIGS. 6A-6B show particle size distribution comparison (overlay) between DP-6P emulsions (comprising SLPs represented by SEQ ID NOs: 1-6). DP-6P (2.40 mg total peptide) was dissolved in a mixture of 750 µL 0.1M Citric acid in water, 62.5 µL Propylene Glycol, 125 µL Ethanol and 62.5 µL Cremophor EL and subsequently emulsified with 1 mL Montanide ISA51 VG.
Figure 6B:
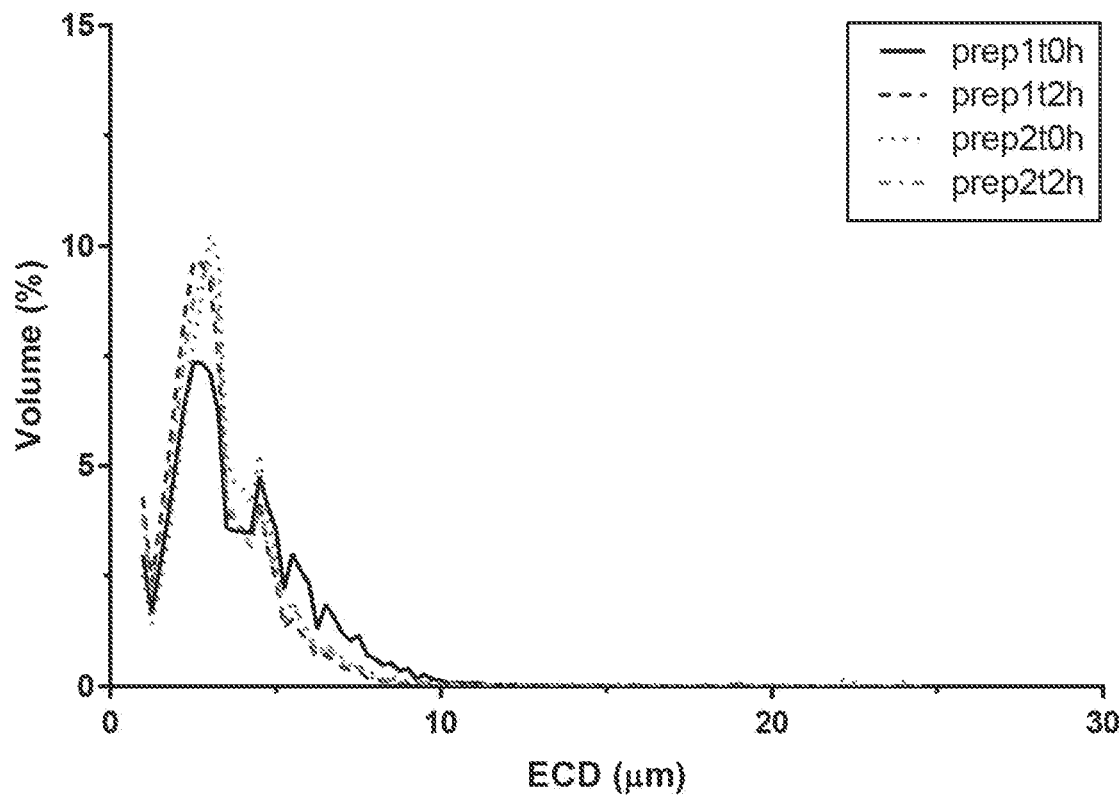

As can be seen in FIG. 5, the concentration of citric acid solution does not influence the PSD of the emulsion. However, dissolution of the Drug Product was slightly better when 0.1M citric acid was used. FIG. 6 presents MFI results of three independent preparations of a DP-6P emulsion (FIG. 6, panel A) or two independent preparations analyzed at two different time points after preparation (FIG. 6, panel B), wherein the Drug Product has been reconstituted using the same solvent combination (750 μL 0.05M citric acid+ 250 μL PG/EtOH/Cremophor EL 1:2:1). Very robust PSD results were obtained. In addition, the emulsions were all stable for at least 2 hours.

Application of Preferred Reconstitution Solvent and Emulsification Method on DP-6P and DP-7P Since 750 μL citric acid solution+250 μL PG/EtOH/ Cremophor EL 1:2:1 was shown to give robust PSD results for DP-6P emulsions, and the use of 0.1M citric acid resulted in the best dissolution of the Drug Product, this solvent combination was tested extensively for the preparation of DP-6P and DP-7P emulsions.

DP-6P and DP-7P emulsions were prepared according to the instructions in Table 1. Briefly, 1 mL of reconstitution composition (750 μL 0.1M citric acid+250 μL PG/EtOH/ Cremophor EL 1:2:1) was added to the lyophilized Drug Product, the resulting solution was mixed with 1 mL Montanide using a T-connector and applying 50 fast mixing cycles. PSD values for MFI analyses are given in ECD (equivalent circle diameter) and a number-based distribution is given. It should be noted that MFI and laser diffraction are complementary techniques. Therefore, a direct comparison of average particle size values obtained by laser diffraction and by MFI cannot be performed.

TABLE 7

DP-6P Particle size D (0.5) values in μm.

|  | T = 0 | T = 1 | T = 2 | T = 3 |
|---|---|---|---|---|
| Prep 1 | 1.77 | 1.71 | 1.70 | 1.71 |
| Prep 2 | 1.73 | 1.62 | 1.69 | 1.69 |
| Prep 3 | 1.61 | 1.73 | 1.75 | 1.69 |
| Average | 1.70 | 1.69 | 1.71 | 1.70 |

TABLE 8

DP-7P Particle size D (0.5) values in μm.

|  | T = 0 | T = 1 | T = 2 | T = 3 |
|---|---|---|---|---|
| Prep 1 | 1.64 | 1.59 | 1.56 | 1.59 |
| Prep 2 | 1.59 | 1.61 | 1.61 | 1.57 |
| Prep 3 | 1.65 | 1.66 | 1.63 | 1.55 |
| Average | 1.63 | 1.62 | 1.60 | 1.57 |

Table 7 and 8 show that by using a reconstitution composition comprising 750 μL 0.1M citric acid+250 μL PG/EtOH/Cremophor EL 1:2:1 (i.e. 750 μL 0.1M Citric acid in water, 62.5 μL Propylene Glycol, 125 μL Ethanol and 62.5 μL Cremophor EL), for both DP-6P and DP-7P emulsions can be prepared that are stable for at least 3 hours.

Example 2

Introduction

Therapeutic efficacy of SLP vaccination in combination with CpG1826 has previously been demonstrated in mice carrying established TC-1 tumors, which express the oncogenic E6 and E7 proteins of HPV16 (Zwaveling et al., *J. Immunol.* (2002) 169:350-358). To assess whether SLPs retain functionality in the most optimal formulation identified in Example 1 (750 μL 0.1M citric acid+250 μL PG/EtOH/Cremophor EL 1:2:1), we therapeutically vaccinated mice carrying a TC-1 tumor with an SLP harboring the D&-restricted CTL epitope RAHYNIVTF (represented herein by SEQ ID NO: 67), reconstituted either in DMSO/ WFI or the novel reconstitution composition. All vaccines were subsequently emulsified in Montanide. Tumor outgrowth was monitored for 75 days. At the peak of the vaccine-induced T cell response, the percentage and phenotype of RAHYNIVTF-specific $CD8^+$ T cells was determined in the blood. SLP reconstituted in DMSO/WFI and the novel reconstitution composition showed a similar potency in inducing TC-1 tumor regression. Mice vaccinated with the SLP reconstituted in the novel solution showed a higher percentage of RAHYNIVTF-specific $CD8^+$ T cells in the blood.

Materials

TABLE 9

Materials applied during TC-1 tumor experiment.

| Material | Origin/supplier |
|---|---|
| C57BL/6 female mice, 6-8 weeks old | Harlan Laboratories |
| Montanide ISA VG51 | Seppic; batch 2384535/ U40740; exp 13 Feb. 2017 |
| CpG ODN1826 (5 mg/ml) | Invivogen; cat no tlrl-1826 |
| DMSO | Mylan; lot nr 140706; exp June 2017 |
| WFI | Fresenius Kabi; W005 4B03; exp 6 Mar. 2018 |
| KLRG1-PeCy7 | eBioscience; cat nr 25-5893-82 |
| CD62L-Alexa780 | eBioscience; cat nr 47-0621-82 |
| CD44-Pacific Blue | BioLegend; cat nr 103020 |
| CD127-Biotin | eBioscience; cat nr 13-1271-85 |
| CD8a-Alexa700 | eBioscience; cat nr 56-0081-82 |
| CD3-V500 | BD; cat nr 560771 |
| Streptavidin- | ThermoFischer; cat nr |

TABLE 9-continued

Materials applied during TC-1 tumor experiment.

| Material | Origin/supplier |
| --- | --- |
| Qdot605 | Q10101MP |
| 7-AAD viability staining | ThermoFisher, cat nr A1310; exp 22 Sep. 2016 |
| $D^b$-RAHYNIVTF tetramer | Production of LUMC |
| Trypsin | Gibco (Life Technologies) cat nr 25200-056 |
| Geneticin (G418) | Gibco (Life Technologies) cat nr 10131-027 |
| BSA | Roche Diagnostics; cat nr 10735078001 |
| Lysis buffer | LUMC Pharmacy |
| T-connector Discofix C | B Braun; 16494C |
| NORM-JECT Luer-lock 2 ml syringes | HSW; 4010-000V0 |
| NORM-JECT Luer-lock 1 ml syringes | HSW; 4010-200V0 |
| BD Microlance 3; 25G (0.5 × 16 mm) | BD; cat nr 300600 |
| Disposables | Various; LUMC |

Methods

Vaccine Preparation

The following groups of mice were included in the study:

Group 1: (n=5) 40% v/v DMSO/WFI emulsified 1:1 with Montanide ISA VG51.

Group 2: (n=5) Reconstitution composition (750 μL 0.1M Citric acid in water, 62.5 μL Propylene Glycol, 125 μL Ethanol and 62.5 μL Cremophor EL per mL) emulsified 1:1 with Montanide ISA VG51.

Group 3: (n=10) SLP GQAEPDRAHYNIVTFCCKCD-STLRLCVQSTHVDIR and 20 μg CpG ODN1826/mouse dissolved in 40% v/v DMSO/WFI, emulsified 1:1 with Montanide ISA VG51.

Group 4: (n=10) SLP GQAEPDRAHYNIVTFCCKCD-STLRLCVQSTHVDIR (SEQ ID NO: 6) and 20 μg CpG ODN1826/mouse dissolved in Reconstitution composition (750 μL 0.1M Citric acid in water, 62.5 μL Propylene Glycol, 125 μL Ethanol and 62.5 μL Cremophor EL per mL), emulsified 1:1 with Montanide ISA VG51.

For mice in Group 1, a solution was prepared by admixing and subsequently swirling 400 μL DMSO and 600 μL WFI. The solution was taken up in a 2 mL Luer-Lock syringe (Syringe A). In another 2 mL Luer-Lock syringe (Syringe B) 1 mL of Montanide ISA VG51 was taken up, after which both syringes were connected to a T-connector. An emulsion was generated by mixing the contents back and forth extensively. After mixing, the syringes were disconnected and a 25 G needle was placed on the syringe containing the emulsion. Per mouse, 100 μL was injected in the left flank subcutaneously.

The vaccine prepared for Group 2 was prepared in an identical manner, only differing by the use of reconstitution composition (750 μL 0.1M citric acid in water and 250 μL PG/EtOH/Cremophor EL 1:2:1, i.e. 0.075M citric acid, 6.25% v/v propylene glycol CAS no. 57-55-6, 12.5% v/v ethanol and 6.25% v/v polyoxyethyleneglyceroltririci-noleate 35 CAS no. 61791-12-6 in water) instead of DMSO and WFI. The vaccine for Group 3 was prepared by first dissolving the contents of a vial containing 1.5 mg SLP represented herein by SEQ ID NO: 6 (GQAE-PDRAHYNIVTFCCKCDSTLRLCVQSTHVDIR) in 400 μL DMSO. The SLP was produced via Fmoc solid phase peptide synthesis (*Fmoc Solid Phase Peptide Synthesis, A Practical Approach*, W. C. Chan, P. D. White Eds, Oxford Univ. Press 2000). Then, 520 μL WFI and 80 μL CpG ODN1826 (stock 5 mg/ml) were added to the peptide in DMSO. After taking up this solution in a 2 mL Luer-Lock syringe, the same vaccine preparation protocol was followed as for Group 1 by emulsifying with Montanide ISA VG51. The preparation of vaccine for Group 4 was identical to the protocol for Group 3, only differing in the first step in which the contents of a vial containing 1.5 mg SLP SEQ ID NO: 6 were dissolved in 920 μL Reconstitution composition and adding 80 μL CpG ODN1826 (stock 5 mg/ml).

Therapeutic Vaccination

Figure 7:
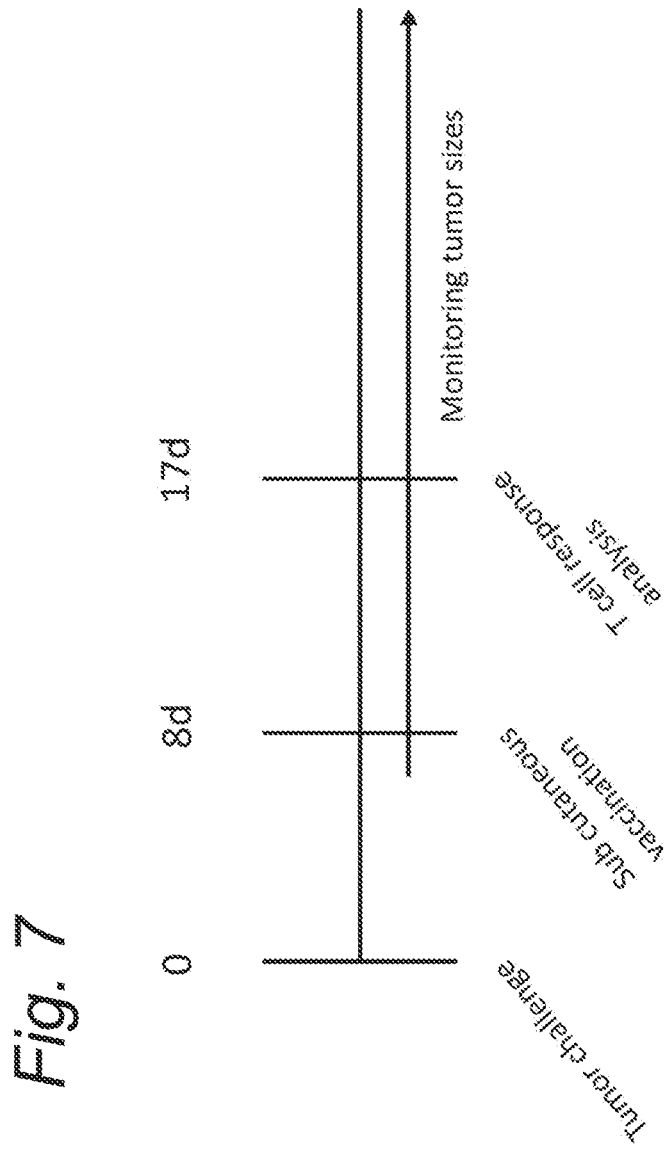
FIG. 7 shows a timeline for TC-1 tumor experiment.

TC-1 tumor cells, expressing the oncogenic E6 and E7 proteins of HPV16 were cultured in complete IMDM culture medium, supplemented with 400 μg/ml geneticin. On day 0, TC-1 cells were harvested using trypsin and washed 3 times with PBS/0.1% BSA. Directly after harvesting, 100,000 TC-1 cells were injected s.c. in the right flank of 40 female C57BL/6 mice. On day 8, all mice were s.c. vaccinated in the left flank as described in the section Vaccine preparation. The tumor size of all mice was monitored at least twice a week using a caliper up to 75 days after tumor challenge. The study was carried out as displayed in FIG. 7.

Measurement of Strength of T Cell Response in Blood

On day 9 after vaccination, blood was drawn from the tail vein of all mice. Blood samples were transferred to a 96-wells culture plate and centrifuged for 5 minutes at 1600 rpm. Erythrocytes were lysed by suspending blood cell pellets in Lysis buffer until orange coloration was observed. Subsequently, cells were washed in FACS buffer and stained with the fluorescent antibodies, the $D^b$-RAHYNIVTF-APC tetramer and 7-AAD mentioned in the Materials section above. After 30 minutes of incubation on ice, cells were washed and analyzed on a BD LSRII flow cytometer in the Leiden University Medical Center (Dept. of Rheumatology).

Results

Tumor Outgrowth Similar Between Vaccinated Groups

By monitoring the tumor size at least twice a week, a growth curve could be created for each individual mouse. In FIG. 8, the outgrowth of tumors is shown for the different groups. Tumor regression is observed in all mice vaccinated with SLP 6 and CpG1826. Tumors in the control groups receiving the vehicle only, either DMSO/WFI and Montanide or Reconstitution composition and Montanide, rapidly grow out. Besides natural variations, no clear differences are observed between both SLP-vaccinated groups. See FIG. 9A for a Kaplan-Meier survival plot, showing no differences between the vaccinated groups.

Vaccine-Induced Tetramer-Positive CD8+ T Cells

FIG. 9B shows the percentage of induced $D^b$-RAYNIVTF (tetramer) positive CD8+ T cells. Mice in group 4 (Rec. composition+SLP) show an enhanced tetramer-positive CD8+ T cell response, indicating that SLP and CpG formulated in Reconstitution composition is more effective than SLP and CpG formulated in an emulsion of DMSO/WFI and Montanide in the priming of specific murine CD8+ T cells. See Table 9 for the average percentages and standard deviations per group.

Significant differences were determined using an unpaired t-test, resulting in a p-value of p=0.022 between group 3 and 4.

Expression of KLRG1 and CD62L Indicate Favourable Antitumor Expression Profile after Vaccination with SLP 6

A study by Van Duikeren et al. (*J Immunol*, 2012; 189(7): 3397-403) aimed to identify parameters that correlated with the induction of an effective antitumor response. By identifying such biomarkers, different vaccine compositions can be tested in non-tumor bearing mice with prognostic value in tumor models. The authors found a correlation between the expression of KLRG1 and absence of CD62L expression on the one hand and effective antitumor immune responses on the other hand. We determined the percentages of KLRG1- and CD62L-expressing $D^b$-RAHYNIVTF$^+$ CD8$^+$ T cells in the blood of vaccinated mice on day 9 after vaccination using flow cytometry. No difference in percentage of RAHYNIVTF-specific KLRG1$^+$ CD62L$^-$ CD8$^+$ T cells is observed between groups 3 and 4. Not enough RAHYNIVTF-specific CD8+ T cells were detected to reliably study the expression of KLRG1 and CD62L in the groups of mice vaccinated with vehicle only (Group 1 and 2). See Table 10 for the average percentages and standard deviations per group.

TABLE 10

Average percentages and SD of tetramer$^+$ CD8$^+$ T cells, and averages and percentages of expression of CD62L and KLRG1 of tetramer$^+$ CD8$^+$ T cells in groups of mice vaccinated with SLP.

| | | % of TM+ CD8 T cells | | |
|---|---|---|---|---|
| Group | | % Tm+ of CD8 | % CD62L−KLRG1+ | % CD62L+KLRG1+ |
| 1 | Average | 0.1 | # | # |
| | SD | 0 | | |
| 2 | Average | 0.1 | # | # |
| | SD | 0.1 | | |
| 3 | Average | 1.4 | 51.9 | 4.0 |
| | SD | 1.0 | 14.9 | 3.2 |
| 4 | Average | 4.8* | 52.2 | 4.0 |
| | SD | 3.8 | 16.6 | 2.0 |

*indicates significant difference (p < 0.05) between groups 3 and 4 as determined by unpaired t-test.

Discussion

No differences were observed in overall tumor outgrowth between the groups of mice vaccinated with SLP 6 dissolved either in DMSO/WFI or Reconstitution composition. We did observe enhanced induction of specific CD8+ T cells in the mice vaccinated with the SLP dissolved in Reconstitution composition as compared to the group of mice vaccinated with the SLP dissolved in DMSO/WFI.

The adjuvanting properties of Montanide have been ascribed to the formation of an antigen depot and induction of local inflammation and cell death, which favors maturation of antigen-presenting cells. The enhanced induction of tetramer$^+$ CD8$^+$ T cells in the group of mice vaccinated with the SLP dissolved in Reconstitution composition suggests that the combination of this solution with Montanide constitutes an emulsion with beneficial antigen release properties or local stimulation of antigen-presenting cells. The favourable profile of KLRG1 expression and absence of CD62L was similar between both groups of mice vaccination with the SLP. The data demonstrate that SLPs reconstituted in the reconstitution composition of the invention maintain their immunogenic capacity as compared to the originally used reconstitution composition (DMSO/WFI).

Example 3

Material

The following lyophilized peptide composition was used:
P53 DP5P: comprising peptides represented herein by SEQ ID NO: 191, 193, 194, 201 and 203.

The following chemicals were used: Cremophor EL. (Sigma Aldrich. Kolliphor EL); Propylene Glycol (≥99.5%. Sigma Aldrich); Ethanol (Absolute. VWR Emprove® Ph Eur. BP.USP); Citric acid (≥99%. Sigma Aldrich); MilliQ water; Sterile Montanide ISA 51VG (SEPPIC.)

The following equipment was used: Syringe extrusion devices (Discofix-3 T-connector. B. Braun); DMSO-resistant syringes (2 mL NORM-JECT Luer Lock. Henke Sass Wolf); Waters UPLC/MS system EQP-004; Protein Simple MFI 5200

Methods

Preparation of the vaccine emulsion and a placebo emulsion was performed as described in Table 1.

Analysis of chemical stability was performed by UPLC-MS as described in Example 1, at the section describing methods for analysis of in-use chemical stability of HPV-DP-6P and HPV-DP-7P vaccine emulsions including extraction of the peptides from the vaccine emulsion.

Particle size analysis was performed by Micro Flow Imaging. Prior to analysis a dilution of the vaccine emulsion was prepared by adding 10 μL of emulsion to 10 mL Reconstitution Solution and mixing until homogeneous, followed by 1:500 dilution of this solution in Reconstitution Solution.

Analysis settings of MFI 5200:
Method: DS500.2
Sample volume: 1 mL
Purge volume: 0.20 mL
Analysis: 0.68 min or 1.000.000 particles
Consecutive runs: 1

Results are expressed in Equivalent Circle Diameter (ECD) and a number-based distribution is given. Particles ≥15 μm are filtered from the results since these are known to be artefacts rather than emulsion particles.

Results

Purity of Reconstituted Drug Product

Purity of the Drug Product at different time points was calculated as follows:

Purity (%)=100%−Sum of impurities≥0.05% area

An overview of the in-use purity of the P53-DP-5P vaccine product is given in Table 11.

TABLE 11

Overview of purity of reconstituted P53-DP-5P during storage at room temperature.

| | PRODUCT: P53-DP-5P IN-USE STORAGE TIME | | | |
|---|---|---|---|---|
| TEST | t = 0 h | t = 1 h | t = 2 h | t = 3 h |
| Purity [Area %] | 93.4 | 91.6 | 90.9 | 89.8 |
| Total related substances (≥0.05%) [Area %] | 6.6 | 8.4 | 9.1 | 10.2 |

As can be seen from in Table 11, purity of the Drug Products slowly decreases but is still ≥90.0% two hours after vaccine preparation. Example chromatograms of UPLC analysis of the vaccine at t=0 and t-=2 h are presented in FIG. 10.

Identification of main peaks and impurities with an area ≥1.0% area was performed using mass spectrometry. All related substances with an area ≥1.0% area are reported and identified by comparing the measure m/z values with molecular masses of the peptide sequences and their known and expected modifications. The resulting overview of related substances for an in-use storage of P53-DP-5P for up to 3 hours is given in Table 12.

TABLE 12

Overview and identification of related substances of reconstituted P53-DP-5P. In-use stability up to 3 h after reconstitution.

| | RETENTION TIME (min.) | IN-USE STORAGE TIME | | | | SEQ ID NO |
|---|---|---|---|---|---|---|
| | | t = 0 h | t = 1 h | t = 2 h | t = 3 h | |
| Peptides and related substances (≥0.05%) [Area %] | 4.97 | 13.00 | 12.02 | 11.87 | 11.63 | 194 |
| | 7.99 | 12.43 | 11.73 | 11.72 | 11.60 | 201 |
| | 9.57 | 23.90 | 22.38 | 22.31 | 22.19 | 193 |
| | 14.14 | 30.37 | 28.75 | 28.81 | 28.81 | 191 |
| | 16.82 | < | 1.05 | 1.54 | 1.87 | 203 intramolecular disulfide |
| | 19.46 | 13.73 | 16.73 | 16.21 | 15.56 | 203 |

Recovery of Drug Product from the Emulsion

The recovery of the five individual peptides present in P53-DP-5P from the emulsion was verified by comparison of emulsified and non-emulsified sample signals. An overview of the results is given in Table 13.

TABLE 13

Overview of recovery by comparison of emulsified and non-emulsified sample signals.

| | IN-USE STORAGE TIME | | | | SEQ ID NO |
|---|---|---|---|---|---|
| | t = 0 h | t = 1 h | t = 2 h | t = 3 h | |
| Recovery (RSD) Both values given as % | 97 (0.6) | 97 (0.8) | 96 (2.4) | 94 (2.3) | 194 |
| | 101 (2.0) | 103 (3.8) | 104 (5.1) | 102 (5.1) | 201 |
| | 98 (0.6) | 99 (1.1) | 99 (1.9) | 98 (1.3) | 193 |
| | 96 (0.3) | 98 (1.4) | 99 (1.7) | 98 (1.1) | 191 |
| | 70 (8.6) | 92 (3.4) | 90 (4.4) | 86 (4.8) | 203 |

Physical Stability

Physical stability was analysed by particle size analysis with MFI. Results are expressed in Equivalent Circle Diameter (ECD). Mean particle size values are given in Table 14, calculated from a number-based distribution.

TABLE 14

Mean particle size (ECD in µm) of P53 DP5P vaccine emulsions

| | T = 0 h | T = 1 h | T = 2 h | T = 3 h |
|---|---|---|---|---|
| Prep 1 | 1.91 | 1.95 | 1.93 | 2.01 |
| Prep 2 | 1.85 | 1.90 | 1.92 | 1.93 |
| Average | 1.88 | 1.93 | 1.93 | 1.97 |

Conclusion

Dissolution was successfully performed for a mixture containing 5 SLPs derived from the P53 antigen (P53 DP-5P).

Both chemical and physical in-use stability of the vaccine product was studied. Analysis of related substances and calculation of purity as summarized in Table 11 for P53 DP-5P shows that the purity of the Drug Product is ≥90.0% two hours after vaccine preparation. Only one related substance with a peak area % of ≥1% was observed. MS-identification showed that this peak is the intramolecular disulfide of the peptide set forth in SEQ ID NO: 203.

Physical stability of the P53 DP-5P vaccine product was studied by monitoring its particle size with MFI. The results of the particle size analysis are summarized in Table 14 and show that the particle size does not change up to three hours after vaccine preparation. In addition, all vaccine products were monitored by visual inspection during the stability study and no phase separation was observed at any time point.

Example 4

Material and Methods

The following lyophilized peptide composition was used: PRAME DP5P: comprising peptides represented herein by SEQ ID NO: 153, 155, 156, 160 and 166:

A set of five PRAME-derived peptides was selected based on UPLC retention times, variation in amino acid composition, and solubility in reconstitution solution as determined by visual inspection.

Other materials and methods used were the same as in Example 3.

Results

Purity of Reconstituted Drug Product

Purity of the Drug Product at different time points was calculated as follows:

Purity (%)=100%−Sum of impurities≥0.05% area

An overview of the in-use purity of the PRAME-DP-5P vaccine product is given in Table 15. It should be noted that the purity of lyophilized PRAME-DP-5P is already below 90%. Nevertheless, the very limited decrease in purity over time demonstrates good chemical stability of this reconstituted drug product.

TABLE 15

Overview of purity of reconstituted PRAME-DP-5P during storage at room temperature.

| | PRODUCT: PRAME-DP-5P IN-USE STORAGE TIME | | | |
|---|---|---|---|---|
| TEST | t = 0 h | t = 1 h | t = 2 h | t = 3 h |
| Purity [Area %] | 82.9 | 83.7 | 82.5 | 82.2 |
| Total related substances (≥0.05%) [Area %] | 17.1 | 16.3 | 17.5 | 17.8 |

The low purity decrease over time indicates high chemical stability. The impurities with an area ≥1.0% area in PRAME-DP-5P were already present in the mixture before reconstitution. Since no significant increase of these impurities was observed in this stability study, no identification of the impurities was performed. The resulting overview of related substances for an in-use storage of PRAME-DP-5P for up to 3 hours is given in Table 16.

TABLE 16

Overview and identification of related substances of reconstituted PRAME-DP-5P. In-use stability up to 3 h after reconstitution.

| | | IN-USE STORAGE TIME | | | | SEQ |
|---|---|---|---|---|---|---|
| | RETENTION TIME (min.) | t = 0 h | t = 1 h | t = 2 h | t = 3 h | ID NO |
| Related substances (≥0.05%) [Area %] | 10.68 | 23.35 | 22.85 | 22.65 | 22.62 | 155 |
| | 17.50 | 13.61 | 13.49 | 13.34 | 13.40 | 160 |
| | 18.91 | 13.49 | 14.15 | 13.81 | 13.59 | 166 |
| | 20.05 | 21.89 | 22.70 | 22.51 | 22.59 | 153 |
| | 21.15 | 10.56 | 10.52 | 10.17 | 9.98 | 156 |

Recovery of Drug Product from the Emulsion

The recovery of the five individual peptides present in PRAME-DP-5P from the emulsion was verified by comparison of emulsified and non-emulsified sample signals.

An overview of the results is given in Table 17.

TABLE 17

Overview of recovery by comparison of emulsified and non-emulsified sample signals.

| | IN-USE STORAGE TIME | | | | SEQ |
|---|---|---|---|---|---|
| | t = 1 h | t = 1 h | t = 2 h | t = 3 h | ID NO |
| Recovery (RSD) Both values given as % | 81 (9.8) | 87 (3.8) | 84 (2.1) | 81 (7.8) | 155 |
| | 81 (10.4) | 87 (3.7) | 84 (0.9) | 82 (8.2) | 160 |
| | 74 (10.8) | 84 (3.9) | 80 (1.0) | 77 (8.1) | 166 |
| | 76 (10.7) | 86 (3.3) | 83 (0.2) | 81 (8.6) | 153 |
| | 78 (10.5) | 84 (3.6) | 80 (1.0) | 76 (7.8) | 156 |

CONCLUSION

The purity of the PRAME DP-5P was not fully satisfactory (<90%), but the decrease in purity of the reconstituted vaccine product was very limited (purity T=0 82.9%, T=3 h 82.2%) confirming the benefits of the compositions described herein.

---

The invention claimed is:

1. A pharmaceutical comprising a vial comprising a mix of peptides consisting of:
   (i) 5 peptides consisting of the sequences set forth in SEQ ID NOs: 1-5; or
   (ii) 6 peptides consisting of the sequences set forth in SEQ ID NOs: 1-6; or
   (iii) 7 peptides consisting of the sequences set forth in SEQ ID NOs: 7-13.

2. The pharmaceutical according to claim 1, further comprising an additional vial comprising an adjuvant.

3. The pharmaceutical according to claim 2, wherein the adjuvant is an oil-based adjuvant, or wherein the adjuvant is selected from a mineral or non-mineral oil-based adjuvant.

4. The pharmaceutical according to claim 2, wherein the adjuvant is an immune-stimulating adjuvant.

5. The pharmaceutical according to claim 1, wherein the mix of peptides is lyophilized.

6. The pharmaceutical according to claim 1, wherein the mix of peptides consists of the 5 different peptides consisting of the sequences set forth in SEQ ID NOs: 1-5 or wherein the mix of peptides consists of the 7 different peptides consisting of the sequences set forth in SEQ ID NOs: 7-13.

7. The pharmaceutical according to claim 3, wherein the oil-based adjuvant is selected from bio-based oil adjuvants, adjuvants based on vegetable oil or fish oil, squalene-based adjuvant, MF59, Syntex Adjuvant Formulation, Freund's Complete Adjuvant, Freund's Incomplete Adjuvant, adjuvants based on peanut oil, Adjuvant 65, Lipovant, ASO4, Montanide adjuvants, adjuvants based on purified squalene and squalene emulsified with highly purified mannide mono-oleate, and a mixture of Drakeol VR and mannide monooleate.

8. The pharmaceutical according to claim 1, further comprising:(c) a vial comprising a composition for reconstituting dried peptides, wherein the composition comprises or consists of 60-80% v/v aqueous solution comprising an organic acid, 5-10% v/v propylene glycol, 10-20% v/v lower alcohol, and 5-10% v/v non-ionic hydrophilic surfactant.

9. The pharmaceutical according to claim 8, wherein the organic acid is citric acid.

10. The pharmaceutical according to claim 8, wherein the lower alcohol is ethanol.

11. The pharmaceutical according to claim 8, wherein the non-ionic hydrophilic surfactant is ethoxylated castor oil or:
   a. is a mono-, di or triglyceride, and/or
   b. has a hydrophilic-lipophilic balance (HLB) value between 9 and 14.

12. The pharmaceutical according to claim 8, wherein the composition for reconstituting dried peptides comprises or consists of 75% v/v aqueous solution comprising 0.1M citric acid, 6.25% v/v propylene glycol, 12.5% v/v ethanol, and 6.25% v/v polyoxyethyleneglyceroltriricinoleate 35.

13. A pharmaceutical composition comprising a mix of peptides consisting of:
   (i) 5 peptides consisting of the sequences set forth in SEQ ID NOs: 1-5; or
   (ii) 6 peptides consisting of the sequences set forth in SEQ ID NOs: 1-6; or
   (iii) 7 peptides consisting of the sequences set forth in SEQ ID NOs: 7-13.

14. The pharmaceutical composition according to claim 13, further comprising an adjuvant.

15. The pharmaceutical composition according to claim 14, wherein the adjuvant is an immune-stimulating adjuvant.

16. The pharmaceutical composition according to claim 14, wherein the adjuvant is an oil-based adjuvant or wherein the adjuvant is selected from a mineral or non-mineral oil-based adjuvant.

17. The pharmaceutical composition according to claim 16, wherein the oil-based adjuvant is selected from bio-based oil adjuvants, adjuvants based on vegetable oil or fish oil, squalene-based adjuvant, MF59, Syntex Adjuvant Formulation, Freund's Complete Adjuvant, Freund's Incomplete Adjuvant, adjuvants based on peanut oil, Adjuvant 65, Lipovant, ASO4, Montanide adjuvants, adjuvants based on purified squalene and squalene emulsified with highly purified mannide mono-oleate, and a mixture of Drakeol VR and mannide monooleate.

18. The pharmaceutical composition according to claim 14, wherein the composition comprises or consists of 1-2 mg/mL peptides in 40-60% v/v of the reconstitution composition and 40-60% v/v of Montanide ISA 51VG.

19. The pharmaceutical composition according to claim 13, wherein the mix of peptides is chemically stable for at least 2 hours at room temperature.

20. A method for making a stable pharmaceutical composition, the method comprising reconstituting peptides selected from:
  (i) a mix of peptides consisting of 5 peptides consisting of the sequences set forth in SEQ ID NOs: 1-5; or
  (ii) a mix of peptides consisting of 6 peptides consisting of the sequences set forth in SEQ ID NOs: 1-6; or
  (iii) a mix of peptides consisting of 7 peptides consisting of the sequences set forth in SEQ ID NOs: 7-13
  in reconstitution solution comprising 60-80% v/v aqueous solution comprising an organic acid, 5-10% v/v propylene glycol, 10-20% v/v lower alcohol, and 5-10% v/v non-ionic hydrophilic surfactant.

* * * * *